(12) United States Patent
Carninci et al.

(10) Patent No.: US 9,353,370 B2
(45) Date of Patent: May 31, 2016

(54) FUNCTIONAL NUCLEIC ACID MOLECULE AND USE THEREOF

(75) Inventors: Piero Carninci, Yokohama (JP); Alistair Forrest, Yokohama (JP); Stefano Gustincich, Trieste (IT); Claudia Carrieri, Rome (IT); Silvia Zucchelli, Trieste (IT)

(73) Assignees: Riken, Saitama (JP); International School for Advanced Studies, Trieste (IT)

( * ) Notice: Subject to any disclaimer, the term of this patent is extended or adjusted under 35 U.S.C. 154(b) by 0 days.

(21) Appl. No.: 14/008,186

(22) PCT Filed: Mar. 30, 2012

(86) PCT No.: PCT/JP2012/059430
§ 371 (c)(1),
(2), (4) Date: Dec. 26, 2013

(87) PCT Pub. No.: WO2012/133947
PCT Pub. Date: Oct. 4, 2012

(65) Prior Publication Data
US 2014/0107187 A1 Apr. 17, 2014

Related U.S. Application Data

(60) Provisional application No. 61/469,399, filed on Mar. 30, 2011.

(51) Int. Cl.
*C07H 21/04* (2006.01)
*C12N 15/113* (2010.01)
*C12N 15/67* (2006.01)
*C12N 15/11* (2006.01)

(52) U.S. Cl.
CPC .............. *C12N 15/113* (2013.01); *C12N 15/67* (2013.01); *C12N 15/111* (2013.01); *C12N 2310/11* (2013.01); *C12N 2310/3519* (2013.01)

(58) Field of Classification Search
None
See application file for complete search history.

(56) References Cited

U.S. PATENT DOCUMENTS

2008/0171715 A1* 7/2008 Brown et al. .................. 514/44

OTHER PUBLICATIONS

Smalheiser et al. (Trends in Genetics, 2005, vol. 21, No. 6; 322-326).*

* cited by examiner

*Primary Examiner* — Kimberly Chong
(74) *Attorney, Agent, or Firm* — Fish & Richardson P.C.

(57) ABSTRACT

The present invention provides (a) a functional nucleic acid molecule comprises: a target determinant sequence comprising antisense sequence to a target sequence in the protein-encoding RNA for which protein synthesis efficiency is to be increased and a regulatory sequence having an activity of increasing of the protein synthesis efficiency, and (b) a use of the functional nucleic acid molecule.

18 Claims, 17 Drawing Sheets

F I G. 1
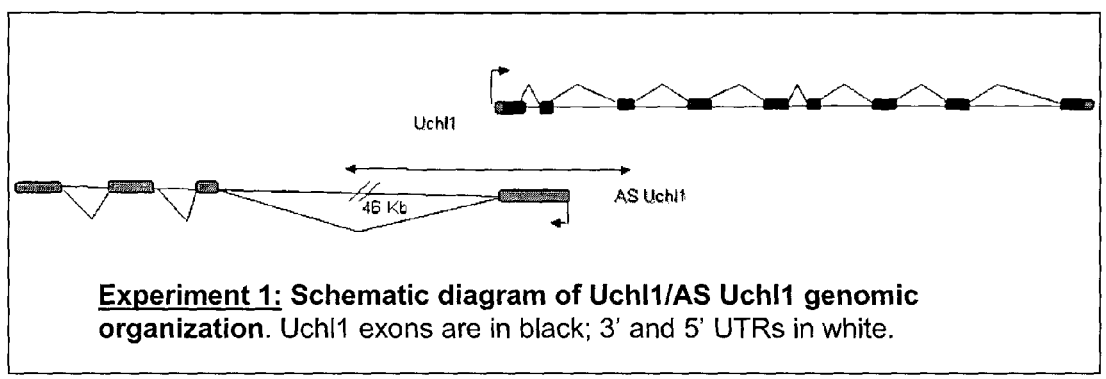
Experiment 1: Schematic diagram of Uchl1/AS Uchl1 genomic organization. Uchl1 exons are in black; 3' and 5' UTRs in white.

Experiment 2: Schematic diagram of AS Uchl1 domain organization. AS Uchl1 exons are in grey; repetitive elements are in red (Alu/SINEB1) and blue (SINEB2). Introns are indicated as lines.

Experiment 3: AS Uchl1 regulates UchL1 protein levels. AS Uchl1-transfected MN9D cells show increased levels of endogenous UchL1 protein relative to empty vector control, with unchanged mRNA quantity.

Experiment 4: AS Uch1 regulates UchL1 protein levels. Increasing doses of transfected AS Uchl1 titrate quantity of UchL1 protein in HEK cells. No changes in Uchl1 mRNA levels.

Experiment 5: AS Uchl1 regulates UchL1 protein levels. Full length (FL) AS Uchl1 is required for regulating endogenous (MN9D cells, left panel) and overexpressed (HEK cells, right panel) UchL1 protein levels. Scheme of Δ5' or Δ3' deletion mutants is shown.

FIG. 7

| Riken Acc. | AS to gene | NCBI Acc. | Orientation | Type |
|---|---|---|---|---|
| AK019925 | Cdc44 | NM_027346 | RC | SINE/B2 #B3 |
| AK029359 | Uxt | NM_013840 | RC | SINE/B2 #B3 |
| AK032194 | Nars2 | NM_153591 | RC | SINE/B2 #B3 |
| AK032215 | Nudt9 | NM_028794 | RC | SINE/B2 #B3 |
| AK034331 | n/a | NM_001012311 | RC | SINE/B2 #B3 |
| AK035015 | Nrm | NM_134122 | RC | SINE/B2 #B3 |
| AK035406 | Sv2b | NM_153579 | RC | SINE/B2 #B3 |
| AK041236 | Ccdc88a | NM_176841 | RC | SINE/B2 #B3 |
| AK041654 | Rcc | NM_133878 | RC | SINE/B2 #B3 |
| AK041742 | Abhd11 | NM_145215 | RC | SINE/B2 #B3 |
| AK042861 | Wfdc5 | NM_145389 | RC | SINE/B2 #B3 |
| AK044205 | Rhod | NM_007485 | RC | SINE/B2 #B3 |
| AK045877 | Eln | NM_007925 | RC | SINE/B2 #B3 |
| AK046828 | n/a | NM_177006 | RC | SINE/B2 #B3 |
| AK047213 | Uhmk1 | NM_010633 | RC | SINE/B2 #B3 |
| AK048309 | Epb4.9 | NM_013514 | RC | SINE/B2 #B3 |
| AK053130 | Rabgap1l | NM_001038621 | RC | SINE/B2 #B3 |
| AK054076 | Gadd45a | NM_007836 | RC | SINE/B2 #B3 |
| AK078161 | Nck1 | NM_010878 | RC | SINE/B2 #B3 |
| AK078321 | Uchl1 | NM_011670 | RC | SINE/B2 #B3 |
| AK080749 | Pgls | NM_025396 | RC | SINE/B2 #B3 |
| AK090347 | 3110005G23Rik | NM_028427 | RC | SINE/B2 #B3 |
| AK132441 | A130022J15Rik | NM_175313 | RC | SINE/B2 #B3 |
| AK135599 | Ednra | NM_010332 | RC | SINE/B2 #B3 |
| AK143014 | Cdkn2aip | NM_172407 | RC | SINE/B2 #B3 |
| AK143784 | Txnip | NM_001009935 | RC | SINE/B2 #B3 |
| AK145079 | Gsk3b | NM_019827 | RC | SINE/B2 #B3 |
| AK149843 | Cmtm6 | NM_026036 | RC | SINE/B2 #B3 |
| AK163105 | E4f1 | NM_007893 | RC | SINE/B2 #B3 |
| AK165234 | Dbx3 | NM_030714 | RC | SINE/B2 #B3 |
| AK169421 | n/a | NM_001110101 | RC | SINE/B2 #B3 |

Experiment 7: Family of AS transcripts with embedded SINEB2.
Family of FANTOM 3 non-coding clones that are AS to protein coding genes and contain embedded SINEB2 in inverted orientation.

Experiment 8: Family of AS transcripts with embedded SINEB2.
Schematic diagram of Uxt/AS Uxt genomic organization. AS Uxt
increases endogenous Uxt protein levels in transfected MN9D cells (left),
without affecting its transcription (right).

Experiment 9: Expression of AS Uchl1 in the nucleus of dopaminergic neurons. AS Uchl1 (red) and Uchl1 (green) transcripts are expressed in the nucleus and cytoplasm of TH-positive DA neurons of the Substantia Nigra (blue). Details of localization are in zoom images.

Experiment 10: AS Uchl1 translocates to the cytoplasm upon rapamycin treatment in MN9D cells. mRNA levels measured with primers spanning 5' overlapping or 3' distal portions of the transcript. Data indicate mean ± s.d., n≥3 (3). p<0.01; *p<0.005.

Experiment 11: Rapamycin treatment induces UchL1 protein expression. UchL1 protein level is increased in rapamycin-treated MN9D cells.

Experiment 12: AS Uchl1-embedded SINEB2 induces translation of Uchl1 upon rapamycin treatment. Silencing AS Uchl1 transcription in MN9D cells (shRNA, encompassing -15/+4 position of target sequence) inhibits rapamycin-induced UchL1 protein level. Scramble, shRNA control sequence. Left, mRNA levels; right, protein levels.

Experiment 13: AS Uchl1-embedded SINEB2 induces translation of Uchl1 upon rapamycin treatment. Deletion of embedded SINEB2 (Δ SINEB2) is sufficient to inhibit rapamycin-induced UchL1 protein up-regulation.

FIG. 14

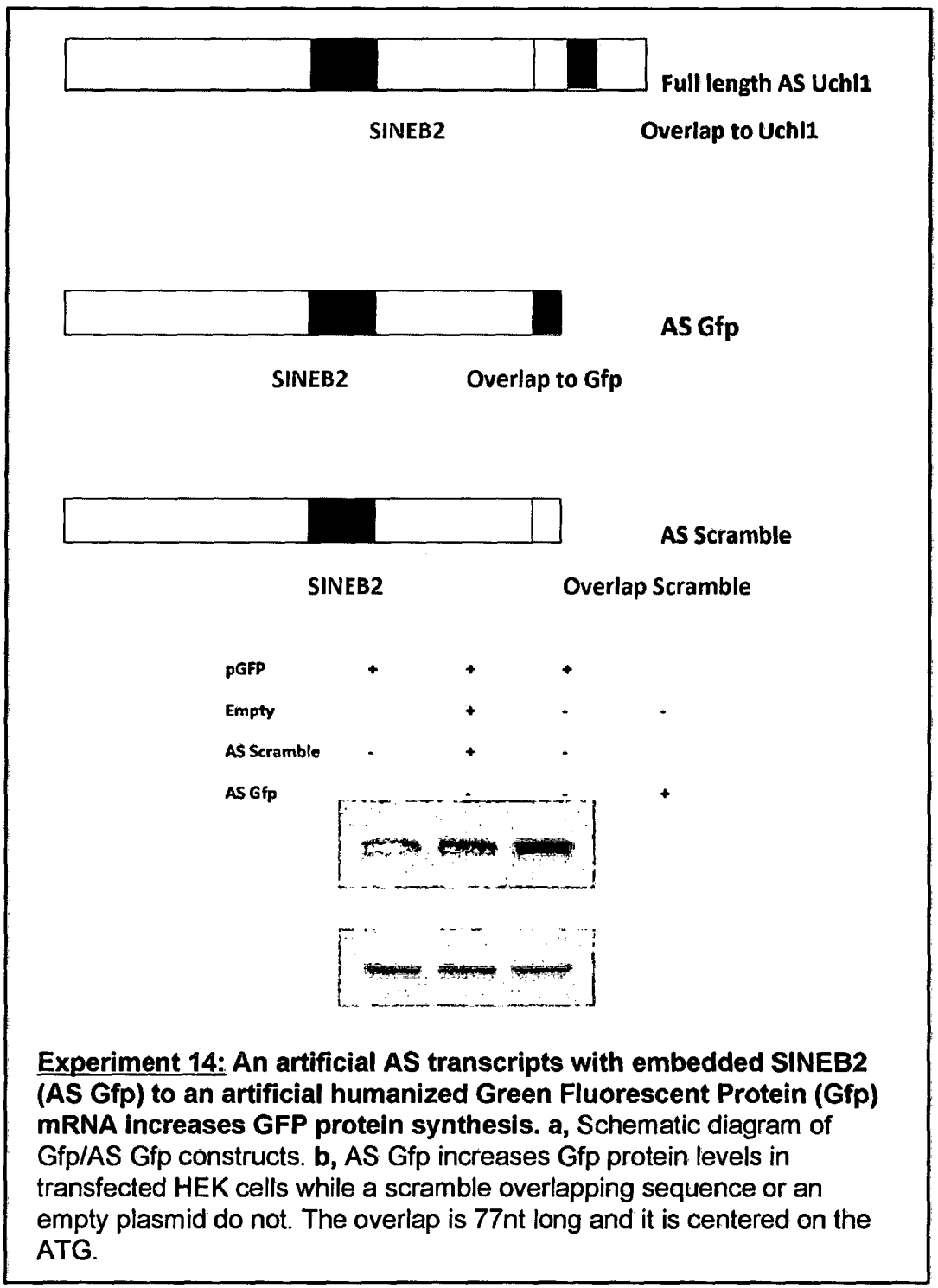

Experiment 14: An artificial AS transcripts with embedded SINEB2 (AS Gfp) to an artificial humanized Green Fluorescent Protein (Gfp) mRNA increases GFP protein synthesis. a, Schematic diagram of Gfp/AS Gfp constructs. b, AS Gfp increases Gfp protein levels in transfected HEK cells while a scramble overlapping sequence or an empty plasmid do not. The overlap is 77nt long and it is centered on the ATG.

SEQUENCE LISTING

```
<160> NUMBER OF SEQ ID NOS: 47

<210> SEQ ID NO 1
<211> LENGTH: 250
<212> TYPE: DNA
<213> ORGANISM: Mus musculus

<400> SEQUENCE: 1
tgctccccgg actgggcatg gtagcacgca cctgtgattc cagcagctga gagagaggcc      60
gagcccacat ggaatccatt gtgcagtgct agaggaggtc agaagagggc attggatccc     120
ccagaactgg agttatacgg taacctcgtg gtggttgtga accaccatgt ggatggatat     180
tgagttccaa acactggtcc tgtgcaagag catccagtgc tcttaagtgc tgagccatct     240
ctttagctcc                                                            250

<210> SEQ ID NO 2
<211> LENGTH: 363
<212> TYPE: DNA
<213> ORGANISM: Mus musculus

<400> SEQUENCE: 2
gtgctccccg gactgggcat ggtagcacgc acctgtgatt ccagcagctg agagagaggc      60
cgagcccaca tggaatccat tgtgcagtgc tagaggaggt cagaagaggg cattggatcc     120
cccagaactg gagttatacg gtaacctcgt ggtggttgtg aaccaccatg tggatggata     180
ttgagttcca aacactggtc ctgtgcaaga gcatccagtg ctcttaagtg ctgagccatc     240
```

| | |
|---|---|
| tctttagctc cagtctctta aaaaacaaac aaacgaacga acagcaaggg agctgggtat | 300 |
| gacaacacat actataattc tagtactcag gatgctgaaa caggaggatt gcctgactgg | 360 |
| gag | 363 |

<210> SEQ ID NO 3
<211> LENGTH: 187
<212> TYPE: DNA
<213> ORGANISM: Mus musculus

<400> SEQUENCE: 3

| | |
|---|---|
| ttattttaaa tatatgagta tttcacctgc ataggcgcac agtacccaca gagactagaa | 60 |
| gagggtggca gatctcctga gactggagtt aatgcttgtg agctgccatg tggatgctgg | 120 |
| aaatcaaacc caggtccttt ggaaggcagg caggtgctct taatcatgga agcatctctt | 180 |
| cagctcc | 187 |

<210> SEQ ID NO 4
<211> LENGTH: 1146
<212> TYPE: DNA
<213> ORGANISM: Mus musculus

<400> SEQUENCE: 4

| | |
|---|---|
| gggagttcga gccctcttgg ccttcctcct ctgcttgttt ctgctcccgt ctccctgct | 60 |
| caggctttcc cagtgagcga ggccggcgct ttataacagc agcctgggcg gctccaccgg | 120 |
| ctgttttttc ggctcctcgg gtttgtgtct gcaggtgcca tccgcgaaga tgcagctgaa | 180 |
| gccgatggag attaaccccg agatgctgaa caaagtgttg gccaagctgg gggtcgccgg | 240 |
| ccagtggcgc ttcgccgacg tgctagggct ggaggaggag actctgggct cagtgccatc | 300 |
| ccctgcctgc gccctgctgc tcctgtttcc cctcacggcc cagcatgaaa acttcaggaa | 360 |
| aaagcaaatt gaggaactga agggacagga agttagccct aaagtttact tcatgaagca | 420 |
| gaccatcgga aactcctgtg gtaccatcgg gttgatccac gcagtggcca acaaccaaga | 480 |
| caagctggaa tttgaggatg gatccgtcct gaaacagttt ctgtctgaaa cggagaagct | 540 |
| gtcccccgaa gatagagcca agtgtttcga gaagaacgag gccatccagg cggcccatga | 600 |
| ctccgtggcc caggagggcc agtgtcgggt agatgacaaa gtgaatttcc attttattct | 660 |
| gttcaacaac gtggacggcc atctgtacga gctcgatggg cgaatgccct ttccagtgaa | 720 |
| ccatggcgcc agctcagagg actctctgct gcaggatgct gccaaggtct gcagagaatt | 780 |
| cactgagcgc gagcaggggg aggtccgctt ctctgccgtg gctctctgca aagcagctta | 840 |
| agtctgggga gagagaacca gccgatcccc ccttccctgg gcaggtgcgc gcggcccgcc | 900 |
| cttggtttgc agctttagca cttagaacca cagctgtctt cttgcgttct acagcccat | 960 |
| cccctccacc ccacccaggc caccaggggg ctctgtcaca gccacaccag gctgagcact | 1020 |
| ttccctcctg tgtgtctcgt accttgctct ctacggtctc tttggttttct gtctgtaagt | 1080 |
| tacggccctg gatgtggttt gtctagtcct taagaggaag aataaaactt tgctggtgag | 1140 |
| agtatc | 1146 |

<210> SEQ ID NO 5
<211> LENGTH: 875
<212> TYPE: DNA
<213> ORGANISM: Mus musculus

<400> SEQUENCE: 5

| | |
|---|---|
| atccatccgc gccacccgga agccgcggct catactaaca gttattgccg gtggccctac | 60 |

```
ggtaaacgcc gtactcctgt accggtgccc gtcatggcga cgcccccgaa acggcgggcc      120
ttggatacgg tgggggagaa agtgctgcgg tacgagacct ttatcagtga cgtactgcag      180
cgagacttgc aaaaggtgct ggatcatcga acaaggtat atgagcagct gtccgtatat       240
cttcaactaa gaaatgtcat tgagcgactc caggaaacta atcactcgga gttatatatg      300
caggtggatt tgggctgtaa cttcttcgtt gacacagtgg tcccagatac ttcacgcatc      360
tatgtggccc tgggatatgg ttttttcctg aactgacac tggctgaagc actcaagttc       420
attgaccgaa agagttctct cctcacagag ctcagcgaca gcctcaccaa ggactccatg      480
aatatcaagg cccatatcca catgatgcta gagggactta gagaactaca aggcctgcag      540
aatttcccag agccatctcc ccattgactg catcttccca gcctccaata ttaaagcacc      600
tgaatgcctt ggaatcacat agtcctttt tccctaattc tcactaattt actaagtgcc       660
ctagagacca aaattactgg aagacccatc ctttctgtag aacctctaaa acgttctaga      720
ggtcttgcct agaacttgtg ttttctcct gactttatgc tttactctct tttgtcgcct       780
ttagaacctt ggccctgctc ctcacaattc cttttcctag atatttgtat ctgtgccctt      840
tgtcttacca taaagaatgg actgaatggg ctgaa                                 875

<210> SEQ ID NO 6
<211> LENGTH: 748
<212> TYPE: DNA
<213> ORGANISM: Mus musculus

<400> SEQUENCE: 6
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgaccta cggcgtgcag tgcttcagcc gctacccga ccacatgaag       240 cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgagca cccagtccgc cctgagcaaa gaccccaacg agaagcgcga tcacatggtc     660
ctgctggagt tcgtgaccgc cgccgggatc actctcggca tggacgagct gtacaagtcc     720
ggactcagat ctcgagctca agcttcga                                        748

<210> SEQ ID NO 7
<211> LENGTH: 1685
<212> TYPE: DNA
<213> ORGANISM: Mus musculus

<400> SEQUENCE: 7
aaacgatgct cttggaggat agggacagag actgcgcgcc gcgccactca ctttgttcag      60
catctgaaag ccaaaagcaa agaggaaaat gataataaaa ctaaatgatt cagctaccga     120
gctgtagcta agggtcagcc ttatttctcc cgaagcgacc cagcagctat gcttacctcg     180
gggttaatct ccatcggctt cagctgcatc ttcgcggatg gcacctgcag acacaaaccc     240
```

```
gaggagccga aaaaacagcc ggtggagccg cccaggctgc tgttataaag cgccggcctc        300
gctcactggg aaagcctgag caggggagac gggagcagaa acaagcagag gaggaaggcc        360
aagagggctc gaactccccc atgcaccgca cagaatggta caagccaagc ccccaaacct        420
tgcagtctca ctcgccgaag tgctcccgg actgggcatg gtagcacgca cctgtgattc         480
cagcagctga gagagaggcc gagcccacat ggaatccatt gtgcagtgct agaggaggtc        540
agaagagggc attggatccc ccagaactgg agtgatacgg taacctcgtg gtggttgtga        600
accaccatgt ggatggatat tgagttccaa acactggtcc tgtgcaagag catccagtgc        660
tcttaagtgc tgagccatct ctttagctcc agtctcttaa aaaacaaaca aacgaacgaa        720
cagcaaggga gctgggtatg acaacacata ctataattct agtactcagg atgctgaaac        780
aggaggattg cctgactggg agatataagg agaatctgtt gtcaccccca ccctccccca        840
taaaggcaga ataaagaac gtcctataaa caaataaaca aacaacccaa taaacaaaa          900 ccaagatctc tccaccttt ctttgctttt tcagactttg taataaggcc ctttggagtg         960
caggatattc ggcaggacaa gcagagaggg agaccatcag ttctttcttt gatcaagaag        1020
actatgttcc ttagcaaact ggtgtgtatt atctcttatg caatgagcct ggaaagaggg        1080
cacagccacc gaggatggta cagcatggat ggatggtacg ctacagagac tcgggagccc       1140
aactgtgagt ggctgactgg catggtaggt tcagggaaga attggcctgt gaagaaaatg        1200
ttcttgaaaa gtgaacaagg tgcaggaggt aggagtgggt cctgggcaaa gcaggggtg        1260 catcccagcc tcaggaata gcacagcaga ggtctgttga tgcatgcgag tgcatgacct         1320
gcttgccaat agacgatcaa gaatgggcaa agcatcatgg gtgatgagtg ggagagggga      1380
tgagacattc cttctcccct gctgagactt ccattgaacc gatgagttct gaatagaaga       1440
tgccccccca ccccccccacc agtgtagaat ctgaagggag gcatatatta ccctatatta    1500
ctctgtgttg gcggcgagct atctgacagc caaccttccc atacatttca ttgggcatac     1560
actaatgaca ggaagttcct tttgcttgta tgcaagagat ggctcacacg atggagaatt     1620
taatcttgtt agtttgttat ttatgtgtcc taaattttgt tcaataaaaa tgaaacactc    1680
ctatg                                                                 1685

<210> SEQ ID NO 8
<211> LENGTH: 1145
<212> TYPE: DNA
<213> ORGANISM: Mus musculus

<400> SEQUENCE: 8
tagtctcgct gcagtacgtc actgataaag ccactcaacg ttggggatga cttctttcgg        60
ctcgagctac ggagttgctt ctgcccaacc cgattttgga actcgttcac tcaccggtac       120
aggagtacgg cgtttaccgt agggccaccg gcaataactg ccagaagaag ttgtgggatt       180
ccctggaact ggagcaacca acagtttgtg tgcaccatgt gggtaatggg aatcgaacct      240
gggtcctcta taagactggc cagtgctctt aactactgag gtgcatttct ttcggaattg     300
attcacataa ctattatgct atactgtttg aagtatttat tagaaaaaca tcagaaagag    360
atttggacca ctttcattta catgaagaaa tatcttaggg ttttctttca ggtatctttg    420
agtatcttct gacactagaa gatcctgtaa actctacaga cttcaacaga attgaagaac   480
ctggacagag cagagttacc aacaagagag cccagggata gcattaacat ggtggttact    540
caagacctaa ctcagccagg gagacatacc aaggcctatg aggtgaaggg aaaagaaggg    600
tgacccaaag ggcaggaatt ttttatcctg aacttttgag ccttatagaa aaacataatt    660
```

| | | |
|---|---|---|
| tgttgggcat gttttctgac cctcatacag ttttttacaac catttgaaga tatagttcta | 720 | |
| gctctagtag gctctacagg aaggtatatc aaacttttta acagaacact ttattatttt | 780 | |
| aaatatatga gtatttcacc tgcataggcg cacagtaccc acagagacta gaagagggtg | 840 | |
| gcagatctcc tgagactgga gttaatgctt gtgagctgcc atgtggatgc tggaaatcaa | 900 | |
| acccaggtcc tttggaaggc aggcaggtgc tcttaatcat ggaagcatct cttcagctcc | 960 | |
| taccctagtt ctttaatttt gttttaaatt tttgaggtag ggttttgcta agttacttgg | 1020 | |
| gctggccttg gactagtaac cattctgtgt cagccttctg ggattagagg tatgtgctag | 1080 | |
| catgtctagc atctttctat ttctttggtt ttccttctaa ttaattaaaa aatacattat | 1140 | |
| cttct | 1145 | |

```
<210> SEQ ID NO 9
<211> LENGTH: 209
<212> TYPE: DNA
<213> ORGANISM: Mus musculus

<400> SEQUENCE: 9
```

| | | |
|---|---|---|
| gggctggaga gatggctcag tggttaagag cacctgactg ctcttccagc ggtcctgagt | 60 | |
| tcaattccca gcaaccacat ggtggctcac aaccatctgt aatgagatct gatgccctct | 120 | |
| tctggtgtgt ctgaagacag ctacagtgta cttacatata ataaataaat aaataaataa | 180 | |
| atcttaaaaa aaaaaaaaag aaagaaaaa | 209 | |

```
<210> SEQ ID NO 10
<211> LENGTH: 228
<212> TYPE: DNA
<213> ORGANISM: Mus musculus
<220> FEATURE:
<221> NAME/KEY: misc_feature
<222> LOCATION: (125)..(125)
<223> OTHER INFORMATION: n is a, c, g, or t

<400> SEQUENCE: 10
```

| | | |
|---|---|---|
| ggggctggag agatagctca gcggttaaga gcactggctg ctcttccaga ggacccgggt | 60 | |
| tcggttccca gcaccacat ggcggctcac aaccgtctgt aactctagtt ccaggggatc | 120 | |
| tracncccte ttctgacctc cacgggcacc aggcacgcac gtggtacaca gacgtacatg | 180 | |
| cargcaaaac actcatacac ataaaataaa aataaatmtt twaaaaaa | 228 | |

```
<210> SEQ ID NO 11
<211> LENGTH: 1013
<212> TYPE: DNA
<213> ORGANISM: Mus musculus

<400> SEQUENCE: 11
```

| | | |
|---|---|---|
| cggctcctcg ggtttgtgtc tgcaggtgcc atccgcgaag atgcagctga agccgatgga | 60 | |
| gattaacccc gagatgctga acaaagtgtt ggccaagctg ggggtcgccg ccagtggcg | 120 | |
| cttcgccgac gtgctagggc tggaggagga gactctgggc tcagtgccat cccctgcctg | 180 | |
| cgccctgctg ctcctgtttc ccctcacggc ccagcatgaa aacttcagga aaaagcaaat | 240 | |
| tgaggaactg aagggacagg aagttagccc taaagtttac ttcatgaagc agaccatcgg | 300 | |
| aaactcctgt ggtaccatcg ggttgatcca cgcagtggcc aacaaccaag acaagctgga | 360 | |
| atttgaggat ggatccgtcc tgaaacagtt tctgtctgaa acggagaagc tgtccccga | 420 | |
| agatagagcc aagtgtttcg agaagaacga ggccatccag gcggcccatg actccgtggc | 480 | |

-continued

| | |
|---|---|
| ccaggagggc cagtgtcggg tagatgacaa agtgaatttc cattttattc tgttcaacaa | 540 |
| cgtggacggc catctgtacg agctcgatgg gcgaatgccc tttccagtga accatggcgc | 600 |
| cagctcagag gactctctgc tgcaggatgc tgccaaggtc tgcagagaat tcactgagcg | 660 |
| cgagcagggg gaggtccgct ctctgccgt ggctctctgc aaagcagctt aagtctgggg | 720 |
| agagagaacc agccgatccc cccttccctg ggcaggtgcg cgcggcccgc ccttggtttg | 780 |
| cagctttagc acttagaacc acagctgtct tcttgcgttc tacagcccca tcccctccac | 840 |
| cccacccagg ccaccagggg gctctgtcac agccacacca ggctgagcac tttccctcct | 900 |
| gtgtgtctcg taccttgctc tctacggtct ctttggtttc tgtctgtaag ttacggccct | 960 |
| ggatgtggtt tgtctagtcc ttaagaggaa gaataaaact ttgctggtga gag | 1013 |

<210> SEQ ID NO 12
<211> LENGTH: 1929
<212> TYPE: DNA
<213> ORGANISM: Mus musculus

<400> SEQUENCE: 12

| | |
|---|---|
| acaaagctca gcccacacgt ggctcgcgcg aagccctcgg actagagtcc gcgggccgtc | 60 |
| gccacgccct cgagagctgc tccccgcgct cgttgctgtc cgggtccatc ctccgccacc | 120 |
| tccccgtgat cgatctctca gtcactccca accccctaga taactcaggg cagagacgac | 180 |
| acccagctgg gcgccccagc ccagccacct ccattgcaca gggcgcggcc ggctgggcgt | 240 |
| ctccaaacga tgctcttgga ggatagggac agagactgcg cgccgcgcca ctcactttgt | 300 |
| tcagcatctg aaagccaaaa gcaaagagga aatgataat aaaactaaat gattcagcta | 360 |
| ccgagctgta gctaagggtc agccttattt ctcccgaagc gacccagcag ctatgcttac | 420 |
| ctcggggtta atctccatcg gcttcagctg catcttcgcg gatggcacct gcagacacaa | 480 |
| acccgaggag ccgaaaaaac agccggtgga gccgcccagg ctgctgttat aaagcgccgg | 540 |
| cctcgctcac tgggaaagcc tgagcagggg agacgggagc agaaacaagc agaggaggaa | 600 |
| ggccaagagg gctcgaactc ccccatgcac cgcacagaat ggtacaagcc aagcccccaa | 660 |
| accttgcagt ctcactcgcc gaagtgctcc ccggactggg catggtagca cgcacctgtg | 720 |
| attccagcag ctgagagaga ggccgagccc acatggaatc cattgtgcag tgctagagga | 780 |
| ggtcagaaga gggcattgga tcccccagaa ctggagttat acggtaacct cgtggtggtt | 840 |
| gtgaaccacc atgtggatgg atattgagtt ccaaacactg gtcctgtgca agagcatcca | 900 |
| gtgctcttaa gtgctgagcc atctctttag ctccagtctc ttaaaaaaca aacaaacgaa | 960 |
| cgaacagcaa gggagctggg tatgacaaca catactataa ttctagtact caggatgctg | 1020 |
| aaacaggagg attgcctgac tgggagatat aaggagaatc tgttgtcacc cccacccctc | 1080 |
| cccataaagg cagaataaaa gaacgtccta taaacaaata aacaaacaac ccaataaaac | 1140 |
| aaaaccaaga tctctccacc tttttctttgc tttttcagac tttgtaataa ggccccttgg | 1200 |
| agtgcaggat attcggcagg acaagcagag agggagacca tcagttcttt ctttgatcaa | 1260 |
| gaagactatg ttccttagca aactggtgtg tattatctct tatgcaatga gcctggaaag | 1320 |
| agggcacagc caccgaggat ggtacagcat ggatggatgg tacgctacag agactcggga | 1380 |
| gcccaactgt gagtggctga ctggcatggt aggttcaggg aagaattggc ctgtgaagaa | 1440 |
| aatgttcttg aaaagtgaac aaggtgcagg aggtaggagt gggtcctggg caaagcaggg | 1500 |
| ggtgcatccc agcctcaggg aatagcacag cagaggtctg ttgatgcatg cgagtgcatg | 1560 |
| acctgcttgc caatagacga tcaagaatgg gcaaagcatc atgggtgatg agtgggagag | 1620 |

```
gggatgagac attcctttct ccctgctgag acttccattg aaccgatgag ttctgaatag    1680
aagatgcccc cccaccccc caccagtgta gaatctgaag ggaggcatat attaccctat    1740
attactctgt gttggcggcg agctatctga cagccaacct tcccatacat ttcattgggc    1800
atacactaat gacaggaagt tcctttgct tgtatgcaag agatggctca cacgatggag     1860
aatttaatct tgttagtttg ttatttatgt gtcctaaatt ttgttcaata aaaatgaaac    1920
actcctatg                                                            1929
```

<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13
acaaagctca gcccacacgt                                                 20

<210> SEQ ID NO 14
<211> LENGTH: 13
<212> TYPE: DNA
<213> ORGANISM: Artificial Sequence
<220> FEATURE:
<223> OTHER INFORMATION: primer

<400> SEQUENCE: 14
catagggttc att                                                        13

<210> SEQ ID NO 15
<211> LENGTH: 18
<212> TYPE: DNA
<213> ORGANISM: Artificial Sequence
<220> FEATURE:
<223> OTHER INFORMATION: primer

<400> SEQUENCE: 15
atgcagctga agccgatg                                                   18

<210> SEQ ID NO 16
<211> LENGTH: 21
<212> TYPE: DNA
<213> ORGANISM: Artificial Sequence
<220> FEATURE:
<223> OTHER INFORMATION: primer

<400> SEQUENCE: 16
ttaagctgct ttgcagagag c                                               21

<210> SEQ ID NO 17
<211> LENGTH: 21
<212> TYPE: DNA
<213> ORGANISM: Artificial Sequence
<220> FEATURE:
<223> OTHER INFORMATION: primer

<400> SEQUENCE: 17
cgcgcagtga cacagcacaa a                                               21

<210> SEQ ID NO 18
<211> LENGTH: 19
<212> TYPE: DNA
<213> ORGANISM: Artificial Sequence
<220> FEATURE:

```
<223> OTHER INFORMATION: primer

<400> SEQUENCE: 18
taccattctg tgcggtgca                                            19

<210> SEQ ID NO 19
<211> LENGTH: 21
<212> TYPE: DNA
<213> ORGANISM: Artificial Sequence
<220> FEATURE:
<223> OTHER INFORMATION: primer

<400> SEQUENCE: 19
gacctcctct agcactgcac a                                         21

<210> SEQ ID NO 20
<211> LENGTH: 15
<212> TYPE: DNA
<213> ORGANISM: Artificial Sequence
<220> FEATURE:
<223> OTHER INFORMATION: primer

<400> SEQUENCE: 20
caatggattc catgt                                                15

<210> SEQ ID NO 21
<211> LENGTH: 17
<212> TYPE: DNA
<213> ORGANISM: Artificial Sequence
<220> FEATURE:
<223> OTHER INFORMATION: primer

<400> SEQUENCE: 21
gatataagga gaatctg                                              17

<210> SEQ ID NO 22
<211> LENGTH: 17
<212> TYPE: DNA
<213> ORGANISM: Artificial Sequence
<220> FEATURE:
<223> OTHER INFORMATION: primer

<400> SEQUENCE: 22
ttatagtatg tgttgtc                                              17

<210> SEQ ID NO 23
<211> LENGTH: 17
<212> TYPE: DNA
<213> ORGANISM: Artificial Sequence
<220> FEATURE:
<223> OTHER INFORMATION: primer

<400> SEQUENCE: 23
gatataagga gaatctg                                              17

<210> SEQ ID NO 24
<211> LENGTH: 15
<212> TYPE: DNA
<213> ORGANISM: Artificial Sequence
<220> FEATURE:
<223> OTHER INFORMATION: primer

<400> SEQUENCE: 24
caatggattc catgt                                                15
```

```
<210> SEQ ID NO 25
<211> LENGTH: 19
<212> TYPE: DNA
<213> ORGANISM: Artificial Sequence
<220> FEATURE:
<223> OTHER INFORMATION: primer

<400> SEQUENCE: 25
gaattcctcc agtctctta                                                   19

<210> SEQ ID NO 26
<211> LENGTH: 12
<212> TYPE: DNA
<213> ORGANISM: Artificial Sequence
<220> FEATURE:
<223> OTHER INFORMATION: primer

<400> SEQUENCE: 26
tgctagagga gg                                                          12

<210> SEQ ID NO 27
<211> LENGTH: 12
<212> TYPE: DNA
<213> ORGANISM: Artificial Sequence
<220> FEATURE:
<223> OTHER INFORMATION: primer

<400> SEQUENCE: 27
gtcaggcaat cc                                                          12

<210> SEQ ID NO 28
<211> LENGTH: 12
<212> TYPE: DNA
<213> ORGANISM: Artificial Sequence
<220> FEATURE:
<223> OTHER INFORMATION: primer

<400> SEQUENCE: 28
tgctagagga gg                                                          12

<210> SEQ ID NO 29
<211> LENGTH: 11
<212> TYPE: DNA
<213> ORGANISM: Artificial Sequence
<220> FEATURE:
<223> OTHER INFORMATION: primer

<400> SEQUENCE: 29
aaagagatgg c                                                           11

<210> SEQ ID NO 30
<211> LENGTH: 18
<212> TYPE: DNA
<213> ORGANISM: Artificial Sequence
<220> FEATURE:
<223> OTHER INFORMATION: primer

<400> SEQUENCE: 30
cacacccgcc accagttc                                                    18

<210> SEQ ID NO 31
<211> LENGTH: 20
<212> TYPE: DNA
<213> ORGANISM: Artificial Sequence
<220> FEATURE:
<223> OTHER INFORMATION: primer
```

```
<400> SEQUENCE: 31
cccattccca ccatcacacc                                              20

<210> SEQ ID NO 32
<211> LENGTH: 20
<212> TYPE: DNA
<213> ORGANISM: Artificial Sequence
<220> FEATURE:
<223> OTHER INFORMATION: primer

<400> SEQUENCE: 32
gcagtggcaa agtggagatt                                              20

<210> SEQ ID NO 33
<211> LENGTH: 20
<212> TYPE: DNA
<213> ORGANISM: Artificial Sequence
<220> FEATURE:
<223> OTHER INFORMATION: primer

<400> SEQUENCE: 33
gcagaagggg cggagatgat                                              20

<210> SEQ ID NO 34
<211> LENGTH: 19
<212> TYPE: DNA
<213> ORGANISM: Artificial Sequence
<220> FEATURE:
<223> OTHER INFORMATION: primer

<400> SEQUENCE: 34
gcacctgcag acacaaacc                                               19

<210> SEQ ID NO 35
<211> LENGTH: 20
<212> TYPE: DNA
<213> ORGANISM: Artificial Sequence
<220> FEATURE:
<223> OTHER INFORMATION: primer

<400> SEQUENCE: 35
tctctcagct gctggaatca                                              20

<210> SEQ ID NO 36
<211> LENGTH: 20
<212> TYPE: DNA
<213> ORGANISM: Artificial Sequence
<220> FEATURE:
<223> OTHER INFORMATION: primer

<400> SEQUENCE: 36
ctggtgtgta tctcttatgc                                              20

<210> SEQ ID NO 37
<211> LENGTH: 18
<212> TYPE: DNA
<213> ORGANISM: Artificial Sequence
<220> FEATURE:
<223> OTHER INFORMATION: primer

<400> SEQUENCE: 37
ctcccgagtc tctgtagc                                                18

<210> SEQ ID NO 38
<211> LENGTH: 18
```

```
<212> TYPE: DNA
<213> ORGANISM: Artificial Sequence
<220> FEATURE:
<223> OTHER INFORMATION: primer

<400> SEQUENCE: 38
cccgccgata gagccaag                                                  18

<210> SEQ ID NO 39
<211> LENGTH: 18
<212> TYPE: DNA
<213> ORGANISM: Artificial Sequence
<220> FEATURE:
<223> OTHER INFORMATION: primer

<400> SEQUENCE: 39
atggttcact ggaaaggg                                                  18

<210> SEQ ID NO 40
<211> LENGTH: 19
<212> TYPE: DNA
<213> ORGANISM: Artificial Sequence
<220> FEATURE:
<223> OTHER INFORMATION: primer

<400> SEQUENCE: 40
ccatgcaccg cacagaatg                                                 19

<210> SEQ ID NO 41
<211> LENGTH: 20
<212> TYPE: DNA
<213> ORGANISM: Artificial Sequence
<220> FEATURE:
<223> OTHER INFORMATION: primer

<400> SEQUENCE: 41
gaaagctccc tcaaataggc                                                20

<210> SEQ ID NO 42
<211> LENGTH: 22
<212> TYPE: DNA
<213> ORGANISM: Artificial Sequence
<220> FEATURE:
<223> OTHER INFORMATION: primer

<400> SEQUENCE: 42
tgtggtgtcc aagtgttcat gc                                             22

<210> SEQ ID NO 43
<211> LENGTH: 22
<212> TYPE: DNA
<213> ORGANISM: Artificial Sequence
<220> FEATURE:
<223> OTHER INFORMATION: primer

<400> SEQUENCE: 43
cggagcacca catcgatcta ag                                             22

<210> SEQ ID NO 44
<211> LENGTH: 20
<212> TYPE: DNA
<213> ORGANISM: Artificial Sequence
<220> FEATURE:
<223> OTHER INFORMATION: primer

<400> SEQUENCE: 44
```

```
caacgttggg gatgacttct                                              20

<210> SEQ ID NO 45
<211> LENGTH: 20
<212> TYPE: DNA
<213> ORGANISM: Artificial Sequence
<220> FEATURE:
<223> OTHER INFORMATION: primer

<400> SEQUENCE: 45
tcgattccca ttacccacat                                              20

<210> SEQ ID NO 46
<211> LENGTH: 20
<212> TYPE: DNA
<213> ORGANISM: Artificial Sequence
<220> FEATURE:
<223> OTHER INFORMATION: primer

<400> SEQUENCE: 46
ttgagcgact ccaggaaact                                              20

<210> SEQ ID NO 47
<211> LENGTH: 19
<212> TYPE: DNA
<213> ORGANISM: Artificial Sequence
<220> FEATURE:
<223> OTHER INFORMATION: primer

<400> SEQUENCE: 47
gagtcctggt gaggctgtc                                               19
```

FUNCTIONAL NUCLEIC ACID MOLECULE AND USE THEREOF

CROSS REFERENCE TO RELATED APPLICATIONS

This application is a national stage filing under 35 U.S.C. §371 of international application number PCT/JP2012/059430, filed Mar. 30, 2012, which claims the benefit of provisional patent application 61/469,399, filed Mar. 30, 2011. Each of these applications is incorporated by reference in its entirety.

TECHNICAL FIELD

The present invention relates to (a) a functional nucleic acid molecule having a function of increasing the protein synthesis efficiency, and (b) a use of the functional nucleic acid molecule.

BACKGROUND ART

There are various types of functional nucleic acid molecules, typified by relatively long functional RNA molecules such as antisense RNA, for example. Other typical examples of the functional nucleic acid molecules are relatively short functional RNA molecules such as shRNA (short hairpin RNA), siRNA (small interfering RNA), and miRNA (micro interfering RNA). These functional RNA molecules are generally known to contribute to down-regulation of gene expression. Various examples have been broadly reviewed as "interfering RNA" like in (Non Patent Literature 1).

An antisense RNA technique is excellent in target specificity. However, this technique has a disadvantage that an antiviral response in a cell is activated. In contrast, the technique using the relatively short functional RNA molecules such as shRNA does not activate the antiviral response practically. Instead, the relative short functional RNA molecules have the possibility of causing the off-target effects because it is difficult for short sequence length to keep high specificity to the target sequences. Thus, the relatively short functional RNA molecules tend to exhibit poor target specificity as compared with the antisense RNA technique.

Patent Literature 1 discloses a functional nucleic acid molecule (DNA molecule) comprising: a pol III type III promoter; a sequence identical or complementary to a target sequence that performs downregulation; and a 7SL small-RNA derived sequence (more specifically, a fragment of an Alu derived sequence) including at least binding domains to srp9 and srp14 proteins. The srp9 and srp14 proteins are members of a family of proteins that bind to a 7SL RNA in gene transcription to form a 7SL RNA complex.

It is described that the functional nucleic acid molecule disclosed in Patent Literature 1 is used as a gene expression downregulation technique in which an RNA molecule transcribed from the functional nucleic acid molecule practically causes no antiviral response activation and has excellent target specificity.

Alu is classified into one group of SINEs (Short Interspersed Elements). Note that the Alu derived sequence of the functional nucleic acid molecule disclosed in Patent Literature 1 is inserted in a particular orientation and considered to be involved in RNA stability.

On the other hand, it has been reported that some small RNA molecules can also enhance the level of transcription.

CITATION LIST

Patent Literature 1
International Publication WO 2008/113773 A2 (Publication Date: Sep. 25, 2008)
Non Patent Literature 1
He L, Hannon G J. Nat Rev Genet. 2004 July; 5(7):522-31. PMID: 15211354

SUMMARY OF INVENTION

Technical Problem

As widely reported in Patent Literature 1 and other documents, many types of functional nucleic acid molecules that down-regulate gene expression or the like, are well known. Although there have been some techniques for up-regulating gene expression by increasing the transcription efficiency (like in the case of Nature Chemical Biology 3, 166-173 (2007), B. Janowski et al), increasing of the transcription efficiency does not always increase the efficiency of protein synthesis in direct proportion because of the plateau effect. In this regard, the synthesis of translated protein may depend on many other factors, including the ability of a given RNA to interact efficiently with the ribosomes. Additionally, increasing transcription of the natural mRNA is not always possible in the cells or organisms. That is, any functional nucleic acid molecule that increases the protein synthesis efficiency directly has not been reported.

The present inventors consider that there are many conditions in which acting only on translation is desired. For instance, enhancement of translation of an animal protein for therapeutic purposes without interfering with its transcription may be highly desired because it does not require reprogramming of mRNA transcription in the nucleus.

The present invention is accomplished in view of the above problem. An object of the present invention is to provide a functional nucleic acid molecule having a function of increasing the protein synthesis efficiency, and a use of the functional nucleic acid molecule.

Solution to Problem

The present inventors' current knowledge suggested that translation of protein may be regulated by factors including the structure of the regions of the mRNAs that is placed upstream the translated fraction of the mRNAs. This region is known as 5' UTR (5' untranslated region). For the purpose of this invention, the 5' UTR can be a natural one (found in natural RNAs, from the transcription starting site to the protein initiation codon), or can be an artificial sequence, such as the sequence present in a cloning vector or any other recombinant sequence.

The present inventors studied diligently to achieve the above object. Consequently, through analyses of functions of RNA molecules known as non-coding RNAs, the inventors found a surprising fact that a particular structure of such an RNA molecule has a function of increasing the protein synthesis efficiency. This functional nucleic acid exhibited the effect against a specific targeted protein through antisense sequence to a target sequence. Based on the findings, the inventors have accomplished the present invention.

That is, a functional nucleic acid molecule according to the present invention comprises:

(a) a target determinant sequence comprising antisense sequence to a target sequence in the protein-encoding RNA for which protein synthesis efficiency is to be increased; and (b) a regulatory sequence having an activity of increasing of the protein synthesis efficiency.

In the functional nucleic acid molecule according to the present invention, the regulatory sequence comprises a SINE (Short Interspersed Element)-derived sequence. Specifically, SINE-derived sequence may be a tRNA derived SINE, for example SINE B2, ID element, MEN, 4.5S1, DIP-derived sequence, or sequences that comprise joining separate elements of these sequences or similar sequences. SINE-derived sequence may be a sequence which comprises substantially potential predicted structures formed by parts of the SINE sequences, for example.

In the functional nucleic acid molecule according to the present invention, the regulatory sequence may be selected from the group consisting of the following (1) through (5):

(1) an RNA, which is encoded by a DNA consisting of the nucleotide sequence shown in SEQ ID No:1 (SINE/B2 in AS Uchl1)

(2) an RNA, which is encoded by a DNA consisting of the nucleotide sequence shown in SEQ ID No:2 (SINE/B2, 39 nt spacer indicated as underline and SINE/Alu in AS Uchl1)

(3) an RNA, which is encoded by a DNA consisting of the nucleotide sequence shown in SEQ ID No:3 (SINE/B2 in AS Uxt)

(4) nucleic acids (i) which is at least 25% similarity to the RNA, which is encoded by a DNA consisting of the nucleotide sequence shown in SEQ ID No: 1, 2 or 3 and (ii) which has a function of increasing the protein synthesis efficiency; and (5) nucleic acids (i), which is encoded by a DNA in which not less than 1 but not more than 200 nucleotides are deleted, substituted, added, and/or inserted in the nucleotide sequence shown in SEQ ID No: 1, 2 or 3 and (ii) which has a function of increasing the protein synthesis efficiency.

In the functional nucleic acid molecule according to the present invention, the target determinant sequence comprises an antisense sequence to a target sequence in the protein-encoding RNA for which protein synthesis efficiency is to be increased.

In the functional nucleic acid molecule according to the present invention, the target determinant sequence may be located between a 5'-terminal and the regulatory sequence in the functional nucleic acid molecule.

In the functional nucleic acid molecule according to the present invention, it is preferable that the antisense sequence in the target determinant sequence have a length more than 7 nucleotides but less than 250 nucleotides.

In the functional nucleic acid molecule according to the present invention, it is preferable that the antisense sequence in the target determinant sequence be at least 60% similarity to a target sequence in the protein-encoding RNA or to the plasmid sequence upstream of the ATG in the protein-encoding RNA for which protein synthesis efficiency is to be increased.

In the functional nucleic acid molecule according to the present invention, it is preferable that the direction of the SINE-derived sequence which is annotated as forward in the regulatory sequence is oriented in a reverse direction relative to the direction (forward direction as defined above), wherein SINE-derived sequence, is oriented in the same direction of the consensus sequence of SINE. That is, the regulatory sequence of the functional nucleic acid molecule is oriented in a direct direction relative to the direction of translation and reverse orientation relative to the direction of transcription of the antisense nucleic acid molecule.

If the direction from 5' to 3' is defined as the forward direction, the SINE-derived sequence in this invention, wherein its 5' to 3' orientation accords with the SINE consensus sequence, is embedded in the reverse direction of the functional nucleic acid molecule in this invention.

In the functional nucleic acid molecule according to the present invention, the antisense sequence in the target determinant sequence may be designed to hybridize with a target sequence in the 5'-UTR of the protein-encoding RNA for which protein synthesis efficiency is to be increased. Alternatively, the target determinant sequence may be designed to hybridize with a target sequence in the coding region of the protein-encoding RNA for which protein synthesis efficiency is to be increased. In addition, the target determinant sequence may overlap to the sequence of plasmid upstream of the starting codon or including the starting codon in the target sequence of the protein encoding RNA. The functional nucleic acid molecule according to the present invention can be targeted to specific splicing variants at the 5-ends of the protein coding RNA or in other parts of the molecule.

The functional nucleic acid molecule according to the present invention can be appropriately designed and produced by a skilled person in the related art, as long as the functional nucleic acid molecule includes: a target determinant sequence comprising antisense sequence to a target sequence in the protein-encoding RNA for which protein synthesis efficiency is to be increased; and a regulatory sequence having an activity of increasing of the protein synthesis efficiency. Any modification during or post/synthesis can be applied to the functional nucleic acid molecule by a skilled person in the related art according to the know/how in RNA therapeutics or the like.

A DNA molecule according to the present invention encodes any one of the RNA molecules as aforementioned functional nucleic acid molecules.

An expression vector according to the present invention includes any one of the RNA molecules or the DNA molecule as aforementioned functional nucleic acid molecules.

A composition for increasing protein synthesis efficiency according to the present invention comprises any one of the aforementioned functional nucleic acid molecules and/or the aforementioned expression vector.

A method for increasing the protein synthesis efficiency according to the present invention comprises the step of allowing any one of the aforementioned functional nucleic acid molecules or the aforementioned expression vector to coexist with a protein-encoding RNA for which protein synthesis efficiency is to be increased. The protein-encoding RNA is hybridizable with the antisense in the target determinant sequence of the functional nucleic acid molecule.

In the protein synthesis efficiency-increasing method of the present invention, the method may comprise the step of transfecting (or transducing) into a cell any one of the aforementioned functional nucleic acid molecules or the aforementioned expression vector.

A protein synthesis method according to the present invention is a method for synthesizing a protein, comprising the step of increasing the protein synthesis efficiency by any one of the aforementioned protein synthesis efficiency-increasing methods.

A method for treating a disease according to the present invention, wherein the disease is caused by a quantitative decrease in a predetermined normal protein or haploinsufficiency, comprises the step of increasing the protein synthesis efficiency in a subject by any one of the aforementioned protein synthesis efficiency-increasing methods.

In the treatment method according to the present invention, the subject may have a disease or a predisposition to the disease, wherein the disease is caused by a quantitative decrease in a predetermined normal protein or haploinsufficiency. Furthermore, the functional nucleic acid molecule may increase the efficiency of synthesizing of the predetermined normal protein.

Further, in case that the disease is caused by a quantitative decrease in a predetermined normal protein or haploinsufficiency, and caused by a quantitative increase of another protein including an abnormal protein like mutant protein, the treatment method of the present invention can be used in combination with a conventional method for suppressing the expression of the another protein by siRNA, shRNA, or the like, and/or a conventional method for inactivating a function of a protein by use of an antibody, a low-molecular-weight compound, or the like, as appropriate.

Further, in the treatment method according to the present invention, the disease may be a neurodegenerative disease or cancer, for example.

Advantageous Effects of Invention

According to the present invention, it is successfully possible to provide (a) a functional nucleic acid molecule having a function of increasing the protein synthesis efficiency and (b) a use of the functional nucleic acid molecule.

BRIEF DESCRIPTION OF DRAWINGS

FIG. 1, related to the experiment 1, is a schematic diagram of Uchl1/AS Uchl1 genomic organization. Uchl1 exons are in black; 3' and 5' UTRs in white.

FIG. 7, related to the experiment7, is a view showing Family of AS transcripts with embedded SINEB2. Family of FANTOM 3 non-coding clones that are AS to protein coding genes and contain embedded SINEB2 in inverted orientation.

FIG. 14, related to the experiment14, is a view showing an artificial AS transcript with embedded SINEB2 (AS Gfp) to an artificial humanized enhanced Green Fluorescent Protein (Gfp) mRNA increases GFP protein synthesis: (a) of FIG. 14 shows Schematic diagram of Gfp/AS Gfp constructs, (b) of FIG. 14 shows how AS Gfp increases Gfp protein levels in transfected HEK cells while a scramble overlapping sequence or an empty plasmid does not increases Gfp protein levels in transfected HEK cells. The overlap is 72 nt long and it is centered on the ATG.

DESCRIPTION OF EMBODIMENTS

Figure 2:
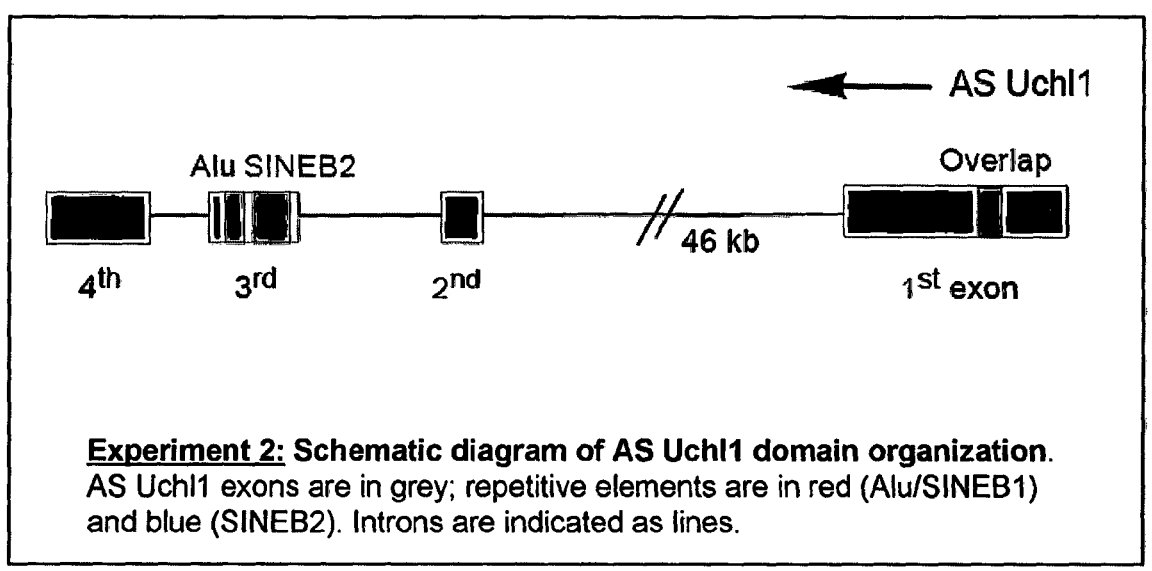
FIG. 2, related to the experiment2, is a schematic diagram of AS Uchl1 domain organization. AS Uchl1 exons are in grey; repetitive elements are in red (Alu/SINEB1) and blue (SINEB2). Introns are indicated as lines.
Figure 3:
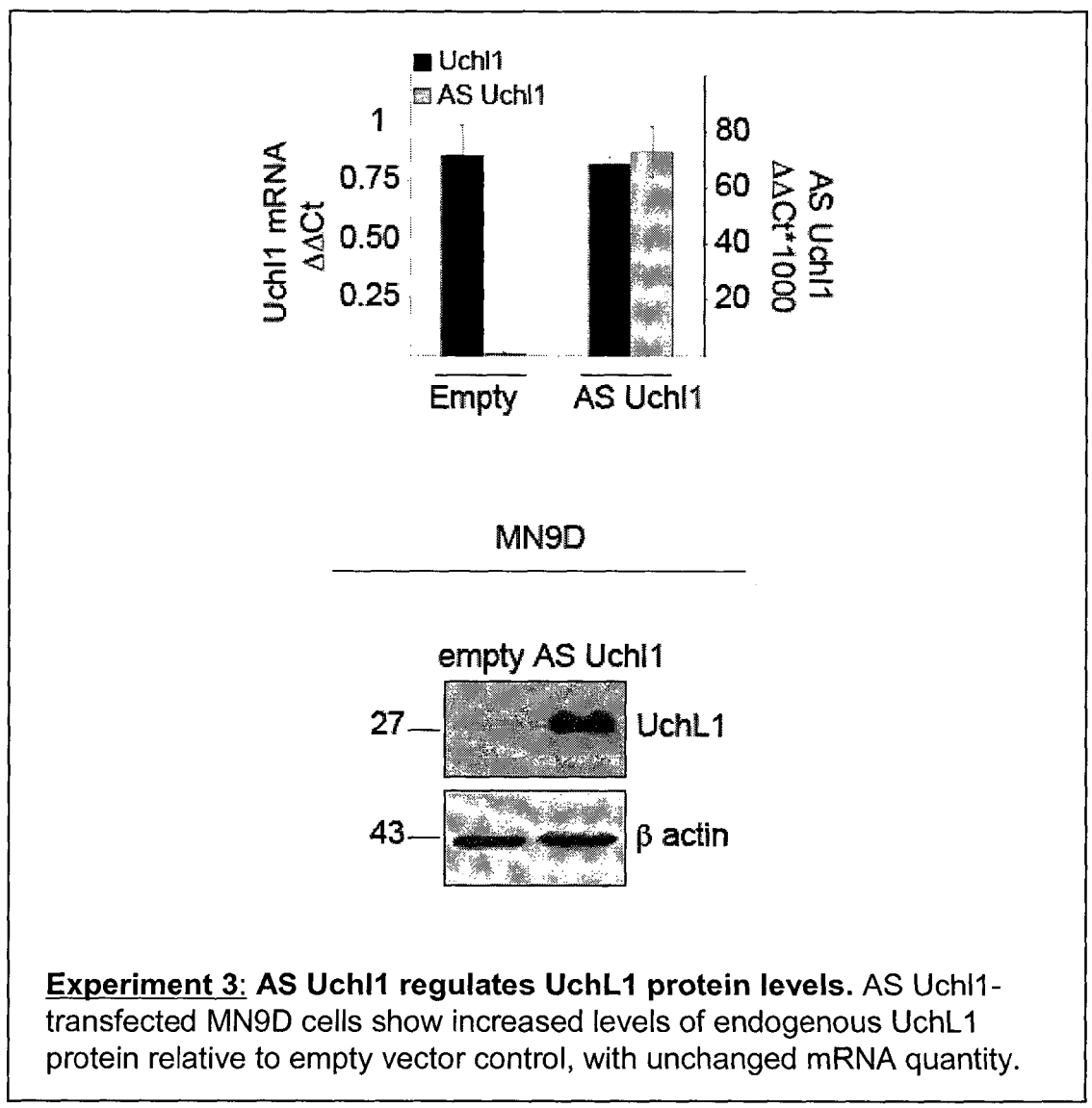
FIG. 3, related to the experiment3, is a view showing AS Uchl1 regulates UchL1 protein levels. AS Uchl1-transfected MN9D cells show increased levels of endogenous UchL1 protein relative to empty vector control, with unchanged mRNA quantity.
Figure 4:
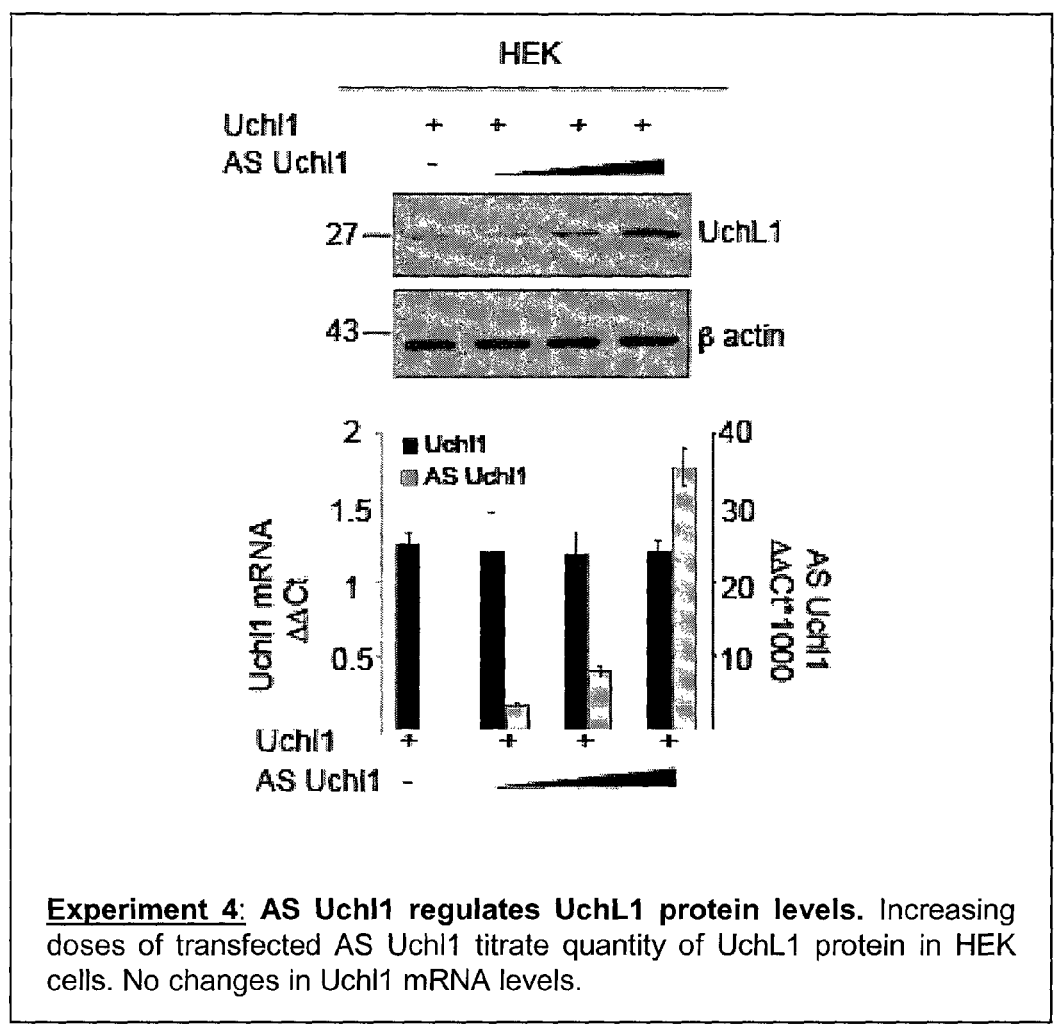
FIG. 4, related to the experiment4, is a view showing AS Uchl1 regulates UchL1 protein levels. Increasing doses of transfected AS Uchl1 titrate quantity of UchL1 protein in HEK cells. No changes in Uchl1 mRNA levels.
Figure 5:
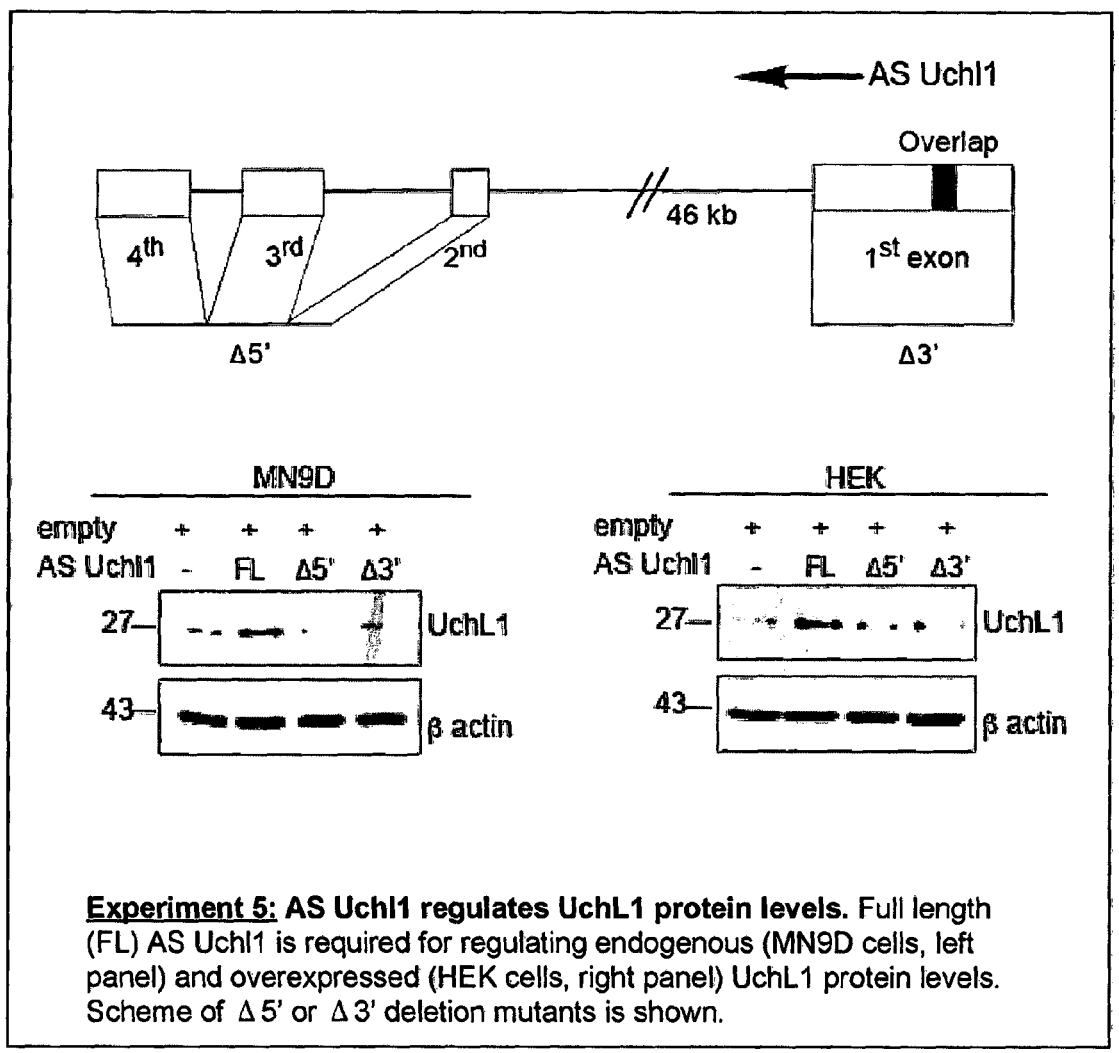
FIG. 5, related to the experiment5, is a view showing AS Uchl1 regulates UchL1 protein levels. Full length (FL) AS Uchl1 is required for regulating endogenous (MN9D cells, left panel) and overexpressed (HEK cells, right panel) UchL1 protein levels. Scheme of Δ5' or Δ3' deletion mutants is shown.
Figure 6:
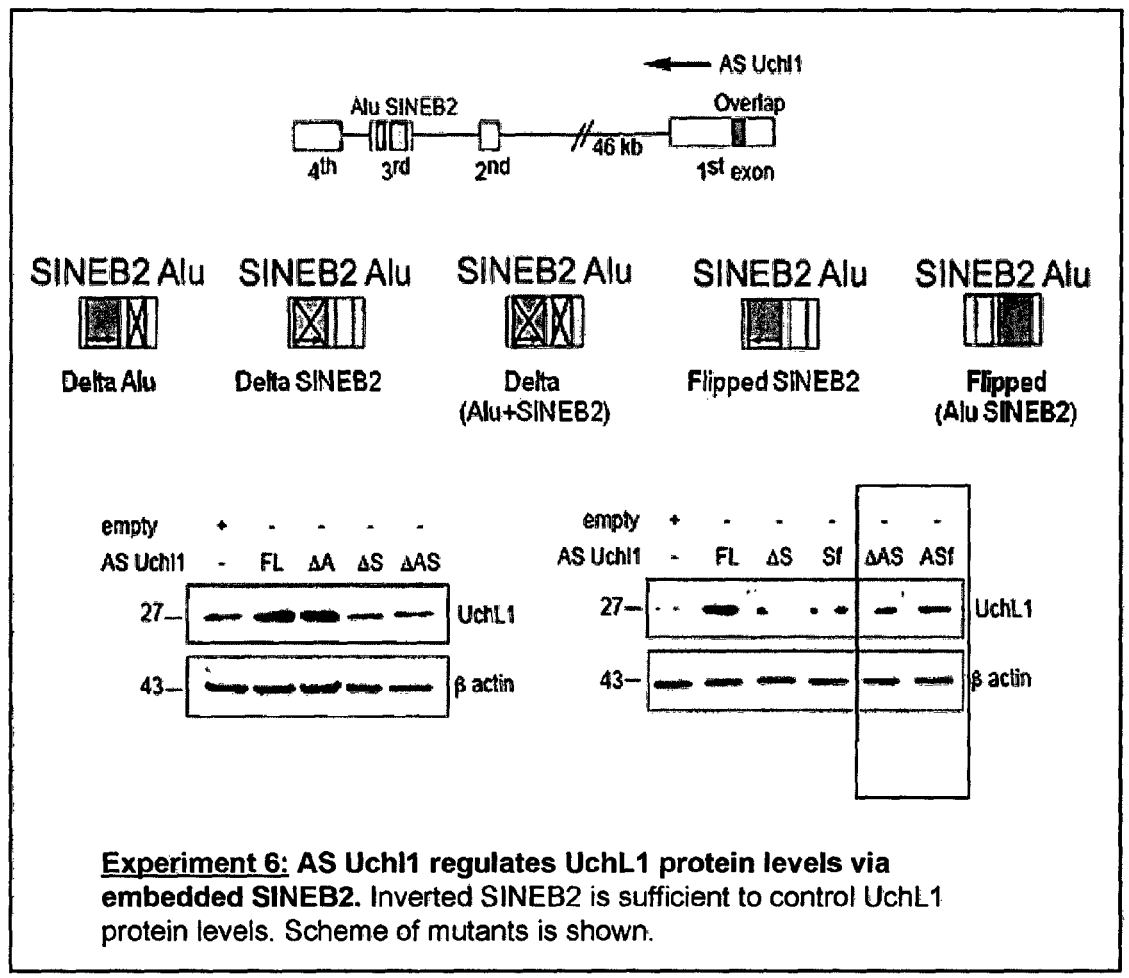
FIG. 6, related to the experiment6, is a view showing AS Uchl1 regulates UchL1 protein levels via embedded SINEB2. Inverted SINEB2 is sufficient to control UchL1 protein levels. Scheme of mutants is shown.
Figure 8:
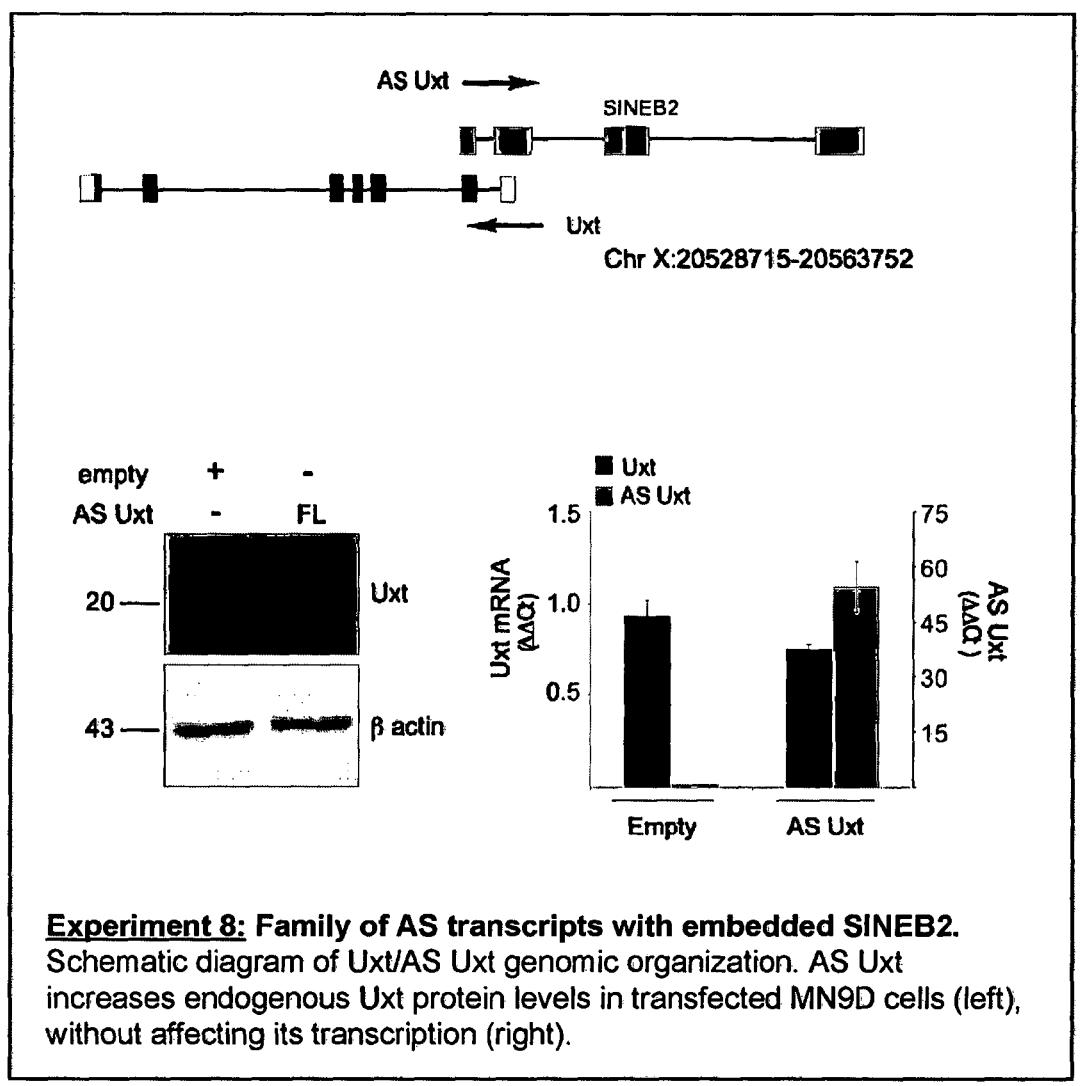
FIG. 8, related to the experiment8, is a view showing Family of AS transcripts with embedded SINEB2. Schematic diagram of Uxt/AS Uxt genomic organization. AS Uxt increases endogenous Uxt protein levels in transfected MN9D cells (left), without affecting its transcription (right).
Figure 9:
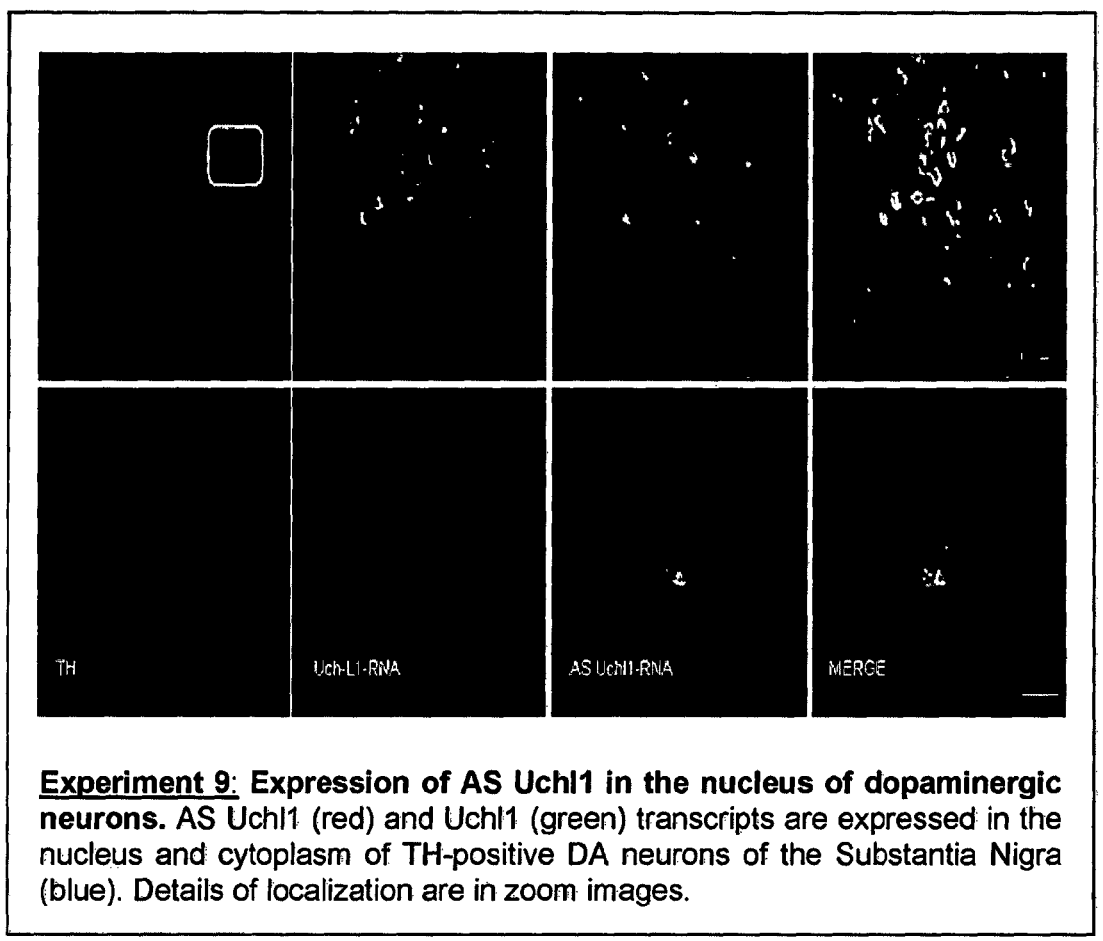
FIG. 9, related to the experiment 9, is a view showing Expression of AS Uchl1 in the nucleus of dopaminergic neurons. AS Uchl1 (red) and Uchl1 (green) transcripts are expressed in the nucleus and cytoplasm of TH-positive DA neurons of the Substantia Nigra (blue). Details of localization are in zoom images.
Figure 10:
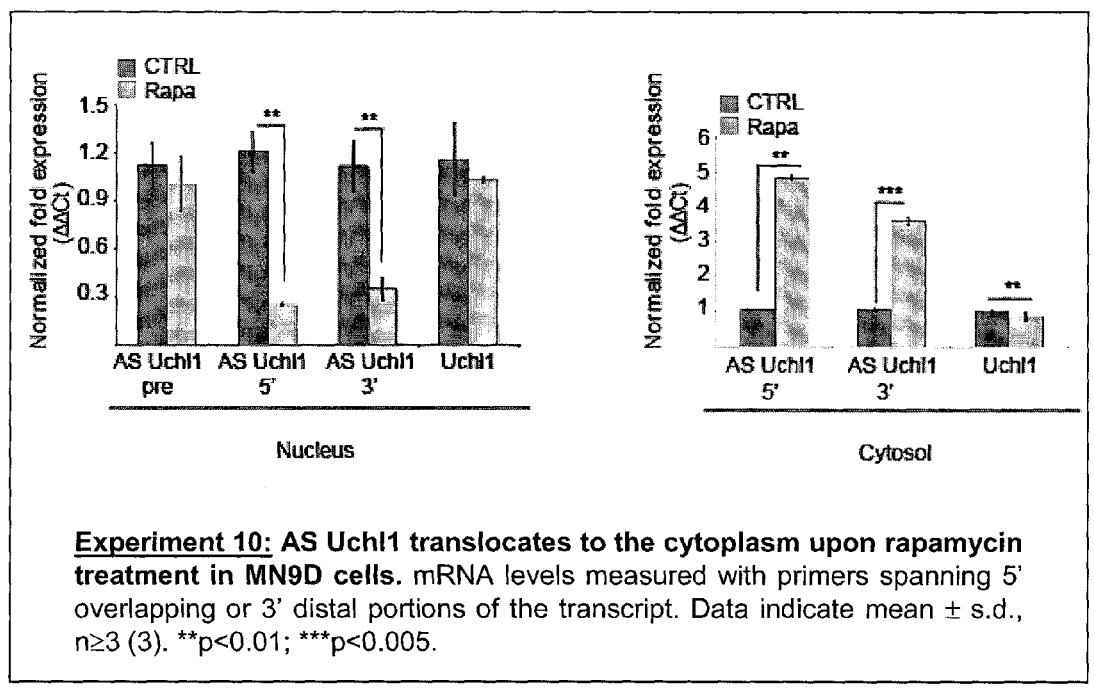
FIG. 10, related to the experiment10, is a view showing AS Uchl1 translocates to the cytoplasm upon rapamycin treatment in MN9D cells. mRNA levels measured with primers spanning 5' overlapping or 3' distal portions of the transcript. Data indicate mean±s.d., n≥3 (3). p<0.01; *p<0.005.
Figure 11:
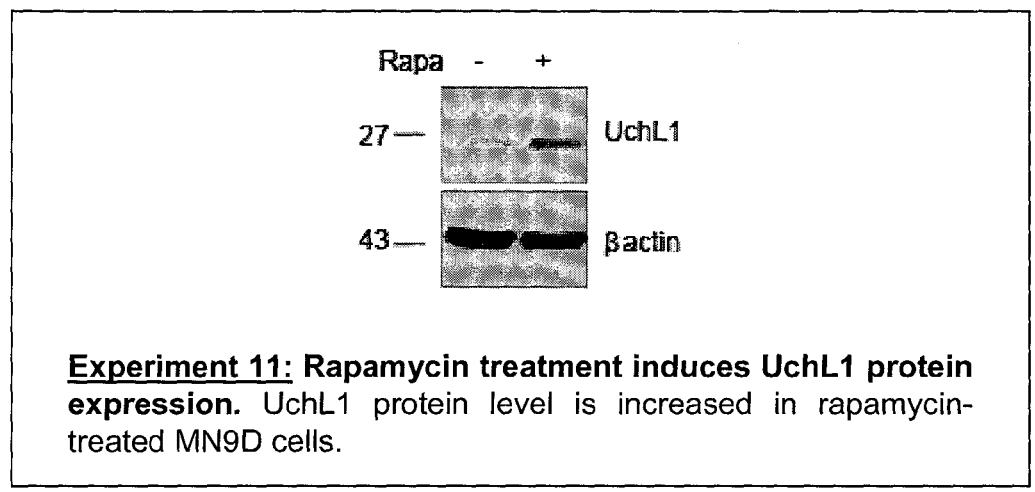
FIG. 11, related to the experiment11, is a view showing Rapamycin treatment induces UchL1 protein expression. UchL1 protein level is increased in rapamycin-treated MN9D cells.
Figure 12:
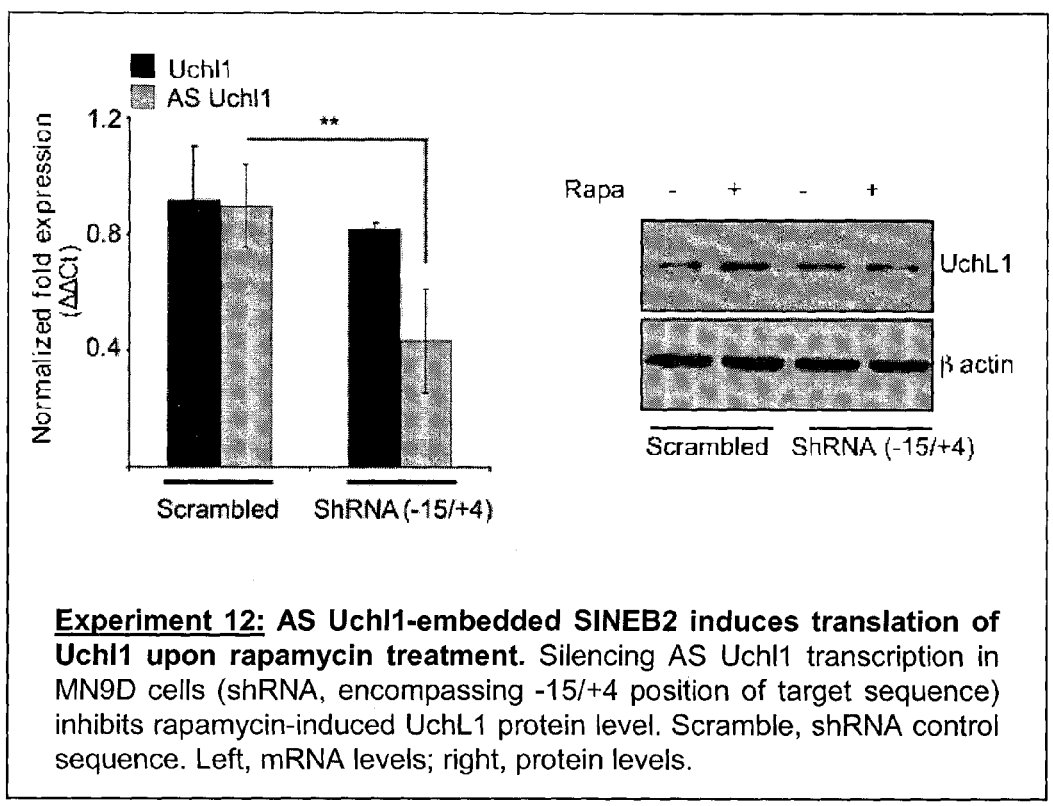
FIG. 12, related to the experiment12, is a view showing AS Uchl1-embedded SINEB2 induces translation of Uchl1 upon rapamycin treatment. Silencing AS Uchl1 transcription in MN9D cells (shRNA, encompassing −15/+4 position of target sequence) inhibits rapamycin-induced UchL1 protein level. Scramble, shRNA regulatory sequence. Left, mRNA levels; right, protein levels.
Figure 13:
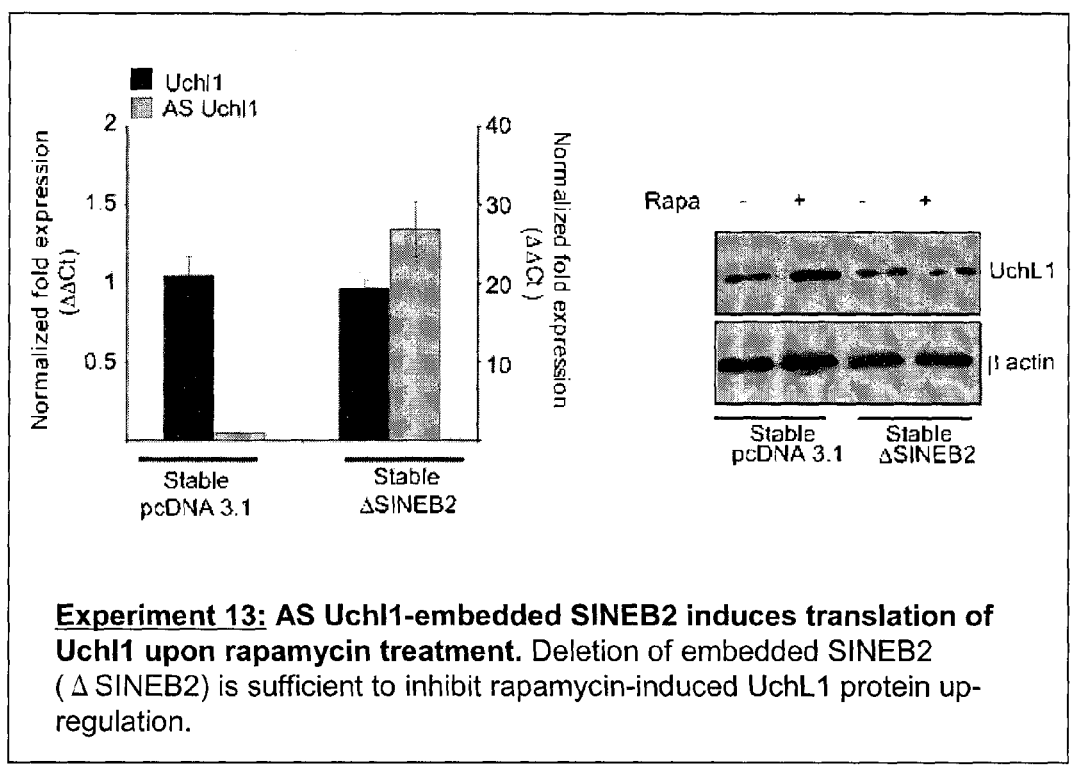
FIG. 13, related to the experiment13, is a view showing AS Uchl1-embedded SINEB2 induces translation of Uchl1 upon rapamycin treatment. Deletion of embedded SINEB2 (ΔSINEB2) is sufficient to inhibit rapamycin-induced UchL1 protein up-regulation.

The following describes an embodiment of the present invention, more specifically.

[1. Functional RNA Molecule]

(Constitution of Functional Nucleic Acid Molecule)

A functional nucleic acid molecule according to the present invention has a feature that it comprises: a target determinant sequence comprising an antisense sequence to a target sequence in the protein-encoding RNA for which protein synthesis efficiency is to be increased; and a regulatory sequence having an activity of increasing of the protein synthesis efficiency. The functional nucleic acid molecule according to the present invention can be appropriately designed and produced by a skilled person in the related art based on the description herein.

The protein synthesis efficiency is increased according to the present invention. In one embodiment, the protein synthesis efficiency is increased as a result of increase in the translation efficiency, preferably, without changing the transcription efficiency substantially. Thus, the protein synthesis efficiency may be increased by increasing the translation efficiency. In another embodiment, both transcription and translation can be increased by independent means; obviously, it may be the case that an RNA may result lower expression level, and yet the protein results higher expression level.

(Protein-Encoding RNA for which Protein Synthesis Efficiency is to be Increased)

The protein-encoding RNA for which protein synthesis efficiency is to be increased by the functional nucleic acid molecule according to the present invention is not especially limited in regard to its sequence, origin, and the like, provided that the RNA comprises a translation domain (coding region) having a 5'-terminal start codon and a 3'-terminal stop codon. Specifically, the protein-encoding RNA for which protein synthesis efficiency (the target RNA) is to be increased by the functional nucleic acid molecule according to the present invention may further have a 5'-cap structure, a 5' untranslated region (5'-UTR) and/or a 3' untranslated region. These regions may be derived from endogenous sequence in a cell or artificially synthesized sequence. The ORFeome, in which Open Reading Frames (coding sequences) of genes are placed in expression vectors, is one of the examples.

Further, it is preferable that the 3' untranslated region includes, at its 3' terminal, a sequence (poly-A addition signal) so that a poly-A sequence can be added. The poly-A addition signal may be, for example, a nucleotide sequence consisting of AAUAAA, a SV40 early poly-A signal having two sequences of AAUAAA, a sequence in which SV40 early poly-A signals are aligned in a tandem manner, or the like. The poly-A addition signal is not limited to them. As examples, various alternative polyadenylation sites have been described in the literature, and some mRNA do not even carry conventional polyadenylation signals (Carninci et al, Genome Res. 2003 June; 13(6B):1273-89. PMID: 12819125).

The protein-encoding RNA for which protein synthesis efficiency is to be increased according to the present invention may have a poly-A sequence at its 3' terminal. An RNA having a poly-A sequence at its 3' terminal has excellent protein synthesis efficiency from a translation domain and excellent stability of the RNA itself. Such an RNA may be, for example, any one of RNAs shown in Uchl1, Uxt, GFP or a homologue of any one of these RNAs, although such an RNA is not limited to them.

*Mus musculus* ubiquitin carboxy-terminal hydrolase L1 (Uchl1) RefSeq: NM_011670.2
The Uchl1 DNA sequence which encodes the Uchl1 RNA is shown in SEQ ID NO.4.
*Mus musculus* ubiquitously expressed transcript (Uxt) RefSeq: NM_013840.3
The Uxt DNA sequence which encodes the Uxt RNA is shown in SEQ ID NO.5.
GFP (Sequence from pEGFP vector)
The GFP DNA sequence which encodes the GFP RNA sequence is shown in SEQ ID NO.6.

The protein-encoding RNA for which protein synthesis efficiency is to be increased may be endogenous RNA of biological origin (for example, mRNA) or artificially synthesized. Further, mRNA derived from eucaryotes encompass mature mRNA that has been subjected to what is called processing, and precursor mRNA that has not been subjected to processing.

(Target Determinant Sequence)

The target determinant sequence is a sequence that comprises an antisense sequence to a target sequence in the protein-encoding RNA for which protein synthesis efficiency is to be increased. A target sequence is arbitrarily, selected from a partial sequence of protein-encoding RNA for which protein synthesis efficiency is to be increased in the present invention. A target sequence may derive from the RNA sequence transcribed from the plasmid DNA in which the protein-encoding cDNA is inserted and around the first 5'-terminal start codon. A length of the antisense sequence is not especially limited. However, from the viewpoint of increasing specificity for a target RNA in a system including different RNAs, the antisense sequence may have a length of preferably more than 7 nucleotides, more preferably 10, more preferably 15. Furthermore, the antisense sequence may have a length of preferably less than 250 nucleotides, more preferably 200, more preferably 150, more preferably 100, more preferably 90, more preferably 80, more preferably 77 nucleotides, more preferably 70 nucleotides, more preferably 60 nucleotides, more preferably 50 nucleotides, more preferably 40 nucleotides, more preferably 30 nucleotides.

In one embodiment, more than one different antisense sequences can be included in the target determinant sequence. These multiple antisense sequences can be applied to targeting of multiple proteins, for example. Alternatively, the multiple antisense sequences can be applied to improving the specificity to a protein-encoding RNA wherein the multiple antisense sequences are hybridizable with the same protein-encoding. RNA. In one embodiment, the target determinant sequence of the present invention may contain mismatches against the target RNA on purpose to prevent the reaction of gamma interferon that may take place in the cells in presented of long double strand nucleic acids molecule, like long double strand RNAs.

Further, from the viewpoint of increasing specificity between the functional nucleic acid molecule of the present invention and the target RNA, the antisense sequence in a target determinant sequence is designed to be preferably at least 60% similarity, more preferably at least 65% similarity, more preferably at least 70% similarity, more preferably at least 75% similarity, more preferably at least 80% similarity, more preferably at least 85% similarity, more preferably at least 90% similarity, more preferably at least 95% similarity to a corresponding target sequence in the protein-encoding RNA for which protein synthesis efficiency is to be increased, as long as the antisense sequence can hybridize to the target sequence in the protein-encoding RNA and/or to the plasmid-derived RNA that contains the target sequence. It is specifically preferable that the antisense sequence in the target determinant sequence be designed to be thoroughly identical with the corresponding sequence of the target sequence.

Further, an antisense sequence in a target determinant sequence can be designed to hybridize with a 5'-UTR of the protein-encoding RNA for which protein synthesis efficiency is to be increased. This design can be applied to the synthesizing full length encoded-protein. 5'-UTR may be derived from endogenous sequence in a cell or artificial sequence. The antisense sequence in the target determinant sequence may be designed to be hybridizable with other regions, except the 5'-UTR, of the target RNA, such as a coding region of the target RNA. For example, the antisense sequence in the target determinant sequence can be designed to be hybridizable with a given part of the coding region of the target RNA. This design is useful for a dystrophin gene or the like in which a protein to be encoded by an RNA is very large and has a domain that exhibits bioactivity by itself.

Additionally, the antisense sequence in the target determinant sequence can be designed to hybridize both the 5' UTR and a part of the other functional part of the sequence, like the coding sequence or the 3' UTRs of the protein coding mRNAs.

(Regulatory Sequence)

In the functional nucleic acid molecule according to the present invention, the regulatory sequence has an activity of increasing of the protein synthesis efficiency.

In one embodiment of the invention, the regulatory sequence may comprise a SINE-derived sequence. Specifically, SINE-derived sequence may be a tRNA-derived SINE, for example SINE-B2, ID element, MEN, 4.5S1, DIP-derived sequence. Additionally, 7SL-RNA-derived sequence such as Alu may be comprised in the regulatory sequence.

In one embodiment, multiple SINE-derived sequences can be included in the regulatory sequence. These multiple SINE-derived sequences may be with combination of different sequences, for example a combination of SINE B2-derived sequence and Alu-derived sequence or a combination of different SINE B2-derived sequence.

The SINE-derived sequence indicates a sequence entirely or partially identical with or similar to the consensus sequence of each species of SINE. For example, the SINE-B2-derived sequence indicates a sequence entirely or partially identical with or similar to the consensus sequence of a SINE B2. Even a truncated SINE derived sequence against the consensus sequence of SINE can be used as the SINE derived sequence in the present invention as long as a function of increasing the protein synthesize efficiency is kept. SINE-derived sequence may be a sequence which comprises substantially potential predicted structures formed by parts of the SINE sequences, for example. The examples of the potential predicted structures of SINE B2-derived sequence are as shown in (a) and (b) of FIG. 16.

The similar sequence indicates a sequence that is at least 25% similarity, preferably at least 50% similarity, more preferably at least 55% similarity, more preferably at least 60% similarity, more preferably at least 65% similarity, more preferably at least 70% similarity, more preferably at least 75% similarity, more preferably at least 80% similarity, more preferably at least 85% similarity, more preferably at least 90% similarity, more preferably at least 95% similarity to the consensus sequence of the SINE.

The sequence of a SINE may deviate from these conservative consensus described above. For instance, the analysis of the consensus similarity between the SINE B2 sequences of three sequences alone, the SINE B2 fraction of SEQ ID NO:1, SEQ ID NO:3, and another SINE B2 randomly taken from the literature (reference: Espinosa et al, http://rnajournal.cshlp.org/content/13/4/583.full), clearly indicates that the SINE B2 fractions alone can share as little as 9 bases out of 36, with only 25% of similarity.

Yet, despite diverging, these are still recognizable as a SINE B2 element using programs like RepeatMask as published (Bioinformatics. 2000 November; 16(11):1040-1. MaskerAid: a performance enhancement to RepeatMasker. Bedell J A, Korf I, Gish W.).

In one embodiment, the length can be limited to the shortest sequences with similarity to SINE elements, which are capable to cause increased the efficiency of protein synthesis.

In one embodiment, it is possible to synthesize artificial nucleic acid sequences that have partial similarity to the SINE elements described in the present invention and act to increase the level of synthesized protein.

Further, the functional nucleic acid molecule according to the present invention may include a plurality of regulatory sequences aligned in a tandem manner, for the purpose of further promoting the protein synthesis efficiency.

In the description of the present invention, "SINE" broadly indicates, among non-LTR (long terminal repeat) retrotransposon, an interspersed repetitive sequence (a) which encodes a protein having neither reverse-transcription activity nor endonuclease activity or the like and (b) whose complete or incomplete copy sequences exist abundantly in genomes of living organisms. That is, SINE is a DNA sequence that is inserted into a genome through the reverse transcription from RNA to cDNA, depending on other host factors in these processes. A length of the SINE is not especially limited, but generally, in a range of not less than 20 bp, preferably not less than 30 bp, more preferably not less than 50 bp, more preferably not less than 50 bp, but not more than 700 bp, preferably not more than 600 bp, more preferably not more than 500 bp, more preferably not more than 400 bp. Further, the origin of SINE is not limited, but is generally derived from tRNA and has a sequence having a sequence corresponding to the tRNA on its 5'-terminal side. Further, the SINE may be a 7SL RNA-derived sequence such as Alu, and a 5S rRNA-derived sequence such as SINE 3. In regard to the SINE 3, the document by Kapitonov et al (Vladimir V. Kapitonov and Jerzy Jurka Molecular Biology AND Evolution 20(5): p694-702, 2003) and the like document can be referred to.

The regulatory sequence may be, for example, selected from the following (1) to (5):

(1) an RNA, which is encoded by a DNA consisting of the nucleotide sequence shown in SEQ ID No:1

(2) an RNA, which is encoded by a DNA consisting of the nucleotide sequence shown in SEQ ID No:2

(3) an RNA, which is encoded by a DNA consisting of the nucleotide sequence shown in SEQ ID No:3

(4) nucleic acids (i) which is at least 25% similarity to the RNA, which is encoded by a DNA consisting of the nucleotide sequence shown in SEQ ID No: 1, 2 or 3 and (ii) which has a function of increasing the protein synthesis efficiency; and (5) nucleic acids (i), which is encoded by an DNA in which not less than 1 but not more than 200 nucleotides are deleted, substituted, added, and/or inserted in the nucleotide sequence shown in SEQ ID No: 1, 2 or 3 and (ii) which has a function of increasing the protein synthesis efficiency.

The number of nucleotides to be deleted, substituted, added, and/or inserted is preferably not less than 1 but not more than 175, more preferably not less than 1 but not more than 150, more preferably not less than 1 but not more than 125, more preferably not less than 1 but not more than 100, more preferably not less than 1 but not more than 75, more preferably not less than 1 but not more than 50, more preferably not less than 1 but not more than 30, more preferably not less than 1 but not more than 20.

(Positional Relationship Between Target Determinant Sequence and Regulatory Sequence)

In the present invention, a direction (a sense-strand direction) along which a target protein is translated is defined as "forward direction", and the direction opposite to the forward direction is defined as "reverse direction". In the functional nucleic acid molecule according to the present invention, a positional relationship between the target determinant sequence and the regulatory sequence is not especially limited. However, it is preferable that the target determinant sequence be located closer to a forward-direction side in the functional nucleic acid molecule than the regulatory sequence. The target determinant sequence may be directly linked to the regulatory sequence. Alternatively, a linker sequence and/or the like sequence for connecting the target determinant sequence and the regulatory sequence may be inserted there between.

In the functional nucleic acid molecule according to the present invention, it is preferable that the direction of the SINE-derived sequence which is annotated as forward in the regulatory sequence is oriented in a reverse direction relative to the direction (forward direction as defined above), wherein SINE-derived sequence is oriented in the same direction of the consensus sequence of SINE. That is, the regulatory sequence of the functional nucleic acid molecule is oriented in a forward direction relative to the direction of translation.

If the direction from 5' to 3' is defined as the forward direction, the SINE-derived sequence in this invention, wherein its 5' to 3' orientation accords with the SINE consensus sequence, is embedded in the reverse direction of the functional nucleic acid molecule in this invention. For example, in case of one of SINE B2-derived sequence, Abox site of SINE B2-derived sequence is located on the 3' side of the functional nucleic acid molecule compared to Bbox site of SINE B2-derived sequence.

(Production of Functional Nucleic Acid Molecule)

A method according to the present invention for producing a functional nucleic acid molecule comprises the step of preparing the aforementioned RNA molecule. The functional nucleic acid molecules may be prepared by a well-known nucleic acid biosynthesis method, or such a method that (i) a DNA molecule encoding the functional RNA molecule is produced and (ii) the DNA molecule is transcribed into the functional RNA molecule, for example. A size of the functional nucleic acid molecule is not especially limited, but the functional nucleic acid molecule has a size of preferably not more than 2000 nucleotides, more preferably not more than 250 nucleotides, for example, from the viewpoint of producing the functional nucleic acid molecule by the nucleic acid biosynthesis method.

[2. DNA Molecule, Expression Vector, Composition for Increasing Protein Synthesis Efficiency]

A DNA molecule according to the present invention encodes any one of the aforementioned functional nucleic acid molecules according to the present invention. Further, an expression vector according to the present invention is an RNA vector comprising any one of the aforementioned functional RNA molecules of the present invention or a DNA vector comprising the DNA molecule according to the present invention. Further, a composition for increasing protein synthesis efficiency according to the present invention comprises any one of the aforementioned functional nucleic acid molecules or the aforementioned expression vector.

In one embodiment, the composition according to the present invention may comprise a translation agent based on in vitro system like reticulocyte extract to produce protein in vitro; or to produce protein in vivo in mammalian cells expressing a protein for industrial use, for research purpose, or for any other screening, for example.

The backbone of the expression vector according to the present invention is not especially limited to any particular type, and may be appropriately selected from a plasmid vector. The plasmid vector may be a mammalian, yeast, insect expression vector, a virus vector (for example a lentiviral or retroviral expression vector, adenovirus or adeno-associated virus vectors), a phage vector, a cosmid vector, and the like, depending on types of host cells to be used and the purpose of use. For example, in a case where the present invention is used for gene treatment of mammals including a human, the present invention may be prepared in a form of a virus vector, such as an adenovirus or adeno-associated vector or a lentivirus vector.

Alternatively, the expression vector may ultimately be integrated in the genome of the expressing cells or organism to be targeted.

[3. Method for Increasing Protein Synthesis Efficiency]
(Method for Increasing Protein Synthesis Efficiency)

A method for increasing protein synthesis efficiency according to the present invention comprises the step of allowing a functional nucleic acid molecule according to the present invention or the aforementioned expression vector to coexist with a protein-encoding RNA for which protein synthesis efficiency is to be increased. This step can be carried out in vivo or in vitro using, for example, cell-free protein synthesis system. In the present invention, "in vivo" means a system of using either cell culture or whole animal specifically, and "in vitro" means a system using cell-free assay specifically. In a case where the step is carried out in vivo, the functional nucleic acid molecule or the aforementioned expression vector may be allowed to coexist, in an isolated cell or tissue, with a protein-encoding RNA for which protein synthesis efficiency is to be increased. Alternatively, the functional nucleic acid molecule or the aforementioned expression vector may be allowed to coexist, in a living organism, with an RNA for which protein synthesis efficiency is to be increased.

The method for increasing protein synthesis efficiency according to the present invention may comprise transfecting into a cell an aforementioned expression vector encoding the functional nucleic acid molecule or the functional nucleic acid molecule itself so as to allow the functional nucleic acid molecule to coexist with the protein-encoding RNA. The "cell" indicates not only an isolated cell but also cells constituting an individual. The RNA for which protein synthesis efficiency is to be increased may be derived from an endogenous sequence in a cell or an RNA encoding a protein synthesized artificially. The transfection (or gene induction) of a nucleic acid molecule into a cell may be carried out appropriately by conventional methods, for example, self-infection by a vector, a microinjection technique, a lipofection technique, an electroporation technique, a calcium phosphate method, transduction of a virus and the like. The vector may or may not be permanently integrated in the host genome.

The cells may be derived from any one of cells from any organism including animals and plants, or any one of cells selected from the established cell lines.

In the present invention, animals include vertebrate, preferably mammals including a human, but are not limited to these examples.

In the present invention, plants include both monocotyledons and dicotyledons. In one embodiment, the plants are crop plants (for example, cereals and pulses, maize, wheat, potatoes, tapioca, rice, *sorghum*, millet, cassava, barley, or pea), or other legumes. In another embodiment, the plants may be vegetables or ornamental plants. The plants of the invention may be: corn (*Zea mays*), canola (*Brassica napus, Brassica rapa* ssp.), flax (*Linum usitatissimum*), alfalfa (*Medicago sativa*), rice (*Oryza sativa*), rye (*Secale cerale*), sorghum (*Sorghum bicolour, Sorghum vulgare*), sunflower (*Helianthus annus*), wheat (*Tritium aestivum*), soybean (*Glycine max*), tobacco (*Nicotiana tabacum*), potato, (*Solanum tuberosum*), peanuts (*Arachis hypogaea*), cotton (*Gossypium hirsutum*), sweet potato (*Lopmoea batatus*), cassava (*Manihot esculenta*), coffee (*Cofea* spp.), coconut (*Cocos nucifera*), pineapple (*Anana comosus*), citris tree (*Citrus* spp.), cocoa (*Theobroma cacao*), tea (*Camellia senensis*), banana (*Musa* spp.), avocado (*Persea americana*), fig (*Ficus casica*), guava (*Psidium guajava*), mango, (*Mangifer indica*), olive (*Olea europaea*), papaya (*Carica papaya*), cashew (*Anacardium occidentale*), macadamia (*Macadamia intergrifolia*), almond (*Prunus amygdalus*), sugar beets (*Beta vulgaris*), oats, or barley, but are not limited to these examples.

In the present invention, the established cell lines including mammalian derived cell such as COS-1 (ATCC No. CRL 1650), COS-7 (ATCC CRL 1651), human embryonic kidney line 293 (ATCC NO. CRL 1573), PerC6 (Crucell), baby hamster kidney cell (BHK) (ATCC CRL. 1632), BHK570 (ATCC NO: CRL 10314), Chinese hamster ovary cells CHO (e.g. CHO-K1, ATCC NO: CCL 61, DHFR minus CHO cell line such as DG44, particularly those CHO cell lines adapted for suspension culture, mouse Sertoli cell, monkey kidney cell, African green monkey kidney cell (ATCC CRL-1587), HeLa cell, SH-Y5Y cell, canine kidney cell (ATCC CCL 34), human lung cell (ATCC CCL 75), Hep G2 and myeloma or lymphoma cells e.g. NSO (see U.S. Pat. No. 5,807,715), Sp2/0, YO, other animals derived cells such as Sf9 cell, DT40, but are not limited to these examples. Furthermore, the established cell lines can be hybridoma or a cell given a particular feature by gene transfer, nuclear transfer and/or treatment of chemical compound, for example a nuclear transfer embryonic stem cell or an iPS cell (WO2007/069666, JP-A 2010-273680, JP-A 2010-284088, JP-A 2011-50379, JP-A 2011-4674, etc), a neuronal cell differentiated from neural stem cell, iPS cell or the like, or neuronal cells derived from re-programmed fibroblasts or the like, but are not limited to these examples.

The protein synthesis efficiency increasing method according to the present invention optimally contributes to increase the efficiency of the translation from RNA. The increase of the protein synthesis efficiency indicates that the protein synthesis efficiency is increased as compared with a case where the functional nucleic acid molecule according to the present invention or aforementioned expression vector is not allowed to coexist with the target RNA in a system. How much the protein synthesis efficiency is to be increased is not limited especially. However, it is preferable that an amount of a protein to be synthesized by the protein synthesis efficiency-increasing method be at least 1.5 times, more preferably at least 2 times more than an amount of a protein to be produced in the case where the functional RNA molecule is not allowed to coexist with the target RNA in the system.

In a case where the functional nucleic acid molecule or aforementioned expression vector is allowed to coexist with the target RNA in the system, a quantitative ratio between the functional nucleic acid molecule (or the expression vector) and the target RNA is not especially limited. The quantitative ratio between them may be, for example, 1:1 to 1:10.

(Method for Synthesizing Protein)

The aforementioned protein synthesis efficiency-increasing method according to the present invention can be used as a protein synthesis method. That is, a protein synthesis method according to the present invention is a method for producing a target protein, comprising the step of increasing the protein synthesis efficiency by any one of the aforementioned protein synthesis efficiency-increasing methods. It is preferable that the protein synthesis method allow for efficient synthesis of the target protein through the increasing the efficiency of protein translation from the target RNA.

In the protein synthesis method of the present invention, one example of the protein to be synthesized is an antibody, particularly synthesizing a light or a heavy chain or both of the antibody or single chain recombinant version of an antibody. The synthesis of the antibody is carried out preferably in an in vitro system or in an isolated cell system so that a functional nucleic acid molecule according to the present invention or aforementioned expression vector can be allowed to coexist, in the system, with a target RNA for which protein synthesis efficiency is to be increased.

(Method for Treating Disease)

The protein synthesis efficiency-increasing method according to the present invention can be used for treatment of a disease caused by a quantitative decrease in a predetermined normal protein, for example. The disease is not especially limited, but may be, for example; myodegeneration such as muscular dystrophy; neurodegenerative disease such as Alzheimer's disease, Parkinson's disease, Amyotrophic Lateral Sclerosis, and triplet repeat diseases both at the protein encoding level (i.e. Huntington's disease) or at DNA/RNA level (i.e. Fragile X).

Furthermore, a tumor can be also applied to the present invention through the increase of expression of a pro-apoptotic protein or a tumor suppression protein for tumor treatment as for instance for p53 family members.

Such a tumor, including a cancer, may be any one of tumors including without limitation carcinoma, melanoma and sarcoma, bladder carcinoma, brain tumor, breast tumor, cervical tumor, colorectal tumor, esophageal tumor, endometrial tumor, hepatocellular carcinoma, gastrointestinal stromal tumor, laryngeal tumor, lung tumor, osteosarcoma, ovarian tumor, pancreatic tumor, prostate tumor, renal cell carcinoma, skin tumor, or thyroid tumor.

The treatment method comprises the step of increasing the protein synthesis efficiency by the aforementioned protein synthesis efficiency-increasing method which comprises allowing a functional nucleic acid molecule according to the present invention or aforementioned expression vector to coexist, in a body of a subject, with a target RNA. In this step, the functional nucleic acid molecule itself or an aforementioned expression vector is transfected into a cell of the subject. The target RNA may be an endogenous RNA (mRNA or the like) in the cell of the subject or artificially synthesized RNA. Alternatively, the target RNA or a DNA molecule encoding the RNA may be transfected into the cell of the subject.

Further, the protein synthesis efficiency-increasing method according to the present invention is applicable to treatment of a disease by amplifying in a body of a subject a protein factor (e.g., interferon, an apoptosis-inducing factor, or the like) that ameliorates the disease. For example, an apoptosis-inducing factor amplified in accordance with the present invention can be effectively used for treatment of tumors or the like.

The treatment method may comprise the step of allowing a functional nucleic acid molecule according to the present invention or aforementioned expression vector to coexist with a target RNA encoding a protein that ameliorates a disease in a body of a subject, wherein the target RNA hybridizes the antisense in the target determinant sequence of the functional nucleic acid molecule. In this step, the functional nucleic acid molecule itself or the aforementioned expression vector is transfected into a cell of the subject. The RNA encoding the protein that ameliorates the disease may be an endogenous RNA in the cell of the subject. Alternatively, the RNA encoding the protein that ameliorates the disease or a DNA molecule encoding the RNA may be transfected into the cell of the subject.

Any of the aforementioned treatment methods can be carried out as a pretreatment to an isolated cell to be transplanted into a body of the subject. The cell may be isolated from the body of the subject before treatment and transplantation. The aforementioned treatment methods may be a treatment method comprising the steps of (a) allowing a functional nucleic acid molecule according to the present invention or aforementioned expression vector to coexist in an isolated cell with a target RNA; and (b), after the step (a), transplanting the cell into a body of a subject. An isolated cell may be a cell which has the ability of differentiation, for example an Embryonic Stem cell (ES cell), an Embryonic Germ cell (EG cell), a somatic stem cell, especially a multi potent adult progenitor cell, stem cell, a hematopoietic stem cell, a vascular endothelia stem cell, a mesenchymal stem cell, a hepatic stem cell, a neural stem cell, an endothelial stem cell, a pancreatic stem cell, a primordial germ cell, or a multilineage-differentiating cell like a Muse cell (Kuroda et al., 2010, PNAS). Additionally, an isolated cell may be also an artificial undifferentiated cell, for example a nuclear transfer embryonic stem cell or a cell acquired the pluripotent ability by gene transfer and/or treatment of chemical compound, like an induced pluripotent stem cell (iPS cell (WO2007/069666, JP-A 2010-273680, JP-A 2010-284088, JP-A 2011-50379, JP-A 2011-4674, etc)). Additionally, an isolated cell may also be a fibroblast or an adult somatic cells that acquired the ability to become another somatic cells upon reprogramming. Additionally, after the step (a) but before the step (b), the isolated cell may be grown undifferentiated. Alternatively, after the step (a) but before the step (b), the isolated cell may be differentiated to obtain a differentiated cell or a group of differentiated cells (cell sheet or the like), and the differentiated cell or the group of differentiated cells may be transplanted into the body.

The subject indicates animals, wherein the animals include a human, preferably mammals including a human, more preferably a human. Further, the subject generally encompasses (a) one who has already shown the symptoms of a disease and (b) one who has a genetic predisposing cause but has not shown the symptoms of a disease yet. In view of this, the concept of "treatment" in the present invention includes therapeutic treatment and preventive treatment of a disease.

EXAMPLE

The present invention will be described below more specifically based on Examples, Comparative Examples, and the like. Note that the present invention is not limited to them.

The embodiments and concrete examples of implementation discussed in the foregoing detailed explanation serve solely to illustrate the technical details of the present invention, which should not be narrowly interpreted within the limits of such embodiments and concrete examples, but rather may be applied in many variations within the spirit of the present invention, provided such variations do not exceed the scope of the patent claims set forth below.

Antisense Transcription in Synthenic PARK5/Uchl1 Locus.

The FANTOM2 clone Rik6430596G22 was identified as a putative spliced AntiSense (AS) noncoding RNA (ncRNA9 of the Ubiquitin Carboxy Terminal Hydrolase 1 (UCHL1) gene 7 (Experiment 1). UchL1 is a neuron-restricted protein that acts as deubiquinating enzyme, ubiquitin ligase or monoubiquitin stabilizer (Reference 1; Liu, Y., Fallon, L., Lashuel, H. A., Liu, Z. 86 Lansbury, P. T., Jr. The UCH-L1 gene encodes two opposing enzymatic activities that affect alpha-synuclein degradation and Parkinson's disease susceptibility. Cell 111, 209-218 (2002)., Reference 2; Osaka, H., et al. Ubiquitin carboxy-terminal hydrolase L1 binds to and stabilizes monoubiquitin in neuron. Hum Mol Genet 12, 1945-1958 (2003).). It is mutated in an autosomal dominant form of PD (PARK5) (Reference 3; Leroy, E., et al. The ubiquitin pathway in Parkinson's disease. Nature 395, 451-452 (1998).). In Substantia Nigra (SN) of sporadic postmortem brains UchL1 expression was found reduced and correlated to the formation of aSYN aggregates. Loss of Uchl1 activity has been also associated to Dementia with Lewy bodies (DLB) and Alzheimer's disease (AD). Increasing Uchl1 expression has been proposed as therapeutic strategy for AD since its ectopic expression rescued beta-amyloid-induced loss of synaptic function and contextual memory in a mouse model (Reference 1, Reference 4; Butterfield, D. A., et al. Redox proteomics identification of oxidatively modified hippocampal proteins in mild cognitive impairment: insights into the development of Alzheimer's disease. Neurobiol Dis 22, 223-232 (2006)., Reference 5; Castegna, A., et al. Proteomic identification of oxidatively modified proteins in Alzheimer's disease brain. Part II: dihydropyrimidinase-related protein 2, alpha-enolase and heat shock cognate 71. J Neurochem 82, 1524-1532 (2002)., Reference 6; Choi, J., et al. Oxidative modifications and down-regulation of ubiquitin carboxyl-terminal hydrolase L1 associated with idiopathic Parkinson's and Alzheimer's diseases. J Biol Chem 279, 13256-13264 (2004).).

Rik6430596G22 is a typical 5' head to head transcript that initiates within the second intron of Uchl1 and overlaps the first 72 nts of the Sense (S) mRNA including the AUG codon (Experiment 1). The non overlapping part of the transcript also contains two embedded repetitive sequences, SINEB2 and Alu, identified by Repeatmasker. The FANTOM2 cDNA clone spans a genomic region of 70 kb and is a spliced transcript composed of four exons whose intron-junctions follow the traditional GT-AG rule (Experiment 2). In the remaining part of the disclosure Rik6430596G22 is referred as a natural AntiSense transcript to Uchl1 (AS Uchl1).

AS Uchl1 increases UchL1 protein levels with a mechanism that requires an embedded inverted SINEB2 repeat.

The interplay between S and AS transcripts was then examined. After cloning the full length cDNA for AS Uchl1 from MN9D cells with 5' rapid amplification of cDNA ends (RACE), a CMV-driven AS Uchl1 was transiently overexpressed in MN9D dopaminergic cells and endogenous Uchl1 mRNA and protein levels were monitored by qRT-PCR and western blotting. While no significant change in Uchl1 mRNA endogenous levels was observed, a strong and reproducible upregulation of UchL1 protein product was detected within 24 hours (Experiment 3). The inventors tested whether co-transfection of both cDNAs into HEK cells which do not express either transcript could recapitulate what was seen in MN9D cells. When increasing amounts of AS Uchl1 were co-transfected with murine Uchl1, a dose-dependent UchL1 protein upregulation was recorded in absence of any significant change in exogenous Uchl1 mRNA level (Experiment 4). This specific effect was not observed for unrelated controls such as GFP. To identify sequences and/or structural elements of AS Uchl1 mRNA that elicit its functional activity on UchL1 protein, deletion mutants were produced and tested in MN9D cells as well as in co-transfection in HEK cells. AS Uchl1 deletion constructs lacking the 5' first exon (AS Uchl1 Δ 5'), or the last three exons (AS Uchl1 Δ 3') failed to induce Uchl1 protein levels in both MN9D and HEK cell models, suggesting both 5' and 3' components were important to AS Uchl1 function (Experiment 5).

Additional deletion mutants were thus synthesized to assess the role of the embedded repetitive sequences, Alu and SINEB2, in UchL1 protein upregulation.

Targeted deletion of the region containing both the SINEB2 and Alu repeat elements (AS Uchl1 Δ SINEB2+ ALU) prevented Uchl1 protein induction. Deletion of a single repetitive element, (Δ-SINE B2 (764-934) and Δ-ALU (1000-1045), revealed the SINEB2 was the functional region of the transcript required for UchL1 protein increase (Experiment 6). In all cases no change in Uchl1 mRNA level was detected by transfection of AS Uchl1 wild type and deletion constructs.

Additionally the Δ-SINEB2 mutant has a dominant negative activity on the full-length AS Uchl1.

Since the deletion mutant Δ-SINEB2 lacks 170 nucleotides potentially impairing AS Uchl1 RNA secondary structure, a mutant was produced with the SINEB2 sequence flipped in between nucleotide 764-934. Interestingly, SINEB2 flip was unable to increase UchL1 protein levels thus proving the orientation-dependent activity of the SINEB2 domain embedded within AS Uchl1 (Experiment 6).

S/AS Pairs with an Embedded Inverted SINEB2 Repeat in the AS Transcript Identify a New Functional Class of ncRNA:

The FANTOM3 collection of non-coding cDNAs was bioinformatically screened for other examples of natural AS transcripts that contain SINEB2 elements (B3 subclass) in the correct orientation and 5' head to head overlapping to a protein coding gene. This identified 31 S/AS pairs similar to the Uchl1/AS Uchl1 structure (Experiment 7).

To test whether the observation for Uchl1/AS Uchl1 generalizes to other examples, the AS overlapping transcript of Uxt (ubiquitously-expressed transcript), AS Uxt (Rik4833404H03) were cloned and over-expressed. Transfection of AS Uxt in MN9D dopaminergic cells showed up-regulation of Uxt protein product with no change in the total mRNA levels confirming a more general mechanism is at work (Experiment 8).

AS Uchl1 is a Nuclear-Enriched Transcript Expressed in Dopaminergic Neurons:

Multiplex RT-PCR on a panel of mouse adult tissues, macroscopically dissected brain regions and neuronal cell lines found that AS Uchl1 expression was restricted to ventral midbrain, cortex and MN9D dopaminergic cells but absent in non-neuronal tissues, and cell lines. Double in situ hybridization with riboprobes targeting the non-overlapping region of Uchl1 showed that the mRNA was prevalent in the cytoplasm of cells of the hippocampus, cortex and subcortical regions as well as of the dorsal and ventral midbrain. AS Uchl1 riboprobe decorated similar structures. A combination of double in situ hybridization with anti-tyrosine hydroxylase immunohystofluorescence showed that mRNAs for Uchl1 and AS were expressed in the same DA neurons of the SN. Intriguingly, transcripts for the S/AS pair were prevalently localized in two different subcellular compartments: mature Uchl1 mRNA was mainly observed in the cytoplasm, while the AS RNA was nuclear, accumulating in specific subnuclear regions (Experiment 9). 50% of cellular transcripts have been recently found enriched in the nucleus representing mainly ncRNAs with unknown function. Nuclear-retained RNAs tend to accumulate in areas, called paraspeckles, that strongly resemble sites of AS Uchl1 localization and which association is regulated by embedded SINEs (Reference 7; Chen, L. L., DeCerbo, J. N. 86 Carmichael, G. G. Alu element-mediated gene silencing. Embo J 27, 1694-1705 (2008).).

By taking advantage of RACE, the precise transcriptional start site (TSS) of the AS Uchl1 gene was mapped in MN9D cells. As shown in Experiment 2, the TSS lies 250 bps upstream the previously annotated sequence and is localized in the second intron of Uchl1.

AS Uchl1 is Down-Regulated in PD Neurochemical Models and Human Post-Mortem Brains:

A 70-kb region of the mouse genome encompassing the AS UchL1 locus was then compared to the corresponding human genomic sequence using Genome Vista alignment (http://genome.lbl.gov/cgi-bin/GenomeVista). By the use of primers designed on the human sequence in correspondence to CST peaks, a 1.6 kb non-coding transcript, 5' head to head AS to human UCHL1 gene, was cloned from human brain RNA. The anatomical organization of hAS UCHL1 gene was very similar to its mouse counterpart including the extension of the S/AS pair overlapping region as well as the presence of embedded repetitive elements. hAS UCHL1 expression was highly restricted to neuronal tissues as found for mouse.

UCH-L1 protein synthesis is increased upon rapamycin treatment through nucleus-cytoplasmic shuttling of AS Uchl1 RNA and AS-dependent recruitment of Uchl1 mRNA to active polysomes.

So far, AS ncRNA is able to increase S protein levels with no change in the quantity of S mRNA. Since in physiological conditions S mRNA and AS ncRNA seem to be localized in different subcellular compartments, several stressors that have been implicated in PD pathogenesis for their ability to redistribute the nuclear AS ncRNA into the cytoplasm, where translation takes place, were assayed. MN9D cells were exposed to hydrogen peroxide 1 mM, serum starvation, rapamycin 1 ug/ml, tunycamycin 20 nM and TNFalpha 20 nM for 45 minutes and AS Uchl1 mRNA content was independently measured in the cytoplasm and nucleus by qRT-PCR. The majority of treatments had no effect, however rapamycin strongly up-regulated the amount of AS Uchl1 cytoplasmic mRNA (Experiment10).

Rapamycin is a well known inhibitor of CAP-dependent translation through its effect on mTORC1 and subsequent repression of S6K and 4E-BP1 activities. It is currently tested as anti-cancer drug and proposed for clinical trials for neurodegenerative diseases. Block of translation initiation mediated by rapamycin is able to rescue DA cell loss observed in knock-out flies for parkin and pink 1 as well as in those over-expressing the dominant PD-associated mutation of LRRK2 (Reference 8; Tain, L. S., et al. Rapamycin activation of 4E-BP prevents parkinsonian dopaminergic neuron loss. Nat Neurosci 12, 1129-1135 (2009).). Furthermore, it protects mammalian DA cells from neurochemical intoxication in vitro and in mice (Reference 9; Malagelada, C., Jin, Z. H., Jackson-Lewis, V., Przedborski, S. 86 Greene, L. A. Rapamycin protects against neuron death in in vitro and in vivo models of Parkinson's disease. J Neurosci 30, 1166-1175 (2010)., Reference 10; Malagelada, C., Ryu, E. J., Biswas, S. C., Jackson-Lewis, V. 86 Greene, L. A. RTP801 is elevated in Parkinson brain substantia nigral neurons and mediates death in cellular models of Parkinson's disease by a mechanism involving mammalian target of rapamycin inactivation. J Neurosci 26, 9996-10005 (2006).). Recently, rapamycin was shown to prevent L-DOPA-induced dyskinesia, a common severe motor side effect of the symptomatic treatment for PD (reference 11; Santini, E., Heiman, M., Greengard, P., Valjent, E. 85 Fisone, G. Inhibition of mTOR signaling in Parkinson's disease prevents L-DOPA-induced dyskinesia. Sci Signal 2, ra36 (2009).).

The effects of rapamycin on the cytoplasmic content of AS Uchl1 were confirmed by the presence of a concomitant decrease in its nuclear steady state levels, and by the absence of any de-novo transcription of AS Uchl1 (Experiment 10). Total cellular content of these transcripts remained constant. Uchl1 mRNA showed no changes in subcellular distribution, de novo transcription or total cellular content.

Despite the block in CAP-dependent translation, upon rapamycin treatment UchL1 protein level increased several fold (Experiment 11).

The inventors assessed whether AS Uchl1 was required for UchL1 induction. Stable MN9D cell lines were then established expressing constitutively shRNA for AS Uchl1, targeting the AS Uchl1 promoter region from −4 to +15 nt around the RACE-validated TSS (Reference 12; Hawkins, P. G., Santoso, S., Adams, C., Anest, V. 85 Morris, K. V. Promoter targeted small RNAs induce long-term transcriptional gene silencing in human cells. Nucleic Acids Res 37, 2984-2995 (2009)). As expected, scrambled cells showed UchL1 protein up-regulation as in MN9D parental line while cells expressing shRNA for AS Uchl1 lacked any changes in UchL1 protein levels proving a causal link between rapamycin induction of Uchl1 protein- and AS Uchl1 ncRNA expression (Experiment 12). As independent model, stable cell lines with expression of a dominant negative mutant of AS Uchl1(Δ-SINEB2) were established. When control MN9D cells stable for empty vector were treated with rapamycin, UchL1 protein was found increased. In presence of the dominant negative form of AS Uchl1 this upregulation was no longer visible (Experiment 13).

A Model for AS-Dependent Increase in S-Encoded Protein Levels Upon Rapamycin Treatment:

In growing cells mTORC1 signaling is required for proliferation and controls CAP-dependent translation machinery through the phosphorylation of its downstream substrates 4E-BPs and S6K. The cytostatic drug rapamycin inhibits mTORC1 activity leading to block of CAP-dependent translation. Here, the inventors show that in these conditions AS transcription is required for protein synthesis of selected mRNAs. Upon rapamycin addition, the nuclear-enriched ncRNA AS Uchl1 is transported into the cytoplasm where it recruits mRNAs of its S protein-encoding partner to polysomes for translation.

AS Uchl1 is thus the representative member of a new functional class of ncRNAs that are associated to S/AS pairs in the mammalian genome and appears to be composed by two domains. The overlapping region at the 5' provides specificity to a protein-encoding mRNA partner transcribed from the complementary strand. An inverted SINEB2 element at 3' is required for translational activation, representing a new function for embedded SINEB2 in the cytoplasm.

The manipulation of Uchl1 expression in vivo has been proposed for therapeutic intervention in neurodegenerative diseases, including PD and AD. Natural AS transcripts with embedded repetitive elements may thus represent endogenous molecular tools to increase protein synthesis of selected mRNAs defining a potential new class of RNA therapeutics.

Rapamycin is currently under intense scrutiny in biomedical research both as neuroprotective agent for neurodegenerative diseases and as anti-cancer drug. In mice rapamycin prevents L-DOPA-induced dyskinesia, a common severe motor side effect of the symptomatic treatment for PD. Furthermore, it protects neurons from apoptosis both in *Drosophila* genetic models as well as upon neurochemical intoxication in mammals making it an attractive molecule for anti-parkinsonian therapies (Reference 11; Santini, E et al., (2009)). It is thus important to better understand its modes of action in vivo and its interplay with pathways involved in familial cases of PD, as shown here for Uchl1. The role of AS transcription in rapamycin-induced protein synthesis adds an unexpected switch to its activities.

Artificially Synthesized AS for Increasing EGFP Expression or Antibody Expression Up-Regulates the Expression of Each Target in the Cell:

The inventors tested whether or not increased protein synthesis can be achieved on a synthetic RNA by inserting a 72 nt long target determinant sequence antisense to the enhanced green fluorescent protein (EGFP) into the appropriate sequence in AS Uchl1. As in Experiment 14, the expression of the artificial AS for up-regulating EGFP expression was designed. The fragments encoding the artificial AS was cloned into pcDNA3.1-vector (Invitrogen). This proves that a functional nucleic acid molecule with a target determinant sequence and a regulatory sequence can increase protein synthesis efficiency of any gene of interest.

Figure 15:
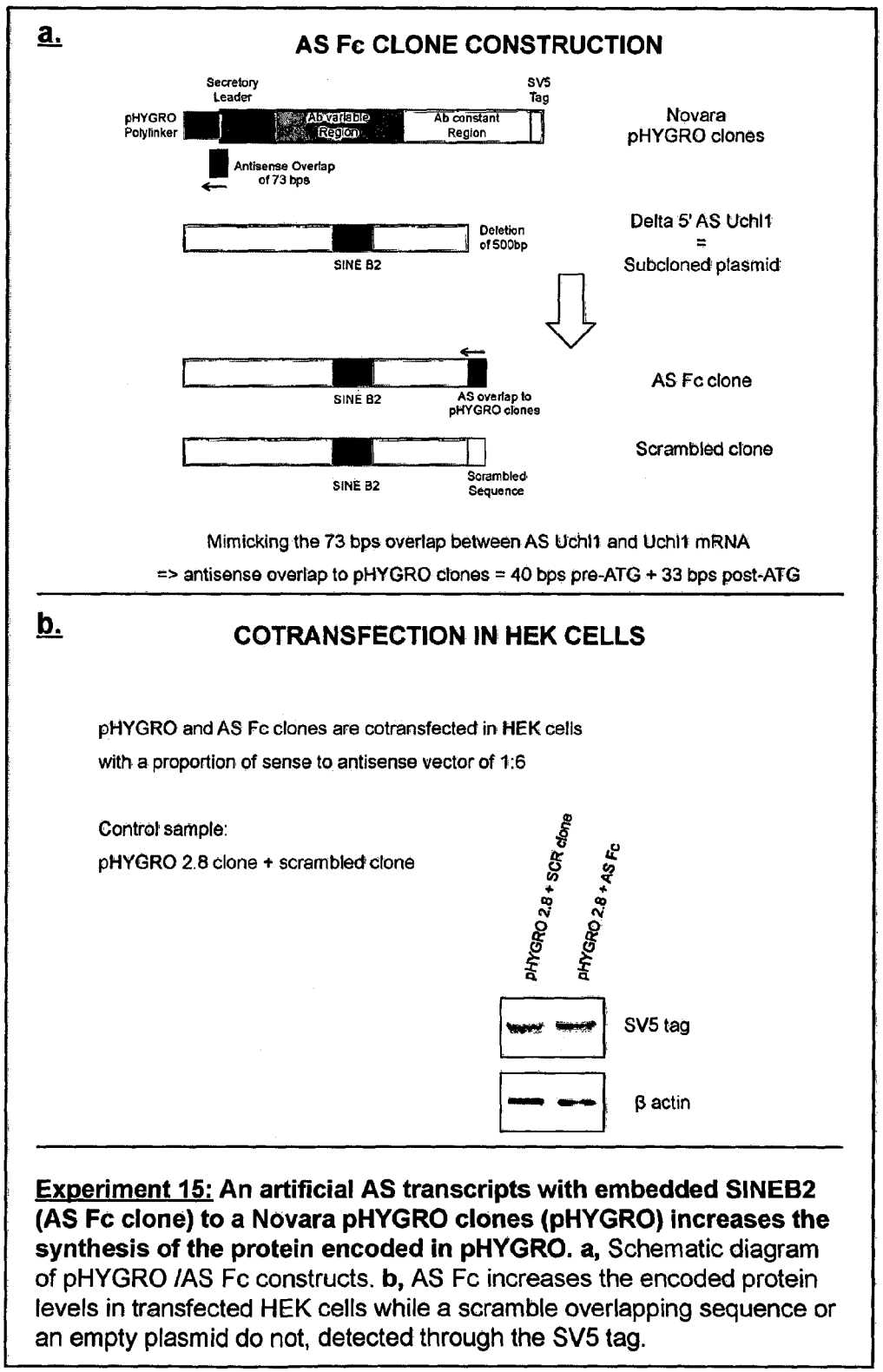
FIG. 15, related to the experiment15, is a view showing an artificial AS transcript with embedded SINEB2 (AS Fc clone) to an artificial recombinant antibody in pHYGRO (pHYGRO clones) increases the synthesis of the protein encoded in pHYGRO. a, Schematic diagram of pHYGRO/AS Fc constructs. b, AS Fc increases the encoded protein levels in transfected HEK cells while a scramble overlapping sequence or an empty plasmid do not, detected through the SV5 tag.

In the same manner, the antibody can be applied as shown in Experiment 15. An artificial AS for up-regulating a recombinant antibody was designed to target the leader sequence of the recombinant antibody (overlap is 72 bp around the ATG) and embedded into the vector (AS Fc). An artificial AS comprising a scramble sequence as the target determinant sequence (Scrambled) was also produced as control (FIG. 15). The target sequence of the antibody was included in pHYGRO vectors (pHYGRO). HEK cell line was co-transfected with pHYGRO and AS Fc or control. Transient transfection in HEK cells produced an AS Fc specific upregulation of the recombinant antibody in cell lysates. AS Fc increases the encoded protein levels in transfected HEK cells while a scramble overlapping sequence or an empty plasmid does not, detected through the SV5 tag.

Figure 16:
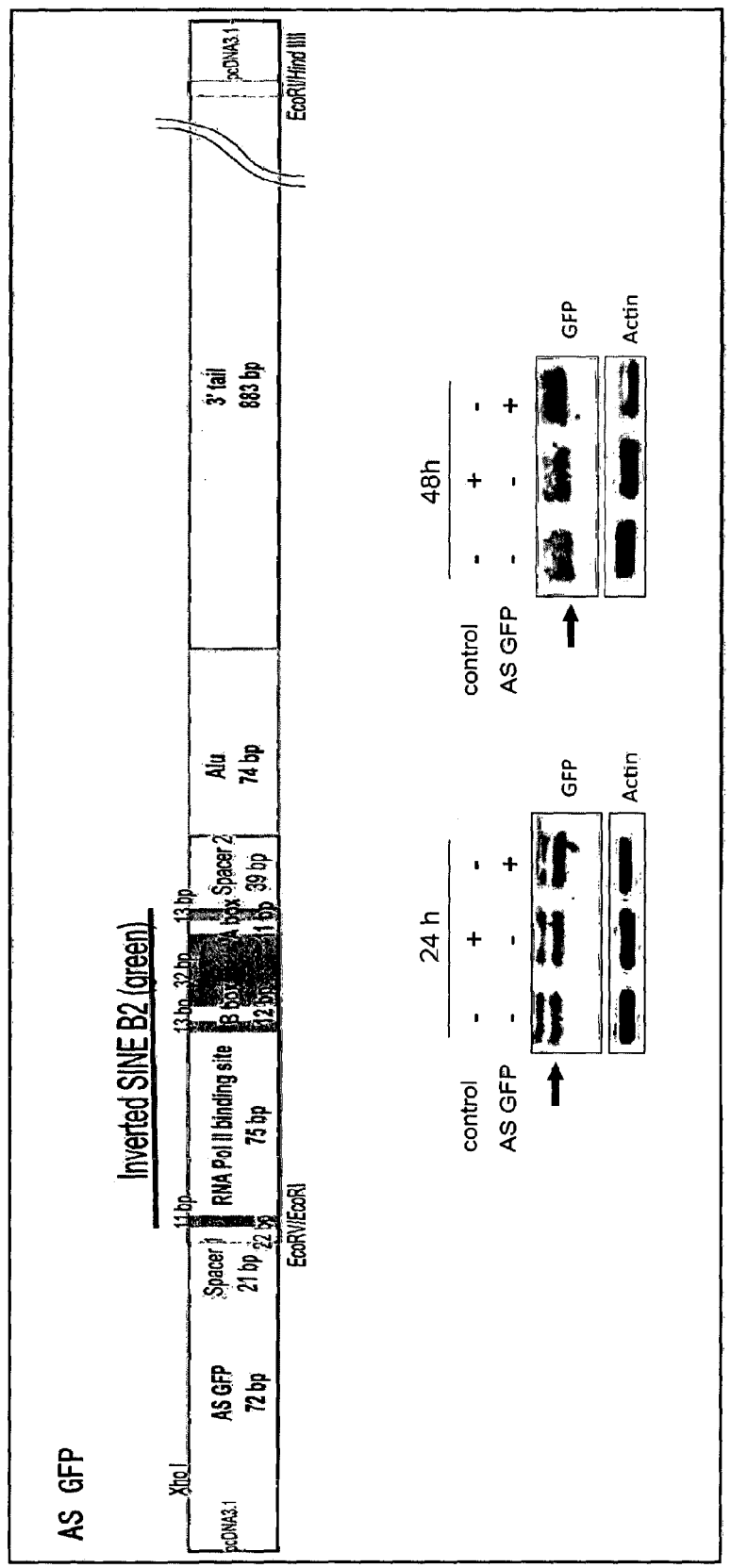
FIG. 16, related to the experiment16, is a view showing how an artificial AS transcript with embedded SINEB2 to an artificial Green Fluorescent Protein (EGFP) mRNA increases EGFP protein synthesis.
Figure 17:
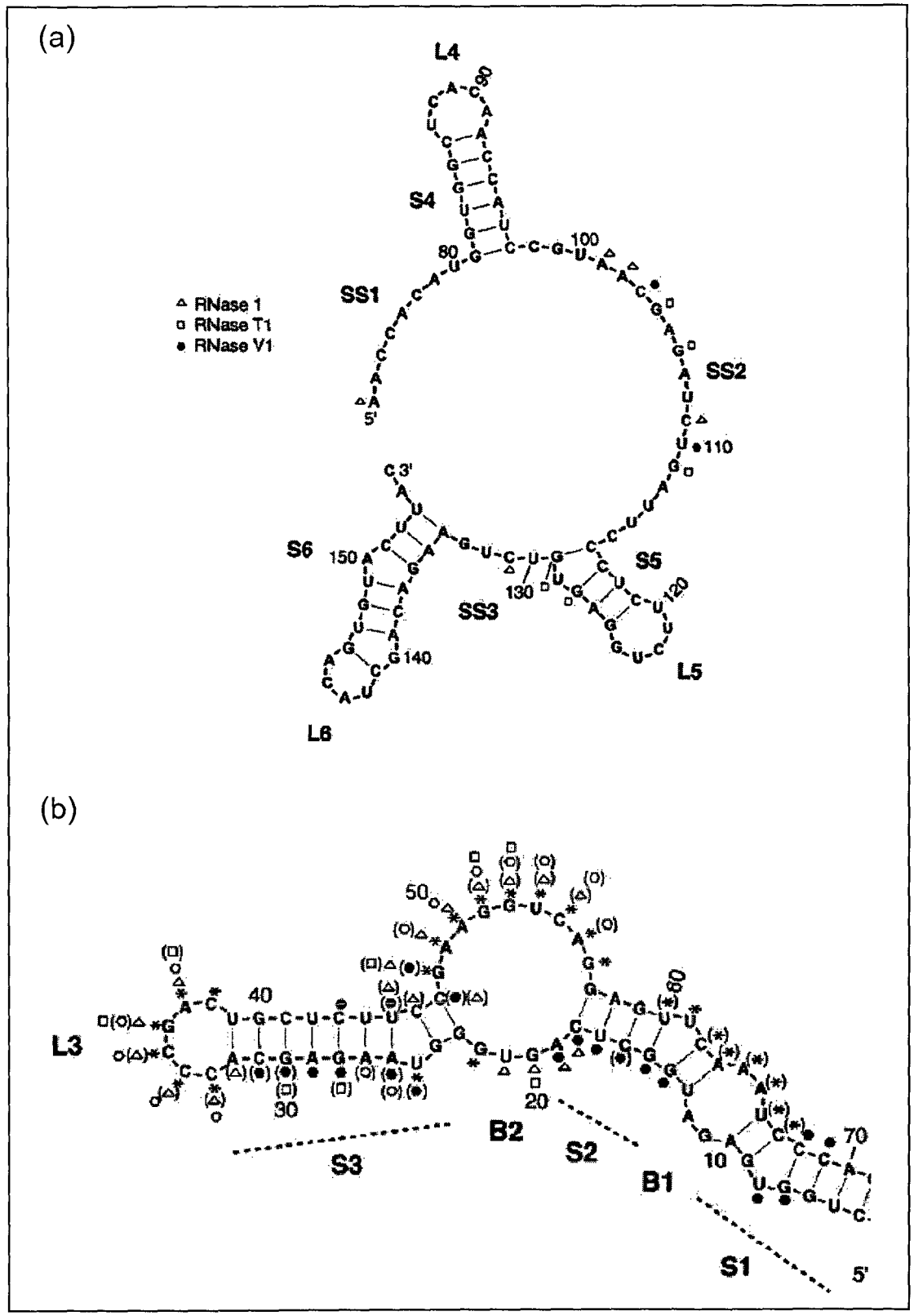
FIG. 17 is a view showing the examples of the potential predicted structures of SINE B2-derived sequence.

For further examination (Experiment 16), HEK cell line was transfected with EGFP expression vector pEGFP-C2 (Clontech) with Lipofectamine 2000 (Invitrogen) in accordance with manufacture's instructions. Then, the transfectants which stably express low EGFP expression were selected. AS GFP comprises target determinant sequence against EGFP and it was artificially designed to increase the efficiency of EGFP protein synthesis (FIG. 16). The stable transfectants were further transfected with the vector encoding AS GFP or control vector. After 24 hours or 48 hours from the transfection of AS GFP construct or control vector, the cells were collected and lysed. The GFP level in the cell lysate was monitored by western blotting. The low expression of EGFP in the transfectant was increased by transfection of the AS GFP construct (FIG. 16).

In an additional experiment, a construct with a target determinant sequence that overlaps for 44 nt to the plasmid backbone till the ATG codon for EGFP has been synthesized. This construct (SINEup005) increases protein synthesis of the target gene very efficiently (more than 10 fold).

Therefore, this is one of evidences that the new type of AS which the inventors found can be artificially designed as long as the functional nucleic acid molecule includes a target determinant sequence comprising an antisense sequence to a target sequence in the protein-encoding RNA for which protein synthesis efficiency is to be increased and a regulatory sequence having an activity of increasing of the protein synthesis efficiency.

Methods

Plasmids

RACE fragment: The 5' UTR of AS Uchl1 was amplified by RACE PCR (GeneRacer, Invitrogen) by MN9D total RNA and cloned into pGEM®-T Easy vector (Promega).

Full length AS Uchl1: Full length DNA sequence of AS was amplified via fusion PCR starting from RACE fragment and FANTOM clone Rik 6430596G22 with following primers For mAS Uchl1 fl 5'-ACAAAGCTCAGCCCACACGT-3' (SEQ ID No:13) and Rev mAS Uchl1fl 5'-CATAGGGT-TCATT-3'(SEQ ID No:14).
Uchl1: Mouse Uchl1 mRNA was cloned from FANTOM 2900059022 with following primers: For mUchl1 5'-ATG-CAGCTGAAGCCGATG-3'(SEQ ID No:15) and Rev mUchl1 5'-TTAAGCTGCTTTGCAGAGAGC-3' (SEQ ID No:16) AS Uchl1 shRNA: Oligo containing the sequence −14/+4 around the TSS of AS Uchl1 CGCGCAGTGACA-CAGCACAAA (SEQ ID No:17) are cloned into pSUPER-.retro.puro vector (OligoEngine, Seattle, Wash.), scrambled sequence was used as control.
Deletional Mutants:
Δ5': For mAS Uchl1 fl and Rev Δ 5'AS Uchl15' TACCAT-TCTGTGCGGTGCA-3' (SEQ ID No:18).
Δ3': For mAS Uchl1 GACCTCCTCTAGCACTGCACA-3' (SEQ ID No:19) and Rev mAS Uchl1 fl.
For fine deletional mutants, PCR fragment I is cloned NheI-EcoRI site in PcDNA3.1- and PCR fragment II into following EcoRI-HindIII site.
AS Uchl1 Δ (Alu+SINEB2):
PCR fragment I: For mAS Uchl1 fl and Rev pre-SINE B2 5'-CAATGGATTCCATGT-3' (SEQ ID No:20). PCR fragment II: For post-ALU 5'-GATATAAGGAGAATCTG-3' (SEQ ID No:21) and Rev mAS fl.
AS Uchl1 Δ(Alu):
PCR fragment I: mAS Uchl1 fl and Rev pre-Alu 5'-TTATAG TATGTGTTGTC-3' (SEQ ID No:22). PCR fragment II: For post-ALU 5'-GATATAAGGAGAATCTG-3' (SEQ ID No:23) and Rev mAS fl cloned into EcoRI-HindIII site.
AS Uchl1 Δ (SINEB2):
PCR fragment I: For mAS Uchl1 fl and Rev pre-SINE B2 5'-CAATGGATTCCATGT-3' (SEQ ID No:24). PCR fragment II: For post-SINE B2 5'-GAATTCCTC-CAGTCTCTTA-3' (SEQ ID No:25) and Rev mAS fl.
AS uchl1 (Alu+SINEB2) flip: PCR fragment I: obtained with For SINE B2 inside 5'-TGCTAGAGGAGG-3' (SEQ ID No:26) and Rev Alu flip 5'-GTCAGGCAATCC-3' (SEQ ID No:27) are cloned in the unique EcoRI site of AS Uchl1 Δ (Alu+SINEB2).
AS uchl1 SINEB2 flip: PCR fragment obtained with For SINE B2 inside 5'-TGCTAGAGGAGG-3' (SEQ ID No:28) and Rev SINE flip 5'-AAAGAGATGGC-3' (SEQ ID No:29) are cloned in the unique EcoRI site of AS Uchl1 Δ (SINEB2).
Cells
MN9D cells were seeded in 10 mm petri-dishes in Dulbecco's modified Eagle's medium containing 10% of fetal bovine serum and, penicillin (50 units/ml), streptomycin (50 units/ml). Treatments were done by adding Rapamycin (R0395, Sigma) at final concentration of 1 ug/ml in fresh medium for 45 minutes.
For the establishment of MN9D stable cells (siRNA −15/+4, siRNA scrambled, pcDNA 3.1- and Δ SINE B2) MN9D cells were seeded in 100 mm petri-dishes and transfected with Lipofectamine 2000 (Invitrogen) according to manufacturer's instruction, the day after cells seeded for selection with 500 uM of Neomycin (#N1142, Sigma). HEK-293T cells were grown in DMEM (GIBCO) supplemented with 10% fetal bovine serum (Sigma-Aldrich), 100 units/mL penicillin, and 100 μm/mL streptomycin (Sigma) at 37° C. in a humidified $CO_2$ incubator.
PCR
PCR analysis: Total RNA was extracted using Trizol reagent (Invitrogen) according to manufacturers instruction. It was subjected to DNAse I treatment (Ambion) and 1 ug was retrotranscribed using iScript cDNA Synthesis Kit (BioRad).

Real Time qRT-PCR was carried out using Sybr green fluorescence dye (2×iQ5 SYBR Green supermix, BioRad). Actin and GAPDH were used as internal standard. Relative quantification was performed with the comparative Ct method.

```
Actin:
                                        (SEQ ID No: 30)
sense       5'- CACACCCGCCACCAGTTC-3', (SEQ ID No: 31)
antisense   5'-CCCATTCCCACCATCACACC-3'.

Gapdh:
                                        (SEQ ID No: 32)
sense       5'-GCAGTGGCAAAGTGGAGATT-3', (SEQ ID No: 33)
antisense   5'-GCAGAAGGGGCGGAGATGAT-3'.

AS Uchl1 overlap:
                                        (SEQ ID No: 34)
sense       5'-GCACCTGCAGACACAAACC-3', (SEQ ID No: 35)
antisense   5'-TCTCTCAGCTGCTGGAATCA-3'.

AS Uchl1:
                                        (SEQ ID No: 36)
            5'CTGGTGTGTATCTCTTATGC (SEQ ID No: 37)
antisense   5'CTCCCGAGTCTCTGTAGC.

Uchl1:
                                        (SEQ ID No: 38)
sense       5'- CCCGCCGATAGAGCCAAG, (SEQ ID No: 39)
antisense   5'-ATGGTTCACTGGAAAGGG-3'.

ASUchl1 pre RNA:
                                        (SEQ ID No: 40)
            5'-CCATGCACCGCACAGAATG-3', (SEQ ID No: 41)
antisense   5'-GAAAGCTCCCTCAAATAGGC-3'.

Pre_AOribosomal RNA:
                                        (SEQ ID No: 42)
sense       5'-TGTGGTGTCCAAGTGTTCATGC-3', (SEQ ID No: 43)
antisense   5'-CGGAGCACCACATCGATCTAAG-3.

AS_Uxt:
                                        (SEQ ID No: 44)
sense       5'-CAACGTTGGGGATGACTTCT, (SEQ ID No: 45)
antisense   5'-TCGATTCCCATTACCCACAT;

Uxt:
                                        (SEQ ID No: 46)
sense       5'-TTGAGCGACTCCAGGAAACT-3', (SEQ ID No: 47)
antisense   5'-GAGTCCTGGTGAGGCTGTC-3'.
```

Multiplex RT PCR was performed with SuperScript® III One-Step RT-PCR System with Platinum® Taq DNA Polymerase (Invitrogen). 500 mg of total DNAse treated RNA was incubated with reverse primers for Gapdh, Uchl1, AS Uchl1. The reaction was performed for 60 minutes at 60 degrees.

Each volume was then splitted in three and forward primers were added at final concentration of 200 nM to the reaction. The PCR reaction comprised 40 cycles of 95 degrees for 15 seconds, followed by 60 degrees for 45 seconds, and final 68 degrees for 30 seconds.

Western Blot

Cells were lysed in SDS sample buffer 2×. Proteins were separated in 15% SDS-polyacrilamide gel and transferred to nitrocellulose membrane. Immunoblotting was performed with the primary antibodies: anti-Uchl1 (#3524 Cell Signalling) 1:300 and anti-b actin (A5441, Sigma) 1:5000. Signals were revealed after incubation with recommended secondary antibodies conjugated with horseradish peroxidase by using enhanced chemioluminescence for Uchl1 (#WBKLS0500 Immobilion Western Chemioluminescent HRP substrate) and ECL detection reagent (RPN2105, GE Healthcare).

Cellular Fractionation

Nucleo cytoplasmic fractionation was performed using Nucleo Cytoplasmic separation kit (Norgen) according to manufacturer's instruction. RNA was eluted and DNAseI treated. The purity of the cytoplasmic fraction was confirmed by Real Time qRT-PCR on Pre-ribosomal RNA.

Two Colour In situ Hybridization (ISH)

Reagents: anti DIG antibody D8156 (Sigma); streptavidin HRP RPN1231-100UL (Amersham Bioscience); DIG labeling mix #11 277 073 910 (Roche) BIO-labelling Mix #11 685 597 910 (Roche), Ribonucleic acid, transfer from baker's yeast R8759 (Sigma), Deoxyribonucleic acid, single stranded from salmon testes D7656 (Sigma), Blocking reagent #11 096 176 001 (Roche), TSA Cy3 system (Perkin Elmer, Heidelberg, Germany).

After perfusion with 4% formaldehyde, the mouse brain was cryoprotected overnight in 30% sucrose. In situ hybridization was performed on cryostat slices (16 um). Sense and antisense probes were generated by in vitro transcription from the cDNA encoding the distal 600 bps of mouse Uchl1 cDNA and the last 1000 bps of mouse AS Uchl1. The probes for Uchl1 were labeled with digoxigenin, probes for AS Uchl1 were labeled with biotin. Incorporation of both bioting and digoxigenin was checked via Northern Blot. Slices were pretreated with hydrogenum peroxide 3% for 30 minutes. Hybridization was performed with probes at a concentration of 1 mg/ml (Uchl1) and 3 mg/ml for AS Uchl1 at 60° C. for 16 h. For biotinilated RNA detection, streptavidin-HRP was used 1:250 for 2 hours in TNB buffer (Tris HCl PH 7.5 100 mM, NaCl 150 mM, 0.5% Blocking Reagent), and signals are visualized using the TSA Cy3 system after washing in TNT buffer (Tris HCl PH 7.5 100 mM, NaCl 150 mM, 0.05% tween).

ISH on DIG-labeled probe was performed by incubating slices with monoclonal anti-DIG antibody after TSA reaction. To combine RNA ISH with immunofluorescence, slice were incubated with the antibody anti TH (#AB152, Chemicon) 1:1000. Signals are then detected with fluorescent dye-conjugated secondary antibody goat anti-rabbit 405 and goat anti-mouse 488. Sections were then washed, mounted with Vectashield (Vector lab) mounting medium and observed at confocal microscope (Leica).

Post-Mortem Human Brain Samples

Brain samples were obtained from the brain bank at the Institute of Neuropathology, Bellvitge Hospital (University of Barcelona, Spain). Samples were dissected at autopsy with the informed consent of patients or their relatives and the institutional approval of the Ethics Committee of the University of Barcelona. Brains were obtained from Caucasian, pathologically confirmed PD cases and age-matched controls (Navarro et al., 2009). Briefly, all cases of PD had suffered from classical PD, none of them had cognitive impairment and their neuropathological characterization was made according to established criteria. Control healthy subjects showed absence of neurological symptoms and of metabolic and vascular diseases, and the neuropathological study disclosed no abnormalities, including lack of Alzheimer disease and related pathology. The time between death and tissue preparation was in the range of 3 to 5 hours.

Bioinformatic Analysis

For the identification of a candidate human hortologue of AS Uchl1, conservation between human and mouse in the ortho-logus region of AS uchl1 was performed using VISTA genome browser. The inventors selected parameters for conserved sequence tags (CTS) that have a minimum of 75% identity between the mouse and human genome. For each conserved element a primer on the homologus human region was designed.

For the identification of additional translational activator candidates, the inventors searched for FANTOM3 full-length cDNAs that were non-coding RNAs and overlap the 5' end of coding transcripts in a head to head configuration [PMID: 16141072]. The filtered set of 8535 FANTOM3 ncRNA transcripts described in the Nordstrom et al 2009 (Nordstrom, K. J., et al. Critical evaluation of the FANTOM3 non-coding RNA transcripts. *Genomics* 94, 169-176 (2009).) was used as our starting point. Genomic locations of these ncRNA transcripts and REFSEQ (Maglott, D. R., Katz, K. S., Sicotte, H. 86 Pruitt, K. D. NCBI's LocusLink and RefSeq. *Nucleic Acids Res* 28, 126-128 (2000)) coding transcripts were extracted from the alignments in the UCSC Genome browser (Kent, W. J., et al. The human genome browser at UCSC. *Genome Res* 12, 996-1006 (2002)) to identify a set of 788 coding-sense: non-coding-antisense pairs. The ncRNAs were then checked by repeat masker to identify SINEB2 related sequences (Smit, A F A, Hubley, R & Green, P. RepeatMasker Open-3.0.1996-2010 <http://www.repeatmasker.org>). This reduced the number of pairs to 127 protein coding transcripts with overlap at the 5' end (60 with a sense strand version of the repeat, 53 with an antisense version and 14 with both sense and antisense versions).

Alignment of the SINEB2 related elements was then carried out using Clustalw (http://www.ebi.ac.uk/Tools/clustalw2/index.html. From this analysis the antisense overlapping transcripts with a repeat most like that of Uchl1-as and in the same orientation were chosen for experimental testing (Uxt1-AS).

Sequences

As example, the following is a list of sequences that are complementary to protein coding mRNAs. They contain a fraction that provides examples of a target determinant sequence [now in light blue highlight] and a regulatory sequence [how highlighted in red]. The regulatory sequence in this list of natural antisense is as short at 89 nucleotides in this example. The length of the adaptor sequences in this partial list of antisense RNAs is as short as 44 nt.

Below each sequence there is a summary of the alignments with the retrotransposon elements as determined by Repeat-mask program.

```
AK078321 (AS Uchl1)
AK078321.1
(SEQ ID No:7)
aaacgatgctcttggaggatagggacagagactgcgcgccgcgccactca
ctttgttcagcatctgaaagccaaaagcaaagaggaaaatgataataaaa
ctaaatgattcagctaccgagctgtagctaagggtcagccttatttctcc
cgaagcgacccagcagctatgcttac*ctcggggttaatctccatcggct
tcagctg[cat]ttcgcggatggcacctgcagacacaaacccgaggagc
cgaaaaacagccggtggagccgcccaggctgctgttataaagcgccggc
ctcgctcactgggaaagcctgagcaggggagcagggagcagaaacaagca
gaggaggaaggccaagagggctcgaactccc*catgcaccgcacagaatg
gtacaagccaagcccccaaacttgcagtctcactcgccgaagtgctccc
cggactgggcatggtagcacgcacctgtgattccagcagctgagagagag
gccgagcccacatggaatccattgtgcagtgctagaggaggtcagaagag
ggcattggatccccagaactggagttatacggtaacctcgtggtggttg
tgaaccaccatgtggatgatattgagttccaaacactggtcctgtgcaa
gagcatccagtgctcttaagtgctgagccatctctttagctccagtctct
taaaaaacaaacaaacgaacgaacagcaagggagctgggtatgacaacac
atactataattctagtactcaggatgctgaaacaggaggattgcctgact
ggggagatataaggagaatctgttgtcacccccaccccctccccataaggc
agaataaaagaacgtcctataaacaaataaacaaacaacccaataaaaca
aaaccaagatctctccaccttttctttgcttttcagacttgtaataag
gccctttggagtgcaggatattcggcaggacagaggagagaccat
cagttctttctttgatcaagaagactatgttccttagcaaactggtcgt
attatctcttatgcaatgagcctggaaagagggcacagccaccgaggatg
gtacagcatggatggatggtacgctacagagactcgggagcccaactgtg
agtggctgactggcatggtaggttcagggaagaattggcctgtgaagaaa
atgttcttgaaaagtgaacaaggtgcaggagtgggtggtcctgggc
aaagcaggggtgcatcccagcctcaggaatagcacagcagaggtctgt
tgatgcatgcgagtgcatgacctgcttgccaatagacgatcaagaatggg
caaagcatcatgggtgatgagtgggagagggatgagacattcctttctc
cctgctgagacttccattgaaccgatgagttctgaatagaagatgccccc
ccaccccccaccagtgtagaatctgaagggaggcatatattaccctata
ttactctgtgttggcggcgagctatctgacagccaaccttcccatacatt
tcattgggcatacactaatgacaggaagttccttttgcttgtatgcaaga
gatggctcacacgatggagaatttaatcttgttagtttgttatttatgtg
tcctaaattttgttcaataaaaatgaaacactcctatg
```

In Bold overlap region (UchL1) Italic is 72 bp
The boxed nucleotide CAT is complementary to the CDS starting ATG

```
AK029359.1 (AS Uxt)                         (SEQ ID No: 8)
*tagtctcgctgcagtacgtcactgataaag*ccactcaacgttggggatga
cttctttcggctcgagctacggagttgcttctgcccaacccgattttgga
actcgttcact*caccggtacaggagtacggcgtttaccgtagggccaccg
gcaataact*gccagaagaagttgtgggattccctggaactggagcaacca
acagtttgtgtgcaccatgtgggtaatgggaatcgaacctgggtcctcta
taagactggccagtgctcttaactactgaggtgcatttctttcggaattg
attcacataactattatgctatactgtttgaagtatttattagaaaaaca
tcagaaagagatttggaccactttcatttacatgaagaaatatcttaggg
tttcttttcaggtatctttgagtatcttctgacactagaagatcctgtaa
actctacagacttcaacagaattgaagaacctggacagagcagagttacc
aacaagagagcccagggatagcattaacatggtggttactcaagacctaa
ctcagccagggagacataccaaggcctatgaggtgaagggaaaagaaggg
tgacccaaagggcaggaatttttatcctgaacttttgagccttatagaa
aaacataatttgttgggcatgttttctgaccctcatacagtttttacaac
catttgaagatatagttctagctctagtaggctctacaggaaggtatatc
aaactttttaacagaacacttta*ttatttt*aaatatatgagtatttcacc
tgcataggcgcacagtacccacagagactagaagagggtggcagatctcc
tgagactggagttaatgcttgtgagctgccatgtggatgctggaaatcaa
acccaggtcctttggaaggcaggcaggtgctcttaatcatggaagcatct
cttcagctcctacccctagttctttaattttgtttttaaatttttgaggtag
ggttttttgctaagttacttgggctggccttggactagtaaccattctgtgt
cagccttctgggattagaggtatgtgctagcatgtctagcatctttctat
ttctttggttttccttctaattaattaaaaaatacattatcttct
```

In Bold overlap region (UchL1)

|  |  |  |  |  | position | matching | repeat |  | position |  |  |
| --- | --- | --- | --- | --- | --- | --- | --- | --- | --- | --- | --- |
| SW | perc | perc | perc | query | in query | class/ |  |  | in repeat |  |  |
| score | div. | del. | ins. | sequence | begin end (left) | repeat | family | begin | end | (left) | ID |
| 701 | 19.7 | 1.2 | 10.3 | AK078321.1 | 521 690 (995) | C B3 | SINE/B2 | (60) | 156 | 1 | 1 |
| 303 | 29.2 | 2.1 | 0.0 | AK078321.1 | 730 802 (883) | + B1F1 | SINE/Alu | 1 | 77 | (50) | 2 |

ANNOTATION EVIDENCE:

| 701 | 19.67 | 1.18 | 10.26 | AK079321.1 | 521 | 690 | 995 | C B3 | SINE/B2 | 1 | 156 | 60 | 0 |
| --- | --- | --- | --- | --- | --- | --- | --- | --- | --- | --- | --- | --- | --- |

```
AK078321.1      521 GTGC--AGTGCTAGAGGAGGTCAGAAGAGGGCATTGGATCCCCCAGAACT      568
                      --i   iv v   i               i i         ii
C B3#SINE/B2    156 GTGCCTGGTGCCCGCGGAGGCCAGAAGAGGGCGTCGGATCCCCTGGAACT      107

AK078321.1      569 GGAGTTATACGGTAACCTCGTGGTGGTTGTGAACCACCATGTGGATGGAT      618
                      i ------------ i           i i         i ---
C B3#SINE/B2    106 GGAGTTACA------------GATGGTTGTGAGCCGCCATGTGGGTG---       72

AK078321.1      619 ATTGAGTTCCAAACACTGGTCCTGTGCAAGAGCATCCAGTGCTCTTAAGT      668
                      -i i vvi i    v v        v  v         v        vi
C B3#SINE/B2     71 -CTGGGAATCGAACCCGGGTCCTCTGGAAGAGCAGCCAGTGCTCTTAACC       23

AK078321.1      669 GCTGAGCCATCTCTTTAGCTCC                                 690
                             ii  i
C B3#SINE/B2     22 GCTGAGCCATCTCTCCAGCCCC                                   1
```

Matrix = 25p43g.matrix
Transitions/transversions = 2.00 (20/10)
Gap_init rate = 0.02 (3/169), avg. gap size = 6.00 (18/3)

| SW score | perc div. | perc del. | perc ins. | query sequence | position in query begin | end | (left) | matching repeat repeat | class/ family | position in repeat begin | end | (left) | ID |
|---|---|---|---|---|---|---|---|---|---|---|---|---|---|
| 617 | 19.5 | 0.8 | 2.3 | Unnamed Sequence | 160 | 290 | (855) | C B3 | SINE/B2 | (79) | 137 | 9 | 1 |
| 883 | 19.9 | 12.3 | 0.5 | Unnamed Sequence | 774 | 960 | (185) | C B3 | SINE/B2 | (7) | 209 | 1 | 2 |
| 327 | 27.5 | 6.1 | 4.3 | Unnamed Sequence | 977 | 1090 | (55) | C PB1D10 | SINE/Alu | (0) | 117 | 2 | 3 |

ANNOTATION EVIDENCE:

| 617 | 19.54 | 0.76 | 2.33 | Unnamed Sequence | 160 | 290 | 556 | C B3 | SINE/B2 | 9 | 137 | 79 | 2 |
|---|---|---|---|---|---|---|---|---|---|---|---|---|---|

```
AK039359.1      160 GCCAGAAGAAGTTGTGGGATTCCCTGGAACTGGAGCAACCAACAGTTTGT        209
                        i vi  v     i              iv vii  ii    -
C B3#SINE/B2    137 GCCASAAGAGGGCGTTCGGATCCCCTGGAACTGGAGTTACAGATGGTT-GT       89

AK029359.1      210 GTGC-ACCATGTGGGTAATGGGAATCGAACCTGGGTCCTCTATAAGACTG        258
                     v -i        iv              i           iv vii
C B3#SINE/B2     88 GAGCCGCCATGTGGGTGCTGGGAATCGAACCCGGGTCCTCTGGAAGAGCA        39

AK029359.1      259 GCCAGTGCTCTTAACTACTGAGGTGCATTTCT        290
                              ii       v--  i
C B3#SINE/B2     38 GCCAGTGCTCTTAACCGCTGAGC--CATCTCT          9
```

ANNOTATION EVIDENCE:

| 883 | 19.89 | 12.30 | 0.48 | Unmamed Sequence | 774 | 960 | 72 | C B3 | SINE/B2 | 1 | 209 | 7 | 1 |
|---|---|---|---|---|---|---|---|---|---|---|---|---|---|

```
AK029359.1      774 TTATTTTAAATATATGAGTATTTCACCTGCATAG------GCGCAC----       813
                        vi i    i   ii        iv------  i   ----
C B3#SINE/B2    209 TTATTTTATGTGTATGAGTGTTTTGCCTGCATGTATGTCTGTGCACCACG       160

AK029359.1      814 ---------AGTACCCACAGAGACTAGAAGAGGGTGGCAGATCTCCTGAG       854
                    ---------i    i  ii    ii      iv i    i      i
C B3#SINE/B2    159 TGCCGTGCCTGGTGCCCGCGGAGGCCAGAAGAGGGCGTCGGATCCCCTGGA      110

AK029359.1      855 ACTGGAGTTA---ATGCTTGTGAGCTGCCATGTGGATGCTGGAAATCAAA       901
                             ---   v        i    i        i    i     i
C B3#SINE/B2    109 ACTGGAGTTACAGATGGTTGTGAGCCGCCATGTGGGTGCTGGGAATCGAA        60

AK029359.1      902 CCCAGGTCCTTTGGAAG-GCAGGCAGGTGCTCTTAATCATGGAAGCATCT       950
                        i       i       - v  -      i iiv  iv
C B3#SINE/B2     59 CCCGGGTCCTCTGGAAGAGCAGCCAG-TGCTCTTAACCGCTGAGCCATCT        11

AK025359.1      951 CTTCAGCTCC       960
                    i      i
C B3#SINE/B2     10 CTCCAGCCCC        1
```

```
Matrix = 25p43g.matrix
Transitions/transversions = 1.78 (16/9)
Gap_init rate = 0.02 (3/130), avg. gap size = 1.33 (4/3)
```

Other sequences in the study:

B2#SINE/B2
(SEQ ID No: 9)
gggctggagagatggctcagtggttaagagcacctgactgctcttccagc ggtcctgagttcaattcccagcaaccacatggtggctcacaaccatctgt aatgagatctgatgccctcttctggtgtgtctgaagacagctacagtgta cttacatataataaataaataaataaataaatcttaaaaaaaaaaaaaag aaagaaaaa >B3#SINE/B2 216 bp (SEQ ID No: 10)
GGGGCTGGAGAGATAGCTCAGCGGTTAAGAGCACTGGCTGCTCTTCCAGA

GGACCCGGGTTCGGTTCCCAGCACCCACATGGCGGCTCACAACCGTCTGT

AACTCTAGTTCCAGGGGATCTRACNCCCTCTTCTGACCTCCACGGGCACC

AGGCACGCACGTGGTACACAGACGTACATGCARGCAAAACACTCATACAC

ATAAAATAAAAATAAATMTTTWAAAAAA

Uchl1 cloned to Pme-blunt site of pcDNA 3.1-
(SEQ ID No: 11)
CGGCTCCTCGGGTTTGTGTCTGCAGGTGCCATCCGCGAAGATGCAGCTGA

AGCCGATGGAGATTAACCCCGAGATGCTGAACAAAGTGTTGGCCAAGCTG

```
GGGGTCGCCGGCCAGTGGCGCTTCGCCGACGTGCTAGGGCTGGAGGAGGA
GACTCTGGGCTCAGTGCCATCCCCTGCCTGCGCCCTGCTGCTCCTGTTTC
CCCTCACGGCCCAGCATGAAAACTTCAGGAAAAAGCAAATTGAGGAACTG
AAGGGACAGGAAGTTAGCCCTAAAGTTTACTTCATGAAGCAGACCATCGG
AAACTCCTGTGGTACCATCGGGTTGATCCACGCAGTGGCCAACAACCAAG
ACAAGCTGGAATTTGAGGATGGATCCGTCCTGAAACAGTTTCTGTCTGAA
ACGGAGAAGCTGTCCCCCGAAGATAGAGCCAAGTGTTTCGAGAAGAACGA
GGCCATCCAGGCGGCCCATGACTCCGTGGCCCAGGAGGGCCAGTGTCGGG
TAGATGACAAAGTGAATTTCCATTTTATTCTGTTCAACAACGTGGACGGC
CATCTGTACGAGCTCGATGGGCGAATGCCCTTTCCAGTGAACCATGGCGC
CAGCTCAGAGGACTCTCTGCTGCAGGATGCTGCCAAGGTCTGCAGAGAAT
TCACTGAGCGCGAGCAGGGGGAGGTCCGCTTCTCTGCCGTGGCTCTCTGC
AAAGCAGCTTAAGTCTGGGGAGAGAGAACCAGCCGATCCCCCCTTCCCTG
GGCAGGTGCGCGCGGCCCGCCCTTGGTTTGCAGCTTTAGCACTTAGAACC
ACAGCTGTCTTCTTGCGTTCTACAGCCCCATCCCCTCCACCCCACCCAGG
CCACCAGGGGGCTCTGTCACAGCCACACCAGGCTGAGCACTTTGCCTCCT
GTGTGTCTCGTACCTTGCTCTCTACGGTCTCTTTGGTTTCTGTCTGTAAG
TTACGGCCCTGGATGTGGTTTGTCTAGTCCTTAAGAGGAAGAATAAAACT
TTGCTGGTGAGAG

AS Uch11 full
length cloned into Xba-Hindii site in pcDNA3.1-
                                      (SEQ ID No: 12)
ACAAAGCTCAGCCCACACGTGGCTCGCGCGAAGCCCTCGGACTAGAGTCC
GCGGGCCGTCGCCACGCCCTCGAGAGCTGCTCCCCGCGCTCGTTGCTGTC
CGGGTCCATCCTCCGCCACCTCCCCGTGATCGATCTCTCAGTCACTCCCA
AACCCCTAGATAACTCAGGGCAGAGACGACACCCAGCTGGGCGcCCCAGC
CCAGCCACCTCCATTGCACAGGGCGCGGCCGGCTGGGCGTCTCCAAACGA
TGCTCTTGGAGGATAGGGACAGAGACTGCGCGCCGCGCCACTCACTTTGT
TCAGCATCTGAAAGCCAAAAGCAAAGAGGAAAATGATAATAAAACTAAAT
GATTCAGCTACCGAGCTGTAGCTAAGGGTCAGCCTTATTTCTCCCGAAGC
GACCCAGCAGCTATGCTTACCTCGGGGTTAATCTCCATCGGCTTCAGCTG
CATCTTCGCGGATGGCACCTGCAGACACAAACCCGAGGAGCCGAAAAAAC
AGCCGGTGGAGCCGCCCAGGCTGCTGTTATAAAGCGCCGGCCTCGCTCAC
TGGGAAAGCCTGAGCAGGGGAGACGGGAGCAGAAACAAGCAGAGGAGGAA
GGCCAAGAGGGCTCGAACTCCCCCATGCACCGCACAGAATGGTACAAGCC
AAGCCCCCAAACCTTGCAGTCTCACTCGCCGAAGTGCTCCCCGGACTGGG
CATGGTAGCACGCACCTGTGATTCCAGCAGCTGAGAGAGAGGCCGAGCCC
ACATGGAATCCATTGTGCAGTGCTAGAGGAGGTCAGAAGAGGGCATTGGA
TCCCCCAGAACTGGAGTTATACGGTAACCTCGTGGTGGTTGTGAACCACC
ATGTGGATGGATATTGAGTTCCAAACACTGGTCCTGTGCAAGAGCATCCA
GTGCTCTTAAGTGCTGAGCCATCTCTTTAGCTCCAGTCTCTTAAAAAACA
AACAAACGAACGAACAGCAAGGGAGCTGGGTATGACAACACATACTATAA
TTCTAGTACTCAGGATGCTGAAACAGGAGGATTGCCTGACTGGGAGATAT
AAGGAGAATCTGTTGTCACCCCCACCCCTCCCCATAAAGGCAGAATAAAA
GAACGTCCTATAAACAAATAAACAAACAACCCAATAAAACAAAACCAAGA
TCTCTCCACCTTTTCTTTGCTTTTTCAGACTTTGTAATAAGGCCCTTTGG
AGTGCAGGATATTCGGCAGGACAAGCAGAGAGGGAGACCATCAGTTCTTT
CTTTGATCAAGAAGACTATGTTCCTTAGCAAACTGGTGTGTATTATCTCT
TATGCAATGAGCCTGGAAAGAGGGCACAGCCACCGAGGATGGTACAGCAT
GGATGGATGGTACGCTACAGAGACTCGGGAGCCCAACTGTGAGTGGCTGA
CTGGCATGGTAGGTTCAGGGAAGAATTGGCCTGTGAAGAAAATGTTCTTG
AAAAGTGAACAAGGTGCAGGAGGTAGGAGTGGGTCCTGGGCAAAGCAGGG
GGTGCATCCCAGCCTCAGGGAATAGCACAGCAGAGGTCTGTTGATGCATG
CGAGTGCATGACCTGCTTGCCAATAGACGATCAAGAATGGGCAAAGCATC
ATGGGTGATGAGTGGGAGAGGGGATGAGACATTCCTTTCTCCCTGCTGAG
ACTTCCATTGAACCGATGAGTTCTGAATAGAAGATGCCCCCCCACCCCCC
CACCAGTGTAGAATCTGAAGGGAGGCATATATTACCCTATATTACTCTGT
GTTGGCGGCGAGCTATCTGACAGCCAACCTTCCCATACATTTCATTGGGC
ATACACTAATGACAGGAAGTTCCTTTTGCTTGTATGCAAGAGATGGCTCA
CACGATGGAGAATTTAATCTTGTTAGTTTGTTATTTATGTGTCCTAAATT
TTGTTCAATAAAAATGAAACACTCCTATG
```

The examples of SINE B2 embedded in cDNA clones sequence are as following, but is limited to them.

| Gene with AS_refseq | start B2 | end B2 | strand | subtype | | | | Legend; cDNA cloneID_alignment Start position_Alignent end_type of Repeat element |
|---|---|---|---|---|---|---|---|---|
| NM_177182 | 973 | 1013 | −2766 + | B2_Mm2 | SINE/B2 | 2 | 42 | −153 >AK032380_973_1013_+_B2_Mm2 |
| NM_009351 | 859 | 1044 | −1470 + | B2_Mm1t | SINE/B2 | 2 | 185 | −8 >AK033525_859_1044_+_B2_Mm1t |
| NM_144515 | 1564 | 1718 | −761 + | B2_Mm2 | SINE/B2 | 1 | 158 | −37 >AK033993_1564_1718_+_B2_Mm2 |
| NM_198300 | 520 | 712 | −1160 + | B2_Mm2 | SINE/B2 | 1 | 188 | −7 >AK039361_520_712_+_B2_Mm2 |
| NM_028428 | 1801 | 1997 | −245 + | B2_Mm1t | SINE/B2 | 1 | 193 | 0 >AK042841_1801_1997_+_B2_Mm1t |
| NM_010661 | 946 | 1111 | −1515 + | B2_Mm2 | SINE/B2 | 1 | 195 | 0 >AK043817_946_1111_+_B2_Mm2 |
| NM_007485 | 722 | 912 | −417 + | B2_Mm2 | SINE/B2 | 1 | 194 | −1 >AK044205_722_912_+_B2_Mm2 |
| NM_010633 | 971 | 1164 | −67 + | B2_Mm2 | SINE/B2 | 1 | 195 | 0 >AK047213_971_1164_+_B2_Mm2 |
| NM_030207 | 714 | 787 | −446 + | B2_Mm2 | SINE/B2 | 1 | 88 | −107 >AK079217_714_787_+_B2_Mm2 |
| NM_145470 | 1498 | 1697 | −1057 + | B2_Mm2 | SINE/B2 | 1 | 193 | −2 >AK081722_1498_1697_+_B2_Mm2 |
| NM_024282 | 1379 | 1555 | −2 + | B2_Mm2 | SINE/B2 | 2 | 187 | −8 >AK132990_1379_1555_+_B2_Mm2 |
| NM_133994 | 1001 | 1057 | −86 + | B2_Mm2 | SINE/B2 | 2 | 58 | −137 >AK133457_1001_1057_+_B2_Mm2 |

| Gene with AS_refseq | start B2 | end B2 | strand | subtype | | | | Legend; cDNA cloneID_alignment Start position_Alignent end_type of Repeat element |
|---|---|---|---|---|---|---|---|---|
| NM_133994 | 1057 | 1137 | −6 + | B2_Mm2 | SINE/B2 | 91 | 171 | −24 >AK133457_1057_1137_+_B2_Mm2 |
| NM_178244 | 2323 | 2513 | −45 + | B2_Mm2 | SINE/B2 | 1 | 195 | 0 >AK133632_2323_2513_+_B2_Mm2 |
| NM_008997 | 734 | 923 | −3 + | B2_Mm2 | SINE/B2 | 1 | 186 | −9 >AK133808_734_923_+_B2_Mm2 |
| NM_080555 | 286 | 382 | −4 + | B2_Mm1t | SINE/B2 | 75 | 171 | −22 >AK134674_286_382_+_B2_Mm1t |
| NM_010332 | 2428 | 2606 | −1 + | B2_Mm2 | SINE/B2 | 1 | 183 | −12 >AK135599_2428_2606_+_B2_Mm2 |
| NM_172467 | 2948 | 3108 | −3 + | B2_Mm2 | SINE/B2 | 1 | 162 | −33 >AK137583_2948_3108_+_B2_Mm2 |
| NM_175115 | 81 | 274 | −2006 + | B2_Mm2 | SINE/B2 | 2 | 195 | 0 >AK138675_81_274_+_B2_Mm2 |
| NM_010071 | 3150 | 3339 | −54 + | B2_Mm2 | SINE/B2 | 1 | 195 | 0 >AK155102_3150_3339_+_B2_Mm2 |
| NM_183014 | 288 | 442 | −20 + | B3A | SINE/B2 | 48 | 198 | 0 >AK015655_288_442_+_B3A |
| NM_026555 | 277 | 435 | −24 + | B3A | SINE/B2 | 40 | 198 | 0 >AK021299_277_435_+_B3A |
| NM_033077 | 1109 | 1295 | −1732 + | B3A | SINE/B2 | 5 | 189 | −9 >AK029689_1109_1295_+_B3A |
| NM_019789 | 1052 | 1211 | −1195 + | B3 | SINE/B2 | 33 | 196 | −20 >AK030353_1052_1211_+_B3 |
| NM_178891 | 2403 | 2558 | −3 + | B3 | SINE/B2 | 20 | 176 | −40 >AK030551_2403_2558_+_B3 |
| NM_145579 | 2546 | 2719 | −346 + | B3 | SINE/B2 | 2 | 206 | −10 >AK031007_2546_2719_+_B3 |
| NM_008510 | 2255 | 2404 | −429 + | B3A | SINE/B2 | 57 | 198 | 0 >AK034030_2255_2404_+_B3A |
| NM_153579 | 1071 | 1262 | −798 + | B3 | SINE/B2 | 1 | 214 | −2 >AK035406_1071_1262_+_B3 |
| NM_145942 | 1006 | 1219 | −681 + | B3 | SINE/B2 | 2 | 216 | 0 >AK037188_1006_1219_+_B3 |
| NM_025788 | 1871 | 2045 | −757 + | B3 | SINE/B2 | 1 | 215 | −1 >AK039409_1871_2045_+_B3 |
| NM_008019 | 877 | 1044 | −1057 + | B3 | SINE/B2 | 2 | 211 | −5 >AK040162_877_1044_+_B3 |
| NM_001081475 | 1431 | 1582 | −6 + | B3 | SINE/B2 | 69 | 216 | 0 >AK040401_1431_1582_+_B3 |
| NM_001081475 | 1586 | 1745 | −2 + | B3 | SINE/B2 | 3 | 206 | −10 >AK040401_1586_1745_+_B3 |
| NM_007485 | 722 | 810 | −519 + | B3 | SINE/B2 | 1 | 89 | −127 >AK044205_722_810_+_B3 |
| NM_007485 | 835 | 912 | −417 + | B3 | SINE/B2 | 138 | 215 | −1 >AK044205_835_912_+_B3 |
| NM_178794 | 826 | 959 | −986 + | B3A | SINE/B2 | 2 | 129 | −69 >AK045196_826_959_+_B3A |
| NM_008915 | 737 | 940 | −298 + | B3 | SINE/B2 | 8 | 201 | −15 >AK046652_737_940_+_B3 |
| NM_010633 | 971 | 1096 | −135 + | B3 | SINE/B2 | 1 | 129 | −87 >AK047213_971_1096_+_B3 |
| NM_199476 | 3267 | 3405 | −1039 + | B3 | SINE/B2 | 2 | 149 | −67 >AK047540_3267_3405_+_B3 |
| NM_144795 | 2052 | 2248 | −546 + | B3 | SINE/B2 | 2 | 210 | −6 >AK048854_2052_2248_+_B3 |
| #N/A | 1858 | 2028 | −5 + | B3A | SINE/B2 | 1 | 176 | −22 >AK049524_1858_2028_+_B3A |
| NM_001038621 | 1207 | 1363 | −359 + | B3A | SINE/B2 | 2 | 160 | −38 >AK053130_1207_1363_+_B3A |
| NM_181423 | 1666 | 1733 | −71 + | B3A | SINE/B2 | 2 | 72 | −126 >AK054359_1666_1733_+_B3A |
| NM_153515 | 1403 | 1520 | −470 + | B3A | SINE/B2 | 63 | 183 | −15 >AK078013_1403_1520_+_B3A |
| NM_198415 | 403 | 623 | −1212 + | B3 | SINE/B2 | 1 | 216 | 0 >AK078328_403_623_+_B3 |
| NM_152220 | 1794 | 1979 | −561 + | B3 | SINE/B2 | 3 | 213 | −3 >AK078537_1794_1979_+_B3 |
| NM_025729 | 1 | 165 | −203 + | B3 | SINE/B2 | 15 | 177 | −39 >AK079403_1_165_+_B3 |
| NM_016693 | 1307 | 1517 | −13 + | B3 | SINE/B2 | 2 | 216 | 0 >AK080235_1307_1517_+_B3 |
| NM_010151 | 814 | 1024 | −451 + | B3 | SINE/B2 | 2 | 216 | 0 >AK082108_814_1024_+_B3 |
| NM_009713 | 1690 | 1882 | −5 + | B3 | SINE/B2 | 1 | 199 | −17 >AK082325_1690_1882_+_B3 |
| NM_001029985 | 221 | 280 | −1179 + | B3 | SINE/B2 | 108 | 168 | −48 >AK084376_221_280_+_B3 |
| NM_009737 | 1805 | 2005 | −406 + | B3 | SINE/B2 | 1 | 207 | −9 >AK085337_1805_2005_+_B3 |
| NM_027081 | 984 | 1130 | −1155 + | B3 | SINE/B2 | 1 | 162 | −54 >AK086470_984_1130_+_B3 |
| NM_018779 | 876 | 1062 | −530 + | B3A | SINE/B2 | 2 | 188 | −10 >AK089148_876_1062_+_B3A |
| NM_027919 | 1468 | 1667 | −185 + | B3 | SINE/B2 | 1 | 213 | −3 >AK090182_1468_1667_+_B3 |
| NM_011034 | 434 | 608 | −12 + | B3 | SINE/B2 | 2 | 216 | 0 >AK131819_434_608_+_B3 |
| NM_175551 | 1802 | 1895 | −513 + | B3A | SINE/B2 | 64 | 176 | −22 >AK132737_1802_1895_+_B3A |
| NM_175551 | 1829 | 1928 | −480 + | B3 | SINE/B2 | 101 | 213 | −3 >AK132737_1829_1928_+_B3 |
| NM_007921 | 951 | 1134 | −1650 + | B3A | SINE/B2 | 3 | 187 | −11 >AK133325_951_1134_+_B3A |
| NM_001039042 | 1220 | 1315 | −292 + | B3A | SINE/B2 | 48 | 142 | −56 >AK134755_1220_1315_+_B3A |
| NM_177328 | 1378 | 1504 | −285 + | B3 | SINE/B2 | 85 | 216 | 0 >AK134874_1378_1504_+_B3 |
| NM_021899 | 1172 | 1259 | −140 + | B3 | SINE/B2 | 1 | 95 | −121 >AK135206_1172_1259_+_B3 |
| NM_008705 | 1521 | 1717 | −572 + | B3A | SINE/B2 | 1 | 197 | −1 >AK136279_1521_1717_+_B3A |
| NM_001079932 | 2116 | 2299 | −702 + | B3 | SINE/B2 | 6 | 208 | −8 >AK137643_2116_2299_+_B3 |
| NM_001079932 | 3059 | 3253 | −2 + | B3 | SINE/B2 | 4 | 205 | −11 >AK137643_3059_3253_+_B3 |
| NM_001033286 | 2524 | 2698 | −63 + | B3A | SINE/B2 | 4 | 181 | −17 >AK138296_2524_2698_+_B3A |
| NM_008962 | 928 | 1095 | −375 + | B3 | SINE/B2 | 1 | 153 | −63 >AK138521_928_1095_+_B3 |
| NM_175349 | 2151 | 2347 | −181 + | B3A | SINE/B2 | 11 | 196 | −2 >AK139254_2151_2347_+_B3A |
| NM_177003 | 1277 | 1466 | 0 + | B3 | SINE/B2 | 1 | 200 | −16 >AK139647_1277_1466_+_B3 |
| NM_007965 | 1338 | 1488 | −5 + | B3 | SINE/B2 | 51 | 216 | 0 >AK140072_1338_1488_+_B3 |
| NM_010192 | 1808 | 1933 | −45 + | B3 | SINE/B2 | 1 | 126 | −90 >AK140346_1808_1933_+_B3 |
| NM_027446 | 1871 | 1983 | −2794 + | B3A | SINE/B2 | 1 | 130 | −68 >AK140616_1871_1983_+_B3A |
| NM_027446 | 2318 | 2342 | −2435 + | B3A | SINE/B2 | 131 | 156 | −42 >AK140616_2318_2342_+_B3A |
| NM_177186 | 2061 | 2142 | −351 + | B3 | SINE/B2 | 130 | 211 | −5 >AK142359_2061_2142_+_B3 |
| NM_145134 | 2963 | 3148 | −1292 + | B3 | SINE/B2 | 28 | 210 | −6 >AK142507_2963_3148_+_B3 |
| NM_009890 | 2740 | 2968 | −135 + | B3 | SINE/B2 | 1 | 216 | 0 >AK142879_2740_2968_+_B3 |
| NM_146055 | 5202 | 5272 | −94 + | B3 | SINE/B2 | 60 | 141 | −75 >AK143143_5202_5272_+_B3 |
| NM_008977 | 1344 | 1513 | −645 + | B3 | SINE/B2 | 11 | 205 | −11 >AK143279_1344_1513_+_B3 |
| NM_026036 | 2001 | 2167 | −272 + | B3A | SINE/B2 | 1 | 169 | −29 >AK149843_2001_2167_+_B3A |
| NM_001159519 | 1440 | 1548 | −1422 + | B3A | SINE/B2 | 55 | 163 | −35 >AK157402_1440_1548_+_B3A |
| NM_001159519 | 2503 | 2556 | −558 + | B3 | SINE/B2 | 1 | 56 | −160 >AK157402_2503_2556_+_B3 |
| NM_001159519 | 2544 | 2616 | −498 + | B3 | SINE/B2 | 109 | 177 | −39 >AK157402_2544_2616_+_B3 |
| NM_001159519 | 2702 | 2896 | −412 + | B3A | SINE/B2 | 1 | 198 | 0 >AK157402_2702_2896_+_B3A |
| NM_001110504 | 1778 | 1909 | −25 + | B3 | SINE/B2 | 58 | 210 | −6 >AK160921_1778_1909_+_B3 |
| NM_030714 | 2153 | 2335 | −62 + | B3 | SINE/B2 | 40 | 216 | 0 >AK165234_2153_2335_+_B3 |
| NM_025825 | 945 | 1052 | −383 RC | B2_Mm1a | SINE/B2 | −85 | 108 | 1 >AK014613_945_1052_RC_B2_Mm1a |

-continued

| Gene with AS_refseq | start B2 | end B2 | strand | subtype | | | | Legend; cDNA cloneID_alignment Start position_Alignent end_type of Repeat element |
|---|---|---|---|---|---|---|---|---|
| NM_133756 | 1102 | 1289 | −246 RC | B2_Mm2 | SINE/B2 | −4 | 191 | 1 >AK016234_1102_1289_RC_B2_Mm2 |
| NM_183294 | 1565 | 1750 | −1384 RC | B2_Mm1a | SINE/B2 | −8 | 185 | 4 >AK029702_1565_1750_RC_B2_Mm1a |
| NM_009446 | 531 | 710 | −2730 RC | B2_Mm2 | SINE/B2 | −6 | 189 | 2 >AK030803_531_710_RC_B2_Mm2 |
| NM_025788 | 1687 | 1839 | −963 RC | B2_Mm2 | SINE/B2 | −11 | 184 | 1 >AK039409_1687_1839_RC_B2_Mm2 |
| NM_177785 | 1626 | 1682 | −1130 RC | B2_Mm2 | SINE/B2 | −4 | 191 | 137 >AK040275_1626_1682_RC_B2_Mm2 |
| NM_177785 | 1682 | 1739 | −1073 RC | B2_Mm2 | SINE/B2 | −94 | 101 | 46 >AK040275_1682_1739_RC_B2_Mm2 |
| NM_177785 | 1776 | 1952 | −1036 RC | B2_Mm1t | SINE/B2 | −13 | 180 | 2 >AK040275_1776_1952_RC_B2_Mm1t |
| NM_007485 | 1137 | 1341 | −192 RC | B2_Mm2 | SINE/B2 | 0 | 195 | 2 >AK044205_1137_1341_RC_B2_Mm2 |
| NM_175273 | 537 | 714 | −1793 RC | B2_Mm2 | SINE/B2 | −5 | 190 | 1 >AK048762_537_714_RC_B2_Mm2 |
| NM_029409 | 1005 | 1172 | −2204 RC | B2_Mm1t | SINE/B2 | −14 | 179 | 1 >AK049449_1005_1172_RC_B2_Mm1t |
| NM_007836 | 282 | 407 | −2067 RC | B2_Mm2 | SINE/B2 | −67 | 128 | 2 >AK054076_282_407_RC_B2_Mm2 |
| NM_007836 | 1764 | 1860 | −614 RC | B2_Mm2 | SINE/B2 | −97 | 98 | 2 >AK054076_1764_1860_RC_B2_Mm2 |
| NR_002891 | 1 | 181 | −2344 RC | B2_Mm1a | SINE/B2 | −10 | 183 | 2 >AK076350_1_181_RC_B2_Mm1a |
| NM_026500 | 984 | 1157 | −1501 RC | B2_Mm2 | SINE/B2 | −14 | 181 | 1 >AK076438_984_1157_RC_B2_Mm2 |
| NM_052994 | 2158 | 2323 | −1225 RC | B2_Mm2 | SINE/B2 | −4 | 191 | 8 >AK079094_2158_2323_RC_B2_Mm2 |
| NM_153100 | 1870 | 2057 | −1774 RC | B2_Mm2 | SINE/B2 | 0 | 195 | 1 >AK086953_1870_2057_RC_B2_Mm2 |
| NM_175313 | 2088 | 2261 | −2958 RC | B2_Mm2 | SINE/B2 | −9 | 186 | 14 >AK132441_2088_2261_RC_B2_Mm2 |
| NM_001114140 | 5305 | 5461 | −1145 RC | B2_Mm2 | SINE/B2 | −38 | 157 | 2 >AK133162_5305_5461_RC_B2_Mm2 |
| NM_009579 | 1059 | 1251 | −2941 RC | B2_Mm2 | SINE/B2 | 0 | 195 | 1 >AK137370_1059_1251_RC_B2_Mm2 |
| NM_010567 | 1613 | 1794 | −1882 RC | B2_Mm2 | SINE/B2 | −2 | 193 | 1 >AK138181_1613_1794_RC_B2_Mm2 |
| NM_001008423 | 2088 | 2222 | −57 RC | B2_Mm2 | SINE/B2 | −60 | 135 | 1 >AK141165_2088_2222_RC_B2_Mm2 |
| NM_199027 | 935 | 1064 | −63 RC | B2_Mm2 | SINE/B2 | −65 | 130 | 1 >AK141411_935_1064_RC_B2_Mm2 |
| NM_001033316 | 3103 | 3283 | −440 RC | B2_Mm2 | SINE/B2 | −5 | 190 | 2 >AK145736_3103_3283_RC_B2_Mm2 |
| NR_003492 | 748 | 810 | −977 RC | B2_Mm1a | SINE/B2 | −6 | 187 | 123 >AK147092_748_810_RC_B2_Mm1a |
| NM_010567 | 935 | 1129 | −78 RC | B2_Mm2 | SINE/B2 | 0 | 195 | 2 >AK148373_935_1129_RC_B2_Mm2 |
| NM_026115 | 3593 | 3791 | −204 RC | B2_Mm2 | SINE/B2 | −1 | 194 | 1 >AK155374_3593_3791_RC_B2_Mm2 |
| NM_010398 | 1080 | 1265 | −909 RC | B2_Mm2 | SINE/B2 | −8 | 187 | 1 >AK157261_1080_1265_RC_B2_Mm2 |
| NM_007893 | 764 | 820 | −1012 RC | B2_Mm2 | SINE/B2 | −94 | 101 | 47 >AK163105_764_820_RC_B2_Mm2 |
| NM_007893 | 894 | 1062 | −938 RC | B2_Mm2 | SINE/B2 | −13 | 182 | 1 >AK163105_894_1062_RC_B2_Mm2 |
| NM_007893 | 1390 | 1436 | −564 RC | B2_Mm2 | SINE/B2 | −5 | 190 | 137 >AK163105_1390_1436_RC_B2_Mm2 |
| NM_007893 | 1436 | 1490 | −510 RC | B2_Mm2 | SINE/B2 | −94 | 101 | 47 >AK163105_1436_1490_RC_B2_Mm2 |
| NM_007893 | 1543 | 1701 | −299 RC | B2_Mm1t | SINE/B2 | −24 | 169 | 1 >AK163105_1543_1701_RC_B2_Mm1t |
| NM_177186 | 1783 | 1964 | −258 RC | B2_Mm1t | SINE/B2 | −7 | 186 | 2 >AK163831_1783_1964_RC_B2_Mm1t |
| NM_030714 | 1401 | 1588 | −809 RC | B2_Mm2 | SINE/B2 | 0 | 195 | 3 >AK165234_1401_1588_RC_B2_Mm2 |
| NM_001110101 | 1253 | 1420 | −1139 RC | B2_Mm2 | SINE/B2 | −22 | 173 | 2 >AK169421_1253_1420_RC_B2_Mm2 |
| NM_007601 | 387 | 544 | −1715 RC | B3A | SINE/B2 | −22 | 176 | 1 >AK016423_387_544_RC_B3A |
| NM_027346 | 1459 | 1690 | −74 RC | B3 | SINE/B2 | −2 | 214 | 1 >AK019925_1459_1690_RC_B3 |
| NM_138664 | 1382 | 1411 | −1334 RC | B3A | SINE/B2 | −148 | 50 | 21 >AK028982_1382_1411_RC_B3A |
| NM_013840 | 160 | 290 | −556 RC | B3 | SINE/B2 | −79 | 137 | 9 >AK029359_160_290_RC_B3 |
| NM_013840 | 774 | 960 | −72 RC | B3 | SINE/B2 | −7 | 209 | 1 >AK029359_774_960_RC_B3 |
| NM_153591 | 769 | 982 | −1569 RC | B3 | SINE/B2 | −6 | 210 | 1 >AK032194_769_982_RC_B3 |
| NM_028794 | 1926 | 2130 | −654 RC | B3 | SINE/B2 | −12 | 204 | 2 >AK032215_1926_2130_RC_B3 |
| NM_001012311 | 1317 | 1437 | −1013 RC | B3 | SINE/B2 | −44 | 172 | 38 >AK034331_1317_1437_RC_B3 |
| NM_001012311 | 1335 | 1437 | −1013 RC | B3A | SINE/B2 | −54 | 144 | 38 >AK034331_1335_1437_RC_B3A |
| NM_134122 | 1094 | 1205 | −719 RC | B3 | SINE/B2 | −88 | 128 | 1 >AK035015_1094_1205_RC_B3 |
| NM_153579 | 1443 | 1617 | −577 RC | B3 | SINE/B2 | −2 | 214 | 45 >AK035406_1443_1617_RC_B3 |
| NM_153579 | 1483 | 1633 | −561 RC | B3A | SINE/B2 | −18 | 180 | 27 >AK035406_1483_1633_RC_B3A |
| NM_001081014 | 1615 | 1715 | −218 RC | B3A | SINE/B2 | −88 | 110 | 1 >AK039704_1615_1715_RC_B3A |
| NM_018747 | 432 | 531 | −1672 RC | B3A | SINE/B2 | −31 | 167 | 49 >AK040672_432_531_RC_B3A |
| NM_176841 | 1677 | 1886 | −64 RC | B3 | SINE/B2 | 0 | 216 | 2 >AK041236_1677_1886_RC_B3 |
| NM_133878 | 1676 | 1882 | −314 RC | B3 | SINE/B2 | −7 | 209 | 1 >AK041654_1676_1882_RC_B3 |
| NM_145215 | 2334 | 2533 | −484 RC | B3 | SINE/B2 | 0 | 216 | 3 >AK041742_2334_2533_RC_B3 |
| NM_145369 | 1132 | 1336 | −593 RC | B3 | SINE/B2 | −7 | 209 | 5 >AK042861_1132_1336_RC_B3 |
| NM_172691 | 248 | 442 | −151 RC | B3A | SINE/B2 | −18 | 180 | 10 >AK043958_248_442_RC_B3A |
| NM_007485 | 938 | 1127 | −202 RC | B3 | SINE/B2 | −37 | 179 | 2 >AK044205_938_1127_RC_B3 |
| NM_007485 | 989 | 1127 | −202 RC | B3A | SINE/B2 | −57 | 141 | 2 >AK044205_989_1127_RC_B3A |
| NM_007925 | 592 | 713 | −719 RC | B3 | SINE/B2 | −54 | 162 | 39 >AK045677_592_713_RC_B3 |
| NM_177006 | 3566 | 3620 | −1104 RC | B3 | SINE/B2 | −160 | 56 | 2 >AK046828_3566_3620_RC_B3 |
| NM_010633 | 431 | 640 | −591 RC | B3 | SINE/B2 | −4 | 212 | 8 >AK047213_431_640_RC_B3 |
| NM_010633 | 457 | 640 | −591 RC | B3A | SINE/B2 | −7 | 191 | 8 >AK047213_457_640_RC_B3A |
| NM_008842 | 1460 | 1636 | −53 RC | B3A | SINE/B2 | −4 | 194 | 10 >AK047301_1460_1636_RC_B3A |
| NM_199476 | 2716 | 2780 | −1664 RC | B3A | SINE/B2 | −36 | 162 | 98 >AK047540_2716_2780_RC_B3A |
| NM_013514 | 1203 | 1416 | −311 RC | B3 | SINE/B2 | 0 | 216 | 1 >AK048309_1203_1416_RC_B3 |
| NM_080793 | 2342 | 2396 | −1333 RC | B3A | SINE/B2 | −5 | 193 | 144 >AK048747_2342_2396_RC_B3A |
| NM_080793 | 2430 | 2530 | −1199 RC | B3A | SINE/B2 | −55 | 143 | 47 >AK048747_2430_2530_RC_B3A |
| NM_001038621 | 159 | 275 | −1447 RC | B3 | SINE/B2 | −56 | 160 | 34 >AK053130_159_275_RC_B3 |
| NM_007836 | 1747 | 1860 | −614 RC | B3 | SINE/B2 | −97 | 119 | 2 >AK054076_1747_1860_RC_B3 |
| NM_010878 | 1134 | 1337 | −1192 RC | B3 | SINE/B2 | 0 | 216 | 1 >AK078161_1134_1337_RC_B3 |
| NM_011670 | 521 | 690 | −995 RC | B3 | SINE/B2 | −60 | 156 | 1 >AK078321_521_690_RC_B3 |
| NM_026086 | 882 | 1046 | −355 RC | B3A | SINE/B2 | −18 | 180 | 1 >AK079515_882_1046_RC_B3A |
| NM_025396 | 1081 | 1179 | −370 RC | B3 | SINE/B2 | −27 | 189 | 75 >AK080749_1081_1179_RC_B3 |
| NM_007923 | 2420 | 2567 | −582 RC | B3A | SINE/B2 | −48 | 150 | 4 >AK086589_2420_2567_RC_B3A |
| NM_028427 | 1420 | 1597 | −495 RC | B3 | SINE/B2 | −5 | 211 | 2 >AK090347_1420_1597_RC_B3 |
| NM_026157 | 1871 | 2066 | −1227 RC | B3A | SINE/B2 | 0 | 198 | 5 >AK132393_1871_2066_RC_B3A |

-continued

| Gene with AS_refseq | start B2 | end B2 | strand | subtype | | | | Legend; cDNA cloneID_alignment Start position_Alignent end_type of Repeat element |
|---|---|---|---|---|---|---|---|---|
| NM_026157 | 2342 | 2408 | −885 RC | B3A | SINE/B2 | −131 | 67 | 1 | >AK132393_2342_2408_RC_B3A |
| NM_026157 | 2473 | 2606 | −687 RC | B3A | SINE/B2 | −25 | 173 | 28 | >AK132393_2473_2606_RC_B3A |
| NM_175313 | 2113 | 2261 | −2958 RC | B3 | SINE/B2 | −40 | 176 | 14 | >AK132441_2113_2261_RC_B3 |
| NM_175313 | 4127 | 4308 | −948 RC | B3 | SINE/B2 | −6 | 210 | 28 | >AK132441_4127_4308_RC_B3 |
| NM_024282 | 1137 | 1290 | −91 RC | B3A | SINE/B2 | −39 | 159 | 1 | >AK132990_1137_1290_RC_B3A |
| NM_177328 | 277 | 358 | −1283 RC | B3A | SINE/B2 | −56 | 142 | 66 | >AK134874_277_358_RC_B3A |
| NM_177328 | 405 | 484 | −1157 RC | B3A | SINE/B2 | −133 | 65 | 1 | >AK134874_405_484_RC_B3A |
| NM_177328 | 545 | 713 | −928 RC | B3A | SINE/B2 | −4 | 194 | 14 | >AK134874_545_713_RC_B3A |
| NM_177328 | 787 | 971 | −670 RC | B3A | SINE/B2 | −4 | 194 | 7 | >AK134874_787_971_RC_B3A |
| NM_021899 | 161 | 307 | −1092 RC | B3A | SINE/B2 | −46 | 152 | 1 | >AK135206_161_307_RC_B3A |
| NM_010332 | 228 | 409 | −1967 RC | B3 | SINE/B2 | −28 | 188 | 2 | >AK135599_228_409_RC_B3 |
| NM_172407 | 1470 | 1683 | −74 RC | B3 | SINE/B2 | −5 | 211 | 2 | >AK143014_1470_1683_RC_B3 |
| NM_001009935 | 1389 | 1495 | −157 RC | B3 | SINE/B2 | −96 | 120 | 1 | >AK143784_1389_1495_RC_B3 |
| NM_019827 | 2953 | 3143 | −1064 RC | B3 | SINE/B2 | −1 | 215 | 1 | >AK145079_2953_3143_RC_B3 |
| NM_011212 | 2131 | 2283 | −1263 RC | B3A | SINE/B2 | −47 | 151 | 2 | >AK148045_2131_2283_RC_B3A |
| NM_010567 | 984 | 1129 | −78 RC | B3A | SINE/B2 | −60 | 138 | 2 | >AK148373_984_1129_RC_B3A |
| NM_001110504 | 1406 | 1594 | −400 RC | B3A | SINE/B2 | −10 | 188 | 2 | >AK149403_1406_1594_RC_B3A |
| NM_026036 | 2270 | 2439 | 0 RC | B3 | SINE/B2 | −4 | 212 | 27 | >AK149843_2270_2439_RC_B3 |
| NM_010398 | 1292 | 1476 | −698 RC | B3A | SINE/B2 | −11 | 187 | 3 | >AK157261_1292_1476_RC_B3A |
| NM_001110504 | 1292 | 1362 | −572 RC | B3A | SINE/B2 | −112 | 86 | 11 | >AK160921_1292_1362_RC_B3A |
| NM_007893 | 1080 | 1254 | −746 RC | B3 | SINE/B2 | 0 | 216 | 21 | >AK163105_1080_1254_RC_B3 |
| NM_007893 | 1427 | 1491 | −509 RC | B3A | SINE/B2 | −82 | 116 | 46 | >AK163105_1427_1491_RC_B3A |
| NM_030714 | 1954 | 2064 | −333 RC | B3 | SINE/B2 | −95 | 121 | 2 | >AK165234_1954_2064_RC_B3 |
| NM_001110101 | 853 | 1043 | −1516 RC | B3 | SINE/B2 | −5 | 211 | 6 | >AK169421_853_1043_RC_B3 |
| NM_001110101 | 1742 | 1936 | −623 RC | B3 | SINE/B2 | −2 | 214 | 8 | >AK169421_1742_1936_RC_B3 |

INDUSTRIAL APPLICABILITY

According to the present invention, it is possible to provide a functional nucleic acid molecule having a function of improving efficiency of translation from an RNA, and a use thereof.

SEQUENCE LISTING

RK23223PCT Sequence Listing

The invention claimed is:

1. A functional nucleic acid molecule that increases protein synthesis efficiency, the functional nucleic acid molecule comprising:
   (a) a target determinant sequence comprising an antisense sequence that is antisense to a target sequence in the protein-encoding RNA for which protein synthesis efficiency is to be increased; and
   (b) a regulatory sequence having the activity of increasing protein synthesis efficiency, wherein the regulatory sequence comprising a SINE (Short Interspersed Element) derived sequence.

2. The functional nucleic acid molecule as set forth in claim 1, wherein the SINE derived sequence is a SINE-B2-derived sequence.

3. The functional nucleic acid molecule as set forth in claim 1, wherein:
   the regulatory sequence is selected from the group consisting of the following (1) through (5):
   (1) an RNA, which is encoded by a DNA consisting of the nucleotide sequence shown in SEQ ID No: 1;
   (2) an RNA, which is encoded by a DNA consisting of the nucleotide sequence shown in SEQ ID No:2;
   (3) an RNA, which is encoded by a DNA consisting of the nucleotide sequence shown in SEQ ID No:3;
   (4) a nucleic acid (i) which has at least 25% similarity to the RNA, which is encoded by a DNA consisting of the nucleotide sequence shown in SEQ ID No: 1, 2 or 3 and (ii) which has a function of increasing the protein synthesis efficiency; and
   (5) a nucleic acid (i) which is encoded by a DNA in which not less than 1 but not more than 200 nucleotides are deleted, substituted, added, and/or inserted in the nucleotide sequence shown in SEQ ID No: 1 or 2 and (ii) which has a function of increasing the protein synthesis efficiency.

4. The functional nucleic acid molecule as set forth in claim 1, wherein the target determinant sequence is located between a 5'-terminal and the regulatory sequence in the functional nucleic acid molecule.

5. The functional nucleic acid molecule as set forth in claim 1, wherein the target determinant sequence has a length of 7 nucleotides to 250 nucleotides.

6. The functional nucleic acid molecule as set forth in claim 1, wherein the target determinant sequence has at least 60% similarity to a sequence complementary to a corresponding sequence in the protein-encoding RNA or a sequence around the first 5'-terminal start codon of the protein-encoding sequence.

7. The functional nucleic acid molecule as set forth in claim 1, wherein the regulatory sequence of the functional nucleic acid molecule is oriented in a reverse direction relative to the direction of translation.

8. The functional nucleic acid molecule as set forth in claim 1, wherein the target determinant sequence is designed to be hybridizable with a 5'-UTR (untranslated region) of the protein-encoding RNA or a sequence around the first 5'-terminal start codon of the protein-encoding sequence.

9. A DNA molecule encoding a functional nucleic acid molecule as set forth in-claim 1.

10. An expression vector comprising a functional nucleic acid molecule as set forth in claim 1.

11. A composition for increasing protein synthesis efficiency, which comprises a functional nucleic acid molecule as set forth claim 1.

12. A method for increasing the protein synthesis efficiency, comprising the step of:
  (a) allowing a functional nucleic acid molecule as set forth in claim 1 to coexist with a protein-encoding RNA, which partial sequence of the protein-encoding RNA has similarity with the target determinant sequence of the functional RNA molecule.

13. The method as set forth in claim 12, wherein:
  the step (a) comprises transfecting into a cell the functional nucleic acid molecule or a DNA molecule encoding the functional nucleic acid molecule.

14. A method for producing a protein, comprising the step of increasing the protein synthesis efficiency by a method for increasing the protein synthesis efficiency as set forth in claim 12.

15. A method for treating a disease that is caused by a quantitative decrease in a protein, comprising the step of increasing the protein synthesis efficiency by a method for increasing the protein synthesis efficiency as set forth in claim 12 in a subject having the disease or a predisposition to the disease.

16. An expression vector comprising a DNA molecule as set forth in claim 9.

17. A composition for increasing protein synthesis efficiency, which comprises a DNA molecule as set forth in claim 9.

18. A composition for increasing protein synthesis efficiency, which comprises an expression vector as set forth in claim 10.

* * * * *